(12) United States Patent
Swenson et al.

(10) Patent No.: US 12,239,993 B2
(45) Date of Patent: *Mar. 4, 2025

(54) DEVICES AND METHODS FOR ANTIBIOTIC SUSCEPTIBILITY TESTING

(71) Applicant: Visby Medical, Inc., San Jose, CA (US)

(72) Inventors: David Swenson, Santa Clara, CA (US); Phoebe Cao, Sunol, CA (US); Gary Schoolnik, Washington, DC (US); Bryan D. Knysh, Santa Clara, CA (US); Teresa M. Abraham, San Jose, CA (US)

(73) Assignee: Visby Medical, Inc., San Jose, CA (US)

( * ) Notice: Subject to any disclaimer, the term of this patent is extended or adjusted under 35 U.S.C. 154(b) by 974 days.

This patent is subject to a terminal disclaimer.

(21) Appl. No.: 17/273,100

(22) PCT Filed: Sep. 3, 2019

(86) PCT No.: PCT/US2019/049385
§ 371 (c)(1),
(2) Date: Mar. 3, 2021

(87) PCT Pub. No.: WO2020/051156
PCT Pub. Date: Mar. 12, 2020

(65) Prior Publication Data
US 2021/0299669 A1 Sep. 30, 2021

Related U.S. Application Data

(60) Provisional application No. 62/820,359, filed on Mar. 19, 2019, provisional application No. 62/726,379, filed on Sep. 3, 2018.

(51) Int. Cl.
*B01L 7/00* (2006.01)
*C12Q 1/6827* (2018.01)
*C12Q 1/689* (2018.01)

(52) U.S. Cl.
CPC ............ *B01L 7/525* (2013.01); *C12Q 1/6827* (2013.01); *C12Q 1/689* (2013.01); *B01L 2200/10* (2013.01); *B01L 2200/16* (2013.01); *B01L 2400/0478* (2013.01); *B01L 2400/0644* (2013.01); *C12Q 2600/106* (2013.01); *C12Q 2600/156* (2013.01)

(58) Field of Classification Search
CPC .. B01L 7/525; B01L 2200/10; B01L 2200/16; B01L 2400/0478; B01L 2400/0644; B01L 2200/0663; C12Q 1/6827; C12Q 1/689; C12Q 2600/106; C12Q 2600/156
See application file for complete search history.

(56) References Cited

U.S. PATENT DOCUMENTS

| | | |
|---|---|---|
| 4,789,630 A | 12/1988 | Bloch et al. |
| 5,229,297 A | 7/1993 | Schnipelsky et al. |
| 5,498,392 A | 3/1996 | Wilding et al. |
| 5,726,026 A | 3/1998 | Wilding et al. |
| 5,882,903 A | 3/1999 | Andrevski et al. |
| 5,922,591 A | 7/1999 | Anderson et al. |
| 6,153,425 A | 11/2000 | Kozwich et al. |
| 6,235,479 B1 | 5/2001 | Rogers |
| 6,369,893 B1 | 4/2002 | Christel et al. |
| 6,374,684 B1 | 4/2002 | Dority |
| 6,610,499 B1 | 8/2003 | Fulwyler et al. |
| 6,645,758 B1 | 11/2003 | Schnipelsky et al. |
| 6,780,617 B2 | 8/2004 | Chen |
| 6,821,771 B2 | 11/2004 | Festoc |
| 6,893,879 B2 | 5/2005 | Petersen et al. |
| 7,189,522 B2 | 3/2007 | Esfandiari |
| 7,297,313 B1 | 11/2007 | Northrup et al. |
| 7,384,782 B2 | 6/2008 | Nakatani et al. |
| 7,416,892 B2 | 8/2008 | Battrell et al. |
| 7,553,675 B2 | 6/2009 | Jerome et al. |
| 7,569,382 B2 | 8/2009 | Li |
| 7,579,172 B2 | 8/2009 | Cho et al. |
| 7,592,139 B2 | 9/2009 | West et al. |
| 7,648,835 B2 | 1/2010 | Breidford et al. |

(Continued)

FOREIGN PATENT DOCUMENTS

| CN | 103820439 A | 5/2014 |
|---|---|---|
| CN | 108884489 A | 11/2018 |

(Continued)

OTHER PUBLICATIONS

Huang (Microarrays 4.4 (2015): 570-595) (Year: 2015).*

(Continued)

*Primary Examiner* — Narayan K Bhat
(74) *Attorney, Agent, or Firm* — Cooley LLP

(57) ABSTRACT

The disclosure relates generally to molecular diagnostic devices configured to amplifying a single nucleotide polymorphism (SNP) locus and discriminate between two or more allelic variants of the SNP, indicating presence or absence of a target allele. In some embodiments, the molecular diagnostic devices are capable of detecting, at point-of-care, SNPs associated with resistance or susceptibility to antibiotic treatment of bacterial infections. In other aspects, the disclosure provides methods of treatment for disease or disorders (e.g. bacterial infections) where treatment is guided by presence or absence of an allele at a SNP locus as determined by such molecular diagnostic devices.

22 Claims, 29 Drawing Sheets
Specification includes a Sequence Listing.

(56) References Cited

U.S. PATENT DOCUMENTS

| | | |
|---|---|---|
| 7,705,339 B2 | 4/2010 | Smith et al. |
| 7,754,452 B2 | 7/2010 | Kim et al. |
| 7,767,439 B2 | 8/2010 | Oh et al. |
| 7,799,521 B2 | 9/2010 | Chen et al. |
| 7,914,986 B2 | 3/2011 | Nunn |
| 7,985,716 B2 | 7/2011 | Yershov et al. |
| 7,998,757 B2 | 8/2011 | Darrigrand et al. |
| 8,018,593 B2 | 9/2011 | Tan et al. |
| 8,048,386 B2 | 11/2011 | Dority et al. |
| 8,088,616 B2 | 1/2012 | Handique |
| 8,110,392 B2 | 2/2012 | Battrell et al. |
| 8,133,671 B2 | 3/2012 | Williams et al. |
| 8,133,703 B2 | 3/2012 | Ching et al. |
| 8,163,535 B2 | 4/2012 | Reed et al. |
| 8,169,610 B2 | 5/2012 | Oldham et al. |
| 8,187,557 B2 | 5/2012 | Van Atta et al. |
| 8,216,832 B2 | 7/2012 | Battrell et al. |
| 8,232,091 B2 | 7/2012 | Maltezos et al. |
| 8,232,094 B2 | 7/2012 | Hasson et al. |
| 8,298,763 B2 | 10/2012 | Regan |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,372,340 B2 | 2/2013 | Bird et al. |
| 8,389,960 B2 | 3/2013 | Pieprzyk et al. |
| 8,394,608 B2 | 3/2013 | Ririe et al. |
| 8,426,134 B2 | 4/2013 | Piepenburg et al. |
| 8,492,136 B2 | 7/2013 | Carlisle et al. |
| 8,557,518 B2 | 10/2013 | Jovanovich et al. |
| 8,637,250 B2 | 1/2014 | Jenison |
| 8,722,426 B2 | 5/2014 | Lambotte et al. |
| 8,728,765 B2 | 5/2014 | Ching et al. |
| 8,765,367 B2 | 7/2014 | Breidenthal et al. |
| 8,765,454 B2 | 7/2014 | Zhou et al. |
| 8,772,017 B2 | 7/2014 | Battrell et al. |
| 8,795,592 B2 | 8/2014 | Eiriksson |
| 8,894,946 B2 | 11/2014 | Nielsen et al. |
| 8,895,255 B1 | 11/2014 | Goldberg et al. |
| 8,900,828 B2 | 12/2014 | Smith et al. |
| 8,911,941 B2 | 12/2014 | Michlitsch |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,561 B1 | 3/2015 | Cai et al. |
| 9,012,236 B2 | 4/2015 | Jovanovich et al. |
| 9,023,639 B2 | 5/2015 | Kim et al. |
| 9,034,168 B2 | 5/2015 | Khattak et al. |
| 9,044,729 B2 | 6/2015 | Rengifo et al. |
| 9,150,907 B2 | 10/2015 | Shaikh et al. |
| 9,207,236 B2 | 12/2015 | Cary |
| 9,238,833 B2 | 1/2016 | Chen et al. |
| 9,260,750 B2 | 2/2016 | Hillebrand et al. |
| 9,387,478 B2 | 7/2016 | Bergstedt et al. |
| 9,428,781 B2 | 8/2016 | Cai et al. |
| 9,453,255 B2 | 9/2016 | Ozawa et al. |
| 9,469,871 B2 | 10/2016 | Bearinger et al. |
| 9,475,049 B2 | 10/2016 | Siciliano |
| 9,623,415 B2 | 4/2017 | Andreyev et al. |
| 9,663,821 B2 | 5/2017 | Unger et al. |
| 9,718,058 B2 | 8/2017 | Khattak et al. |
| 9,725,754 B2 | 8/2017 | Boyle et al. |
| 9,752,182 B2 | 9/2017 | Collier et al. |
| 9,789,483 B2 | 10/2017 | Khattak et al. |
| 9,890,415 B2 | 2/2018 | Stehr et al. |
| 10,040,069 B2 | 8/2018 | Moore et al. |
| 10,052,629 B2 | 8/2018 | Andreyev et al. |
| 10,112,196 B2 | 10/2018 | Andreyev et al. |
| 10,112,197 B2 | 10/2018 | Andreyev et al. |
| 10,124,334 B2 | 11/2018 | Andreyev et al. |
| 10,146,909 B2 | 12/2018 | Dimov et al. |
| 10,173,182 B2 | 1/2019 | Tachibana et al. |
| 10,195,610 B2 | 2/2019 | Tang et al. |
| 10,233,483 B2 | 3/2019 | Talebpour et al. |
| 10,603,664 B2 | 3/2020 | Khattak |
| 11,080,848 B2 | 8/2021 | Dimov et al. |
| 11,162,130 B2 | 11/2021 | Andreyev et al. |
| 11,167,285 B2 | 11/2021 | Andreyev et al. |
| 11,168,354 B2 | 11/2021 | Andreyev et al. |
| 11,273,443 B2 | 3/2022 | Andreyev et al. |
| 2003/0027203 A1 | 2/2003 | Fields |
| 2003/0027244 A1 | 2/2003 | Colston et al. |
| 2004/0018502 A1 | 1/2004 | Makino et al. |
| 2004/0110141 A1 | 6/2004 | Pusey et al. |
| 2004/0209331 A1 | 10/2004 | Ririe |
| 2005/0059030 A1 | 3/2005 | Bao et al. |
| 2005/0100946 A1 | 5/2005 | Lipshutz et al. |
| 2005/0142036 A1 | 6/2005 | Kim et al. |
| 2005/0194316 A1 | 9/2005 | Pourahmadi et al. |
| 2005/0227275 A1 | 10/2005 | Jung et al. |
| 2006/0127924 A1 | 6/2006 | Hellyer et al. |
| 2006/0160205 A1 | 7/2006 | Blackburn et al. |
| 2006/0177841 A1 | 8/2006 | Wangh et al. |
| 2006/0210998 A1 | 9/2006 | Kettlitz et al. |
| 2006/0258012 A1 | 11/2006 | Yang et al. |
| 2007/0026391 A1 | 2/2007 | Stoughton et al. |
| 2007/0036691 A1 | 2/2007 | Lin et al. |
| 2007/0042427 A1 | 2/2007 | Gerdes et al. |
| 2007/0154922 A1 | 7/2007 | Collier et al. |
| 2007/0277251 A1 | 11/2007 | Wartiovaara et al. |
| 2007/0292941 A1 | 12/2007 | Handique et al. |
| 2008/0038737 A1 | 2/2008 | Smith et al. |
| 2008/0050735 A1 | 2/2008 | Pushnova |
| 2008/0057572 A1 | 3/2008 | Petersen et al. |
| 2008/0113391 A1 | 5/2008 | Gibbons et al. |
| 2008/0153078 A1 | 6/2008 | Braman et al. |
| 2008/0280285 A1 | 11/2008 | Chen et al. |
| 2009/0035780 A1 | 2/2009 | McCarthy et al. |
| 2009/0075269 A1 | 3/2009 | Caplin |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1 | 1/2010 | Sarofim et al. |
| 2010/0025242 A1 | 2/2010 | Pamula |
| 2010/0035349 A1 | 2/2010 | Bau et al. |
| 2010/0075302 A1 | 3/2010 | Perlin et al. |
| 2010/0173393 A1 | 7/2010 | Handique et al. |
| 2010/0210038 A1 | 8/2010 | Blatt et al. |
| 2010/0291536 A1 | 11/2010 | Viljoen et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Janovich et al. |
| 2011/0160090 A1 | 6/2011 | Cary |
| 2011/0203688 A1 | 8/2011 | Reed et al. |
| 2011/0253224 A1 | 10/2011 | Linder et al. |
| 2011/0275055 A1 | 11/2011 | Conner |
| 2011/0308313 A1 | 12/2011 | Azimi et al. |
| 2011/0312074 A1 | 12/2011 | Azimi et al. |
| 2011/0312666 A1 | 12/2011 | Azimi et al. |
| 2011/0312787 A1 | 12/2011 | Silverbrook et al. |
| 2011/0312841 A1 | 12/2011 | Silverbrook et al. |
| 2012/0021454 A1 | 1/2012 | Bikker et al. |
| 2012/0064534 A1 | 3/2012 | Pipper et al. |
| 2012/0088294 A1 | 4/2012 | Sun et al. |
| 2012/0135511 A1 | 5/2012 | Battrell et al. |
| 2012/0141337 A1 | 6/2012 | Maltezos et al. |
| 2012/0264114 A1 | 10/2012 | Wacogne et al. |
| 2012/0282681 A1 | 11/2012 | Teixeira et al. |
| 2012/0282684 A1 | 11/2012 | Fritchie et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0217026 A1 | 8/2013 | Egan et al. |
| 2013/0224729 A1 | 8/2013 | Church et al. |
| 2013/0295570 A1 | 11/2013 | Wangh et al. |
| 2014/0045191 A1 | 2/2014 | DeJohn et al. |
| 2014/0073013 A1 | 3/2014 | Gorman et al. |
| 2014/0087359 A1 | 3/2014 | Njoroge et al. |
| 2014/0274770 A1 | 9/2014 | Pack |

(56) References Cited

U.S. PATENT DOCUMENTS

| | | |
|---|---|---|
| 2014/0329301 A1 | 11/2014 | Handique |
| 2014/0342356 A1 | 11/2014 | Stender et al. |
| 2015/0258273 A1 | 9/2015 | Payne et al. |
| 2015/0290639 A1 | 10/2015 | Evtodienko |
| 2015/0322483 A1 | 11/2015 | Nakamura et al. |
| 2015/0346097 A1 | 12/2015 | Battrell et al. |
| 2016/0008811 A1 | 1/2016 | Aser et al. |
| 2016/0077015 A1 | 3/2016 | Holmes et al. |
| 2016/0186240 A1* | 6/2016 | Andreyev ............ B01L 3/5029 435/287.2 |
| 2016/0222442 A1 | 8/2016 | Cary |
| 2016/0251702 A1 | 9/2016 | Chattopadhyay et al. |
| 2016/0256870 A1 | 9/2016 | Ismagilov et al. |
| 2016/0281149 A1 | 9/2016 | Hassibi et al. |
| 2016/0289669 A1 | 10/2016 | Fan et al. |
| 2016/0310948 A1 | 10/2016 | Nowakowski et al. |
| 2017/0021356 A1 | 1/2017 | Dority et al. |
| 2017/0058324 A1 | 3/2017 | Balog et al. |
| 2017/0121756 A1 | 5/2017 | Abate et al. |
| 2017/0152510 A1 | 6/2017 | Lorenz |
| 2017/0173585 A1 | 6/2017 | Mahony et al. |
| 2017/0247745 A1 | 8/2017 | Schultz et al. |
| 2017/0260570 A1 | 9/2017 | Balashov et al. |
| 2017/0304829 A1 | 10/2017 | Andreyev et al. |
| 2018/0135108 A1 | 5/2018 | Etchebarne |
| 2018/0135110 A1 | 5/2018 | Saxena et al. |
| 2018/0304260 A1 | 10/2018 | Thomas et al. |
| 2018/0355410 A1 | 12/2018 | Lee et al. |
| 2019/0022643 A1 | 1/2019 | Andreyev et al. |
| 2019/0030532 A1 | 1/2019 | Andreyev et al. |
| 2019/0032104 A1 | 1/2019 | Lowery et al. |
| 2019/0040451 A1 | 2/2019 | Mahony et al. |
| 2019/0060895 A1 | 2/2019 | Myers, III et al. |
| 2019/0083975 A1 | 3/2019 | Mitra et al. |
| 2019/0094114 A1 | 3/2019 | Myers, III et al. |
| 2019/0136226 A1 | 5/2019 | Swenson et al. |
| 2019/0151844 A1 | 5/2019 | Andreyev et al. |
| 2019/0169677 A1 | 6/2019 | Andreyev et al. |
| 2019/0193077 A1 | 6/2019 | Andreyev et al. |
| 2019/0232283 A1 | 8/2019 | Andreyev et al. |
| 2019/0232293 A1 | 8/2019 | Tang et al. |
| 2019/0262827 A1 | 8/2019 | Lalonde et al. |
| 2020/0086324 A1 | 3/2020 | Swenson et al. |
| 2020/0346213 A1 | 11/2020 | Andreyev et al. |
| 2020/0406256 A1 | 12/2020 | Andreyev et al. |
| 2020/0406257 A1 | 12/2020 | Andreyev et al. |
| 2020/0408750 A1 | 12/2020 | Khattak |
| 2021/0039097 A1 | 2/2021 | Andreyev et al. |
| 2021/0071236 A1 | 3/2021 | Andreyev et al. |
| 2021/0207194 A1 | 7/2021 | Ciopyk et al. |
| 2022/0055032 A1 | 2/2022 | Andreyev et al. |
| 2022/0186208 A1 | 6/2022 | Swenson et al. |
| 2022/0203365 A1 | 6/2022 | Abraham et al. |
| 2022/0325363 A1 | 10/2022 | Broughton et al. |

FOREIGN PATENT DOCUMENTS

| | | | |
|---|---|---|---|
| EP | 2682480 A1 | | 1/2014 |
| KR | 20120044060 | * | 5/2012 |
| WO | WO-0118017 A1 | | 3/2001 |
| WO | WO2001/049416 A1 | | 7/2001 |
| WO | WO-2007/061943 | | 5/2007 |
| WO | WO2008/082432 | | 7/2008 |
| WO | WO2008/149111 | | 12/2008 |
| WO | WO-2012/009813 | | 1/2012 |
| WO | WO2014/144548 A2 | | 9/2014 |
| WO | WO-2015035260 A1 | | 3/2015 |
| WO | WO2015/164770 A1 | | 10/2015 |
| WO | WO-2016086305 A1 | | 6/2016 |
| WO | WO-2016106391 A1 | | 6/2016 |
| WO | WO2016/203019 A1 | | 12/2016 |
| WO | WO2017/090043 A1 | | 6/2017 |
| WO | WO2017/151195 | | 9/2017 |
| WO | WO2017/160840 A1 | | 9/2017 |
| WO | WO-2018087205 A1 | | 5/2018 |
| WO | WO2018/119443 | | 6/2018 |
| WO | WO2020/180858 | | 9/2020 |
| WO | WO-2020/214557 | | 10/2020 |
| WO | WO2020/223257 | | 11/2020 |

OTHER PUBLICATIONS

Office Action for U.S. Appl. No. 17/139,451, mailed May 4, 2021, 7 pages.

International Search Report and Written Opinion for International Application No. PCT/US20/67642, mailed May 3, 2021, 17 pages.

Examination Report No. 1 for AU Application No. 2019337088, mailed Oct. 15, 2021, 4 pages.

Benett, William et al. "Handheld advanced nucleic acid analyzer," Event: Environmental and Industrial Sensing, Boston, MA, Proceedings of SPIE, vol. 4200 (2000), pp. 55-63.

Edouard et al., "Cost-Effective Pooling of DNA from Nasopharyngeal Swab Samples for Large-Scale Detection of Bacteria by Real-Time PCR," Journal of Clinical Microbiology, vol. 53, No. 3, Mar. 2015, pp. 1002-1004.

Elnifro, Elfath M. et al. "Multiplex PCR: Optimization and Application in Diagnostic Virology," Clinical Microbiology Reviews, vol. 13, No. 4, Oct. 2000, pp. 559-570.

Hassibi et al. "An array-based melt curve analysis method for the identification and classification of closely related pathogen strains." Biology Methods and Protocols 2018; pp. 1-12.

Kim, Young Ho et al., "Performance evaluation of thermal cyclers for PCR in a rapid cycling condition," BioTechniques, www.biotechniques.com, vol. 44, No. 4, 2008, pp. 495-505.

Primiceri, Elisabetta et al. "Key Enabling Technologies for Point-of-Care Diagnostics," MDPI, Sensors 18, 3607; doi:10.3390/s18113607, www.mdpi.com/journal/sensors, 2018, pp. 1-34.

Richards, James et al. "Miniaturized detection system for handheld PCR assays," Event: Environmental and Industrial Sensing, Boston, MA, Proceedings of SPIE, vol. 4200 (2000), pp. 64-73.

Rybicki et al., "Standard PCR Protocol," Feb. 1, 2001, 4 pages.

Terhes et al. "Comparison of a Rapid Molecular Method, the BD GeneOhm Cdiff Assay, to the Most Frequently Used Laboratory Tests for Detection of Toxin-Producing Clostridium difficile in Diarrheal Feces," Journal of Clinical Microbiology, vol. 47, No. 11, Nov. 2009, pp. 3478-3481.

Tsaloglou, Maria-Nefeli et al. "Handheld isothermal amplification and electrochemical detection of DNA in resource-limited settings," Analytical Biochemistry 543, 2018, pp. 116-121.

Ullerich, Lars et al. "Ultra-fast PCR technologies for point-of-care testing," De Gruyter, J. Lab Med 2017; 41(5), pp. 239-244.

Yotoriyama, T. et al. "Miniaturized PCR Device for Rapid Detection of Infectious Agents," 14th International Conference on Miniaturized Systems for Chemistry and Life Sciences, Oct. 3-17, 2010, pp. 142-144.

White, Adam K. et al. High-throughput microfluidic single-cell RT-qPCR, PNAS, Aug. 23, 2011, vol. 108, No. 34, pp. 13999-14004.

White, Adam K. et al. "High-throughput microfluidic single-cell RT-qPCR, Supporting Information White et al. 10.1073/pnas. 1019446108" PNAS, Aug. 23, 2011, vol. 108, No. 34, pp. 1-9.

Zhang, Chunsun et al. "PCR microfluidic devices for DNA amplification," Biotechnology Advances 24, (2006) pp. 243-284.

Australian Patent Office, 2nd Examination Report for AU2019337088, Apr. 6, 2022, 3 pages.

Chinese Patent Office, First Office Action for CN2019800714356, Apr. 27, 2022, 12 pages.

European Patent Office, Extended European Search Report for 19856734.9, Jun. 29, 2022, 11 pages.

Oleastro, et al., Real-Time PCR Assay for Rapid and Accurate Detection of Point Mutations Conferring Resistance to Clarithromycin in Helicobacter pylori, Journal of Clinical Microbiology, vol. 41, No. 1, Jan. 2003, pp. 397-402, XP055274907, US ISSN: 0095-1137, DOI: 10.1128/JCM.41.1.397-402.2003.

(56) References Cited

OTHER PUBLICATIONS

Rajendran, et al., Smartphone detection of antibiotic resistance using convective PCR and a lateral flow assay, Sensors and Actuators B: Chemical, Nov. 2019, 10 pages.
International Search Report and Written Opinion for PCT/US2019/049385, mailed Nov. 15, 2019, 12 pages.
Extended European Search Report for European Application No. 17821297.3, mailed Dec. 17, 2019, 21 pages.
Ahrberg, Christian D. et al. "Polymerase chain reaction in microfluidic devices," © The Royal Society of Chemistry 2016, Lab Chip, 16, pp. 3866-3884, 20 pgs.
Brunklaus, S. et al., Fast nucleic acid amplification for integration in point-of-care applications, Electrophoresis, 2012, vol. 33, pp. 3222-3228.
Choi, Gihoon et al., "A field-deployable mobile molecular diagnostic system for malaria at the point of need," Lab on a Chip, Royal Society of Chemistry, 2016, 16, 4341-4349.
Dutta, Gorachand et al. "Microfluidic Devices for Label-Free DNA Detection," Chemosensors, Sep. 25, 2018, 6, 43 www.mdpi.com/journal/chemosensors, 20 pgs.
Gehring et al. "A High-Throughput, Precipitating Colorimetric Sandwich ELISA Microarray for Shiga Toxins," J. Toxins, vol. 6, p. 1855-72, Jun. 11, 2014.
Harding-Esch et al. "A 30-min nucleic acid amplification point-of-care test for genital *Chlamidya trachomatis* infection in women: a prospective, multi-center study of diagnostic accuracy." EBioMedicine 2018; 28:120-27.
Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.
Hwang et al., "Black Printed Circuit Board-based Micro-Polymerase Chain Reaction Chip Structure for Fluorescence Detection Test", International Journal of Control and Automation (2015); vol. 8, No. 10: pp. 15-24 (10 pages).
Interbiotech, "Enzymatic substrates for ImmunoAssays," [retreived from the Internet Nov. 18, 2017: <http://www.interchim.fr/ft/B/BA357a.pdf>], 10 pages.
Kim, Yong Tae et al. "Integrated Microdevice of reverse transcription-polymerase chain reaction with colorimetric immunochromatographic detection for rapid gene expression analysis of influenza A H1N1 virus," Biosensors and Bioelectronics, Elsevier Science Ltd UK, Amsterdam, NL V. 33 No. 1, pp. 88-94, Dec. 14, 2011.
Kim, Jungkyu et al. "Automated microfluidic DNA/RNA extraction with both disposable and reusable components," Journal of Micromechanics and Microengineering, vol. 22, No. 1, Dec. 20, 2011, 21 pages.
Kopp et al., "Chemical Amplification: Continuous-Flow PCR on a Chip", Science (1998); 280 (5366): 1046-1048.
Lee et al. "A polymer lab-on-a-chip for reverse transcription (RT)-PCR based point-of-care clinical diagnostics," The Royal Society of Chemistry, vol. 8, pp. 2121-2127, Oct. 31, 2008.
Lee et al. "Single-channel multiplexing without melting curve analysis in real-time PCR," Scientific Reports, Dec. 11, 2014, vol. 4, Art. No. 7439, pp. 1-6, entire document.
Mohammed et al., Modeling of Serpentine Continuous Flow Polymerase Chain Reaction Microfluidics, IJEST, vol. 4, No. 3, pp. 1183-1189, Mar. 2012.
Petralia, Salvatore et al. "PCR Technologies for Point of Care Testing: Progress and Perspectives," ACS Sensors, 2017, 2 (7), pp. 876-891, Jul. 6, 2017.
Poritz, Mark A. et al., "FilmArray, an Automated Nested Multiplex PCR System for Multi-Pathogen Detection: Development and Application to Respiratory Tract Infection," PLoS ONE www.plosone.org, Oct. 2011, vol. 6, Issue 10 (14 pgs.).
Roskos, Kristina et al. "Simple System for Isothermal DNA Amplification Coupled to Lateral Flow Detection," PLoS ONE 8(7): e69355. https://doi.org/10.1371/journal.pone.0069355; Jul. 26, 2013, 11 pages.
Shafagati, et al., The Use of Nano Trap Particles as a Sample Enrichment Method to Enhance the Detection of Rift Valley Fever Virus. PLOS Neglected Tropical Diseases, Jul. 4, 2013; 7(7): e2296.
Tanriverdi et al. A rapid and automated sample-to-result HIV load test for near-patient application. J Infect Dis., 201 Suppl 1:S52-S58, 2010.
Thiha et al. A Colorimetric Enzyme-Linked Immunoabsorbent Assay (ELISA) Detection Platform for a Point-Of-Care Dengue Detection System on a Lab-on-Compact-Disc; Sensors ISSN 1424-8220, May 18, 2015.
Wu, Jinbo et al. "Extraction, amplification and detection of DNA in microfluidic chip-based assays," © Springer-Verlag Wein 2013, pp. 1611-1631.
Zhang, Chunsun et al. "Survey and Summary—Miniaturized PCR chips for nucleic acid amplification and analysis: latest advances and future trends," Nucleic Acids Research, 2007, vol. 35, No. 13, pp. 4223-4237.
Zumla, Alimuddin et al., "Emerging respiratory tract infections 4—Rapid point of care diagnostic tests for viral and bacterial respiratory tract infections—needs, advances, and future prospects," Lancet Infect. Dis. www.thelancet/infection, vol. 14, Nov. 2014, pp. 1123-1135.
Public Health Enland. "Update on investigation of UK case of Neisseria gonorrhoeae with high-level resistance to azithromycin and resistance to ceftriaxone acquired abroad," Health Protection Report, vol. 12, No. 14 (Apr. 20, 2018).
Hermarajata, P. et al. "Performance and Verification of a Real-Time PCR Assay Targeting the gyrA Gene for Prediction of Ciprofloxacin Resistance in Neisseria ghonrrhoeae," J. Clinical Microbiology vol. 54, No. 3: 805-808; (Jan. 6, 2016).
Allan-Blitz, L. et al. "Ciprofloxacin May be Efficacious in Treating Wild-Type Gyrase A Genotype Neisseria gonorrhoeae Infections," Sexually Transmitted Diseases, vol. 45, Issue 4, p. e18 (Apr. 2018).
Wong, L.K. et al. "Real-Time PCR Targeting the penA Mosaic XXXIV Type for Prediction of Extended-Spectrum-Cephalosporin Susceptibility in Clinical Neisseria gonorrhoeae Isolates," Am. Society for Microbiology, Antimicrobial Agents and Chemotherapy, vol. 61, Issue 11 (Nov. 2017), 6 pages.
Buono, S. et al. "Stemming the tide of drug-resistant Neisseria gonorrhoeae: the need for an individualized approach to treatment," J. Antimicrobial Chemotherapy, vol. 70, pp. 374-381 (Oct. 19, 2014).
Kerremans, J. et al. "Rapid identification and antimicrobial susceptibility testing reduce antibiotic use and accelerate pathogen-directed antibiotic use," J. Antimicrobial Chemotherapy, vol. 61, pp. 428-435 (Dec. 21, 2007).
Tuite, A. et al. "Impact of Rapid Susceptibility Testing and Antibiotic Selection Strategy on the Emergence and Spread of Antibiotic Resistance in Gonorrhea," J. Infectious Diseases, 216:1141-9 (Nov. 1, 2017).
Herbst De Cortina, S. et al. "A Systematic Review of Point of Care Testing for Chlamydia trachomatis, Neisseria gonorrhoeae, and Trichomonas vaginalis," Infectious Diseases in Obstetrics and Gynecology, vol. 2016, 17 pages (Mar. 7, 2016).
Huppert, J. et al. "What's the Point? How Point-of-Care STI Tests can Impact Infected Patients," National Institutes of Health, vol. 9(1): pp. 36-46 (Mar. 1, 2010).
Allan-Blitz, L. et al. "Wild-Type Gyrase A Genotype of Neisseria gonorrhoeae Predicts In Vitro Susceptibility to Ciprofloxacin: A Systematic Review of the Literature and Meta-Analysis," Sex Transm Dis. 44(5): 261-265 (May 2017).
Fifer et al. "Sustained transmission of high-level azithromycin-resistant Neisseria gonorrhoeae in England: an observational study," Lancet Infect Dis 2018; 18: 573-81 (Mar. 6, 2018).
Grad, Y. et al. "Genomic Epidemiology of Gonococcal Resistance to Extended-Spectrum Cephalosporins, Macrolides, and Fluoroquinolones in the United States, 2000-2013," Journal of Infectious Diseases, 214: 1579-87 (2016).
Grad, Y. et al. "Genomic epidemiology of Neisseria gonorrhoeae with reduced susceptibility to cefixime in the USA: a retrospective observational study," Lancet Infect Dis 14: 220-26 (Jan. 22, 2014).

(56) References Cited

OTHER PUBLICATIONS

Mortimer, T. et al. "Applications of genomics to slow the spread of multidrug-resistant Neisseria gonorrhoeae," Annals of the New York Academy of Sciences, Special Issue: Antimicrobial Therapeutics Reviews; 1-17 (2018).
Unemo, M. et al. "High In Vitro Susceptibility to the Novel Spiropyrimidinetrione ETX0914 (AZD0914) among 873 Contemporary Clinical Neisseria gonorrhoeae Isolates from 21 European Countries from 2012 to 2014," Antimicrobial Agents and Chemotherapy, vol. 59, No. 9, pp. 5220-5225 (Sep. 2015).
Alm, R. et al. "Characterization of the Novel DNA Gyrase Inhibitor AZD0914: Low Resistance Potential and Lack of Cross-Resistance in Neisseria gonorrhoeae," Antimicrobial Agents and Chemotherapy, vol. 59, No. 3, pp. 1478-1486 (Mar. 2015).
Lindberg, R. et al. "Neisseria gonorrhoeae Isolates with Reduced Susceptibility to Cefixime and Ceftriaxone: Association with Genetic Polymorphisms in penA, mtrR, porB1b, and ponA," Antimicrobial Agents and Chemotherapy, vol. 51, No. 6, pp. 2117-2122 (Jun. 2007).
Dillard, J. "Genetic Manipulation of Neisseria gonorrhoeae," Curr Protoc Microbiol, Author Manuscript, 34 pgs (Nov. 2011).
Dize, L. et al. "Comparison of self-obtained penile-meatal swabs to urine for the detection of C. trachomatis, N. gonorrhoeae and T. vaginalis," Sex Transm Infect. 89(4): 305-307 (Jun. 2013).
Ng, L. et al. "Mutation in 23S rRNA Associated with Macrolide Resistance in Neisseria gonorrhoeae," Antimicrobial Agents and Chemotherapy, vol. 46, No. 9, pp. 3020-3025 (Sep. 2002).
Allan-Blitz, L. et al. "Implementation of a Rapid Genotypic Assay to Promote Targeted Ciprofloxacin Therapy of Neisseria gonorrhoeae in a Large Health System," Clinical Infectious Diseases, 64(9): 1268-70 (May 2017).
Dona, V. et al. "Multiplex Real-Time PCR Assay with High-Resolution Melting Analysis for Characterization of Antimicrobial Resistance in Neisseria gonorrhoeae," Journal of Clinical Microbiology, vol. 54, No. 8, pp. 2074-2081 (Aug. 2016).
Pond, M. et al. "Accurate detection of Neisseria gonorrhoeae ciprofloxacin susceptibility directly from genital and extragenital clinical samples: towards genotype-guided antimicrobial therapy," Journal of Antimicrobial Chemotherapy, 71: 897-902 (Jan. 26, 2016).
Buckley, C. et al. "Real-time PCR detection of Neisseria gonorrhoeae susceptibility to penicillin," Journal of Antimicrobial Chemotherapy, 71: 3090-3095 (Jul. 25, 2016).
Peterson, S. et al. "Molecular Assay for Detection of Genetic Markers Associated with Decreased Susceptibility to Cephalosporins in Neisseria gonorrhoeae," Journal of Clinical Microbiology, vol. 53, No. 7, pp. 2042-2048 (Jul. 2015).
Vernel-Pauillac, F. et al. "Quinolone Resistance in Neisseria gonorrhoeae: Rapid Genotyping of Quinolone Resistance-Determining Regions in gyrA and parC Genes by Melting Curve Analysis Predicts Susceptibility," Antimicrobial Agents and Chemotherapy, vol. 53, No. 3, pp. 1264-1267 (Mar. 2009).
Siedner, M. et al. "Real-Time PCR Assay for Detection of Quinolone-Resistant Neisseria gonorrhoeae in Urine Samples," Journal of Clinical Microbiology, vol. 45, No. 4, pp. 1250-1254 (Apr. 2007).
Buckley, C. et al. "Use of whole genome sequencing to investigate an increase in Neisseria gonorrhoeae infection among women in urban areas of Australia," Scientific Reports, 8:1503, 7 pages (Jan. 24, 2018).
Gose, S. et al. "Neisseria gonorrhoeae and extended-spectrum cephalosporins in California: surveillance and molecular detection of mosaic penA," BMC Infectious Diseases, 13:570, 9 pages (2013).
Melendez, J. et al. "Antimicrobial Susceptibility of Neisseria gonorrhoeae Isolates in Baltimore, Maryland, 2016: The Importance of Sentinel Surveillance in the Era of Multi-Drug-Resistant Gonorrhea," Antibiotics, 7, 77 (Aug. 17, (2018).
Papp, J. et al. "Azithromycin Resistance and Decreased Ceftriaxone Susceptibility in Neisseria gonorrhoeae, Hawaii, USA," Emerging Infectious Diseases, vol. 23, No. 5, pp. 830-832 (May 2017).
Bolan, G. et al. "The Emerging Threat of Untreatable Gonococcal Infection," The New England Journal of Medicine; 366; 6, pp. 485-487 (Feb. 9, 2012).
Allan-Blitz, L. et al. "A Cost Analysis of Gyrase A Testing and Targeted Ciprofloxacin Therapy Versus Recommended 2-Drug Therapy for Neisseria gonorrhoeae Infection," Sexually Transmitted Diseases, vol. 45, No. 2 (Feb. 2018).
Magooa, M. et al. "Determination of Neisseria gonorrhoeae susceptibility to ciprofloxacin in clinical specimens from men using a real-time PCR assay," International Journal of Antimicrobial Agents, 42, 63-67 (2013).
Zhao, L. et al. "TaqMan Real-Time Quantitative PCR Assay for Detection of Fluoroquinolone-Resistant Neisseria gonorrhoeae," Curr Microbiol 65: 692-695 (Sep. 2, 2012).
Trembizki, E. et al. "Further evidence to support the individualised treatment of gonorrhoea with ciprofloxacin," Lancet Infect. Dis. 16, 1005-1006 (Sep. 2016).
Global Antibiotic Research and Development Partnership. "Gonorrhea Expert Meeting," Drugs for Neglected Disease Initiative (Jun. 2016), 18 pages.
Dize, L. et al. "Performance of self-collected penile-meatal swabs compared to clinician-collected urethral swabs for the detection of Chlamydia trachomatis, Neisseria gonorrhoeae, Trichomonas vaginalis and Mycoplasma genitalium by Nucleic Acid Amplification Assays," Diagn Microbiol Infect Dis; 86(2): 131-135 (Oct. 2016).
Wheeler, E.K., 'Under-three minute PCR: Probing the limits of fast amplification', published Jul. 27, 2011 by the Royal Society of Chemistry: Analyst 2011 vol. 136 pp. 3707-3712.
Moschou D., et al., 'All-plastic, low-power, disposable, continuous-flow PCR chip with integrated microheaters for rapid DNA amplification', Sensors and Actuators B: Chemical, vol. 199, Aug. 1, 2014, pp. 470-478.

* cited by examiner

Preliminary LoD Determination
of two primary strains of CT, NG, and TV.

SEQUENCE LISTING

<160> NUMBER OF SEQ ID NOS: 23

<210> SEQ ID NO 1
<211> LENGTH: 2751
<212> TYPE: DNA
<213> ORGANISM: Niesseria gonorrhoeae

```
<400> SEQUENCE: 1
atgaccgacg caaccatccg ccacgaccac aaattcgccc tcgaaaccct gcccgtcagc     60
cttgaagacg aaatgcgcaa aagctatctc gactacgcca tgagcgtcat tgtcgggcgc    120
gcgctgccgg acgttcgcga cggcctaaag ccggtgcacc ggcgcgtact gtacgcgatg    180
cacgagctga aaataactg gaatgccgcc tacaaaaaat cggcgcgcat cgtcggcgac    240
gtcatcggta ataccaccc ccacggcgat tccgcagttt acgacaccat cgtccgtatg    300
gcgcaaaatt tcgctatgcg ttatgtgctg atagacggac agggcaactt cggatcggtg    360
gacgggcttg ccgccgcagc catgcgctat accgaaatcc gcatggcgaa aatctcacat    420
gaaatgctgg cagacattga ggaagaaacc gttaatttcg cccgaacta cgacggtagc    480
gaacacgagc cgcttgtact gccgacccgt ttccccacac tgctcgtcaa cggctcgtcc    540
ggtatcgccg tcggtatggc gaccaacatc ccgccgcaca acctcaccga caccatcaac    600
gcctgtctgc gtcttttgga cgaacccaaa ccgaaatcg acgaactgat cgacattatc    660
caagcccccg acttcccgac cggggcaacc atctacggct tgggcggcgt gcgcgaaggc    720
tataaaacag gccgcggccg cgttgttatg cgcggtaaga cccatatcga acccataggc    780
aaaaacggcg aacgcgaacg catcgttatc gacgaaatcc cctatcaggt caacaaagcc    840
aagttggtcg agaaaatcgg cgatttggtt cgggaaaaaa cactggaagg catttccgag    900
ctccgcgacg aatccgacaa atccggtatg cgcgtcgtta tcgagctgaa acgcaacgaa    960
aatgccgaag tcgtcttaaa ccaactctac aaactgactc cgctgcaaga cagtttcggc   1020
atcaatatgg tggttttggt cgacggacaa ccgcgcctgt taaacctgaa acagattctc   1080
tccgaattcc tgcgccaccg ccgcgaagtc gttacccgac gtacgctttt ccggctgaag   1140
aaggcacgcc atgaagggca tatcgccgaa cggaaagccg tcgcactgtc caatatcgat   1200
gaaatcatca agctcatcaa gaatcgccc aacgcggccg aggccaaaga aaaactgctt   1260
gcgcgccctt gggccagcag cctcgttgaa gaaatgctga cgcgttccgg tctggatttg   1320
gaaatgatgc gtccggaagg attggtcgca acattggtc tgaaaaaaca aggttattac   1380
ctgagcgaga ttcaggcaga tgctatttta cgcatgagcc tgcgaaacct gaccggcctc   1440
gatcagaaag aaattatcga aagctacaaa aacctgatgg gtaaaatcat cgactttgtg   1500
gatatcctct ccaaacccga acgcattacc caaatcatcc gtgacgaact ggaagaaatc   1560
aaaaccaact atggcgacga acgccgcagc gaaatcaacc cgttcggcgg cgacattgcc   1620
gatgaagacc tgattccgca acgcgaaatg gtcgtgaccc tgacccacgg cggctatata   1680
aaaacccagc cgaccaccga ctatcaggct cagcgtcgcg gcgggcgcgg caaacaggcg   1740
gctgccacca agacgaaga ctttatcgaa accctgtttg ttgccaacac gcatgactat   1800
ttgatgtgtt ttaccaacct cggcaagtgc cactggatta aggtttacaa actgcccgaa   1860
ggcgacgca acagccgcgg ccgtccgatt aacaacgtca tccagctgga agaaggcgaa   1920
aaagtcagcg cgattctggc agtacgcgag tttcccgaag accaatacgt cttcttcgcc   1980
accgcgcagg gaatggtgaa aaaagtccaa cttttccgcct ttaaaaacgt ccgcgcccaa   2040
ggcattaaag ccatcgcact caagaaggc gactacctcg tcggcgctgc gcaaacaggc   2100
ggtgcggacg acattatgtt gttctccaac ttgggcaaag ccatccgctt caacgaatac   2160
tgggaaaaat ccggcaacga cgaagcggaa gatgccgaca tcgaaaccga gatttcagac   2220
gacctcgaag acgaaaccgc cgacaacgaa aacaccctgc caagcggcaa aaacggcgtg   2280
cgtccgtccg gtcgcggcag cggcggtttg cgcggtatgc gcctgcctgc cgacggcaaa   2340
```

-continued

```
atcgtcagcc tgattacctt cgccctgaa accgaagaaa gcggtttgca agttttaacc    2400
gccaccgcca acggatacgg aaaacgcacc ccgattgccg attacagccg caaaaacaaa    2460
ggcgggcaag gcagtattgc cattaacacc ggcgagcgca acggcgattt ggtcgccgca    2520
accttggtcg gcgaaaccga cgatttgatg ctgattacca gcggcggcgt gcttatccgt    2580
accaaagtcg aacaaatccg cgaaaccggc cgcgccgcag caggcgtgaa actgattaac    2640
ttggacgaag gcgaaaacctt ggtatcgctg aacgtgttg ccgaagacga atccgaactc    2700
tccggcgctt ctgtaatttc caatgtaacc gaaccggaag ccgagaactg a            2751
```

<210> SEQ ID NO 2
<211> LENGTH: 89
<212> TYPE: DNA
<213> ORGANISM: Artificial Sequence
<220> FEATURE:
<223> OTHER INFORMATION: Amplicon (AntiSense)

<400> SEQUENCE: 2

```
cgaaattttg cgccatacgg acgatggtgt cgtaaactgc ggaatcgccg tggggtggt     60 atttaccgat gacgtcgccg acgatgcgc                                      89
```

<210> SEQ ID NO 3
<211> LENGTH: 20
<212> TYPE: DNA
<213> ORGANISM: Artificial Sequence
<220> FEATURE:
<223> OTHER INFORMATION: Seq2 Reverse Primer

<400> SEQUENCE: 3

```
cgaaattttg cgccatacgg                                                20
```

<210> SEQ ID NO 4
<211> LENGTH: 12
<212> TYPE: DNA
<213> ORGANISM: Artificial Sequence
<220> FEATURE:
<223> OTHER INFORMATION: Seq2 Forward Primer

<400> SEQUENCE: 4

```
gcgcatcgtc gg                                                        12
```

<210> SEQ ID NO 5
<211> LENGTH: 15
<212> TYPE: DNA
<213> ORGANISM: Artificial Sequence
<220> FEATURE:
<223> OTHER INFORMATION: Probe for Ciprofloxacin Susceptibility

<400> SEQUENCE: 5

```
cggtgattcc gcagt                                                     15
```

<210> SEQ ID NO 6
<211> LENGTH: 21
<212> TYPE: DNA
<213> ORGANISM: Artificial Sequence
<220> FEATURE:
<223> OTHER INFORMATION: GyrA Positive Control Probe

<400> SEQUENCE: 6

```
tcatcggtaa ataccacccc c                                              21
```

<210> SEQ ID NO 7

```
<211> LENGTH: 108
<212> TYPE: DNA
<213> ORGANISM: Artificial Sequence
<220> FEATURE:
<223> OTHER INFORMATION: gryA amplicon

<400> SEQUENCE: 7
cgcgcatcgt cggcgacgtc atcggtaaat accaccccca cggcgattcc gcagtttacg    60
acaccatcgt ccgtatggcg caaaatttcg ctatgcgtta tgtgctga                108

<210> SEQ ID NO 8
<211> LENGTH: 11
<212> TYPE: DNA
<213> ORGANISM: Artificial Sequence
<220> FEATURE:
<223> OTHER INFORMATION: Forward Primer

<400> SEQUENCE: 8
gcgcatcgtc g                                                         11

<210> SEQ ID NO 9
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<222> LOCATION: (1)..(1)
<223> OTHER INFORMATION: biotin conjugated to the reverse primer via a
      linker

<400> SEQUENCE: 9
tcagcacata acgcatagc                                                 19

<210> SEQ ID NO 10
<211> LENGTH: 34
<212> TYPE: DNA
<213> ORGANISM: Artificial Sequence
<220> FEATURE:
<223> OTHER INFORMATION: gryA amplicon

<400> SEQUENCE: 10
cccccacggc gattccgcag tttacgacac catc                                34

<210> SEQ ID NO 11
<211> LENGTH: 16
<212> TYPE: DNA
<213> ORGANISM: Artificial Sequence
<220> FEATURE:
<223> OTHER INFORMATION: Forward Primer

<400> SEQUENCE: 11
cccccacggc gattcc                                                    16

<210> SEQ ID NO 12
<211> LENGTH: 21
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<222> LOCATION: (1)..(1)
<223> OTHER INFORMATION: biotin conjugated to the reverse primer via a
      linker

<400> SEQUENCE: 12
```
gatggtgtcg taaactgcgg a                                          21

<210> SEQ ID NO 13
<211> LENGTH: 21
<212> TYPE: DNA
<213> ORGANISM: Artificial Sequence
<220> FEATURE:
<223> OTHER INFORMATION: Reverse Primer (reverse complement)

<400> SEQUENCE: 13
tccgcagttt acgacaccat c                                          21

<210> SEQ ID NO 14
<211> LENGTH: 16
<212> TYPE: DNA
<213> ORGANISM: Artificial Sequence
<220> FEATURE:
<223> OTHER INFORMATION: Probe 1
<220> FEATURE:
<221> NAME/KEY: misc_feature
<222> LOCATION: (1)..(1)
<223> OTHER INFORMATION: amine-reactive moeity conjugated to the probe
      via a linker

<400> SEQUENCE: 14
cggcgattcc gcagtt                                                16

<210> SEQ ID NO 15
<211> LENGTH: 15
<212> TYPE: DNA
<213> ORGANISM: Artificial Sequence
<220> FEATURE:
<223> OTHER INFORMATION: Probe 2
<220> FEATURE:
<221> NAME/KEY: misc_feature
<222> LOCATION: (1)..(1)
<223> OTHER INFORMATION: amine-reactive moeity conjugated to the probe
      via a linker

<400> SEQUENCE: 15
cggcgattcc gcagt                                                 15

<210> SEQ ID NO 16
<211> LENGTH: 15
<212> TYPE: DNA
<213> ORGANISM: Artificial Sequence
<220> FEATURE:
<223> OTHER INFORMATION: Probe 3
<220> FEATURE:
<221> NAME/KEY: misc_feature
<222> LOCATION: (1)..(1)
<223> OTHER INFORMATION: amine-reactive moeity conjugated to the probe
      via a linker

<400> SEQUENCE: 16
cggtgattcc gcagt                                                 15

<210> SEQ ID NO 17
<211> LENGTH: 15
<212> TYPE: DNA
<213> ORGANISM: Artificial Sequence
<220> FEATURE:
<223> OTHER INFORMATION: Probe 4
<220> FEATURE:
<221> NAME/KEY: misc_feature
<222> LOCATION: (1)..(1)
<223> OTHER INFORMATION: amine-reactive moeity conjugated to the probe
      via a linker

```
<400> SEQUENCE: 17
cggctattcc gcagt                                                    15

<210> SEQ ID NO 18
<211> LENGTH: 15
<212> TYPE: DNA
<213> ORGANISM: Artificial Sequence
<220> FEATURE:
<223> OTHER INFORMATION: Probe 5
<220> FEATURE:
<221> NAME/KEY: misc_feature
<222> LOCATION: (1)..(1)
<223> OTHER INFORMATION: amine-reactive moeity conjugated to the probe
      via a linker

<400> SEQUENCE: 18
cggcgattcg gcagt                                                    15

<210> SEQ ID NO 19
<211> LENGTH: 19
<212> TYPE: DNA
<213> ORGANISM: Artificial Sequence
<220> FEATURE:
<223> OTHER INFORMATION: Probe 7
<220> FEATURE:
<221> NAME/KEY: misc_feature
<222> LOCATION: (1)..(1)
<223> OTHER INFORMATION: amine-reactive moeity conjugated to the probe
      via a linker

<400> SEQUENCE: 19
cacggctatt ccgcagttt                                                19

<210> SEQ ID NO 20
<211> LENGTH: 19
<212> TYPE: DNA
<213> ORGANISM: Artificial Sequence
<220> FEATURE:
<223> OTHER INFORMATION: Probe 8
<220> FEATURE:
<221> NAME/KEY: misc_feature
<222> LOCATION: (1)..(1)
<223> OTHER INFORMATION: amine-reactive moeity conjugated to the probe
      via a linker

<400> SEQUENCE: 20
tacggctatt ccgcagttt                                                19

<210> SEQ ID NO 21
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<222> LOCATION: (1)..(1)
<223> OTHER INFORMATION: biotin conjugated to the reverse primer via a
      linker

<400> SEQUENCE: 21
gatggtgtcg taaactgcg                                                19

<210> SEQ ID NO 22
<211> LENGTH: 21
<212> TYPE: DNA
<213> ORGANISM: Artificial Sequence
<220> FEATURE:
<223> OTHER INFORMATION: Control Probe
```

```
<400> SEQUENCE: 22
tcatcggtaa ataccacccc c                                              21

<210> SEQ ID NO 23
<211> LENGTH: 68
<212> TYPE: DNA
<213> ORGANISM: Artificial Sequence
<220> FEATURE:
<223> OTHER INFORMATION: gryA amplicon

<400> SEQUENCE: 23
cgcgcatcgt cggcgacgtc atcggtaaat accacccca cggcgattcc gcagtttacg     60
acaccatc                                                             68
```

DEVICES AND METHODS FOR ANTIBIOTIC SUSCEPTIBILITY TESTING

CROSS-REFERENCE TO RELATED APPLICATIONS

This application is a national phase filing under 35 U.S.C. § 371 of International PCT Application No. PCT/US2019/049385, filed Sep. 3, 2019, which claims priority to U.S. Provisional Application Ser. No. 62/820,359, entitled "Devices and Methods for Antibiotic Susceptibility Testing," filed Mar. 19, 2019, and to U.S. Provisional Application Ser. No. 62/726,379, entitled "Devices and Methods for Detecting Single-Nucleotide Polymorphisms," filed Sep. 3, 2018, each of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is VISB_010_02WO_ST25.txt. The text file is 10 KB, created on Jun. 1, 2021, and is being submitted electronically via EFS-Web.

BACKGROUND

The embodiments described herein relate to devices and methods for molecular diagnostic testing. More particularly, the embodiments described herein relate to disposable, self-contained devices and methods for antibiotic susceptibility testing.

A single nucleotide polymorphisms (SNP) is the substitution of a single nucleotide at a particular position in the genome of an organism, observed at some relevant frequency in the population. The observed variant nucleotides at that position are termed alleles. The detection of particular alleles of SNPs has wide utility in medicine. In particular, the detection of particular alleles serve to diagnose the presence or severity of inherited genetic disorders, to personalize treatment for cancer, or for selection of appropriate treatments for infection disease. The devices and methods disclosed herein are applicable to these and other applications of SNP detection.

Diagnosis of drug resistance is an important problem in infectious disease medicine generally. In clinical practice non-genetic methods of drug resistance or sensitivity determination are used, for example as reviewed in Stratton, C W. Advanced Phenotypic Antimicrobial Susceptibility Testing Methods, *Advanced Techniques in Diagnostic Microbiology* (Tang et al, eds., 2018).

The CDC has identified drug resistant *Neisseria gonorrhoeae* (drNG) as an urgent threat, with approximately 20 percent of the roughly 820,000 new *Neisseria gonorrhoeae* (NG) infections each year being antibiotic resistant and thus becoming virtually untreatable. Moreover, the overall number of gonorrhea infections is increasing dramatically. According to a recent U.S. Centers for Disease Control and Prevention (CDC) press release, the yearly increase in gonorrhea diagnoses is over 50 percent. Experts agree that treating patients with the narrowest, but still effective, antibiotic for their infection will slow the development of resistance against extended-spectrum cephalosporins, while extending the utility of older antibiotics. Such treatment, however, requires clinicians to assess drug resistance or sensitivity in real time to inform prescription decisions. Unfortunately, many known tests for sexually transmitted infections (STIs) are lab-based tests that have a sample-to-result-to-patient timeline of 3-5 days. This is a significant problem as many patients are "lost-to-care" before the test result is available, and without treatment, continue to spread the disease. To prevent patients being lost-to-care, many physicians prescribe antibiotics before receiving test results, thus promoting antimicrobial resistance.

Compounding the problem, current lab tests do not provide drug sensitivity information to guide treatment. Even if existing STI lab tests provided drug sensitivity information, the lengthy time-to-result would preclude providing physicians with meaningful, real-time clinical guidance for patient treatment. For example, the agar dilution tests to determine NG antibiotic susceptibility are known to take 48-72 hours. As a result, the standard of care for treatment of NG patients includes treatment with parenteral ceftriaxone (CRO) plus oral azithromycin (AZI), a last resort antibiotic, for all cases of NG, regardless of resistance status. Even though treatment failure with the dual CRO+AZI therapy has yet to be seen in the US, it is a matter of time until resistance to this last line of defense develops, especially given the recent 2018 case of gonorrhea in the UK that was resistant to the recommended dual CRO+AZI regimen.

Thus, a need exists for improved devices and methods for molecular diagnostic testing. In particular, a need exists for a highly sensitive and specific, affordable, point-of-care (POC) diagnostic that provides rapid actionable result to the clinician. Such improved devices and methods would ensure that patients receive the appropriate antibiotic, thereby minimizing the use of broad-spectrum ceftriaxone, lowering the evolutionary selection pressure on last-line antibiotics, and extending the utility of older antibiotics.

SUMMARY

Molecular diagnostic test devices and methods are described herein. In some embodiments, a method includes detecting within a disposable molecular diagnostic test device and from a single urogenital sample, the presence of a pathogen (e.g., NG) and determining whether the infecting strain is susceptible to certain antibiotics. For example, in some embodiments, the method includes determining whether the infecting strain is resistant to three classes of antibiotics—ciprofloxacin, cefixime, or zoliflodacin. In some embodiments, the method includes determining the genotype of the infecting strain—such as, without limitation, WT-gyraseA-Ser91 (ciprofloxacin susceptible) or penA-mosaic-XXXIV (reduced cefixime susceptibility)—and providing, based on the determination, individualized treatment to patients. In this manner, the ineffective use of antibiotics (e.g. ceftriaxone) can be minimized.

In an aspect, the disclosure provides, a molecular diagnostic device, comprising a sample preparation module configured to receive a biological sample, wherein the biological sample comprises a polynucleotide; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele.

In another aspect, the disclosure provides method, comprising a) introducing into any of the molecular diagnostic devices of the disclosure a biological sample from a subject having or suspected of having a disease or disorder characterized by one or more SNPs associated with susceptibility to a treatment, wherein the biological sample comprising a polynucleotide from the subject, b) administering the treatment if the molecular diagnostic device indicates the polynucleotide comprises a SNP locus comprising an allele associated with susceptibility to the treatment.

In another aspect, the disclosure a method, performed in a molecular diagnostic device comprising a sample preparation module configured to receive a biological sample, wherein the biological sample comprises a polynucleotide from a target bacteria; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising amplifying a target amplicon from the polynucleotide from the target bacteria; optionally, amplifying a second target amplicon from the polynucleotide from the target bacteria; reacting the first target amplicon with a first probe to produce a first signal indicating susceptibility of the target bacteria to drug; optionally, reacting the first target amplicon with a second probe to produce a second signal indicating presence of the target bacteria in the biological sample and/or amplification of the target amplicon; and optionally, reacting the second target amplicon with a third probe to produce a third signal indicating presence of the target bacteria in the biological sample and/or amplification of either or both of the first target amplicon and the second target amplicon.

In another aspect, the disclosure provides a method, performed in a molecular diagnostic device comprising a sample preparation module configured to receive a biological sample, wherein the biological sample comprises a polynucleotide from a target bacteria; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising: performing a molecular diagnostic test on the biological sample to determine A) the presence of a target bacteria and B) the presence of the target allele within the target bacteria that confers resistance to a first antibiotic; and administering, based on a result of the molecular diagnostic test, a second antibiotic.

In some embodiments, a molecular diagnostic device includes a sample preparation module configured to receive a biological sample, a reagent module, and an amplification module. The reagent module contains a primer set designed to target a gyrA region. The amplification module includes a reaction volume and a heater. The reaction volume is configured to receive the biological sample and the primer set. The heater is configured to convey thermal energy into the reaction volume to amplify the gyrA region to produce an output containing a target amplicon. The detection module is configured to receive the target amplicon and includes a probe designed to maximize binding to a drug-susceptible portion of the target amplicon while minimizing binding to a drug-resistant portion of the target amplicon.

In some embodiments, the primer set is designed to flank the gyrA 91 locus. In some embodiments, the probe is designed to maximize binding to the gyrA Ser-91 wild type while minimizing binding to variants of the gyrA91 sequence containing a drug resistant single-nucleotide polymorphisms (SNP). Moreover, in some embodiments, the probe is characterized by a thermodynamic fulcrum of about 52° C.

In some embodiments, a method includes amplifying a first gene to produce a first target amplicon associated with a bacterium. A second gene is amplified to produce a second target amplicon associated a drug susceptibility mutation. The method further includes reacting the first target amplicon with a first probe to produce a first signal indicating a presence of the bacteria and reacting the second target amplicon with a second probe to produce a second signal indicating that the bacteria is susceptible to a drug.

In some embodiments, the amplifying the first gene and the amplifying the second gene are performed simultaneously within a stand-alone device. In some embodiments, neither the reacting the first target amplicon nor the reacting the second target amplicon includes producing a melting curve. Similarly stated, the second signal is produced without performing any melting curve analysis.

DETAILED DESCRIPTION

Figure 1:
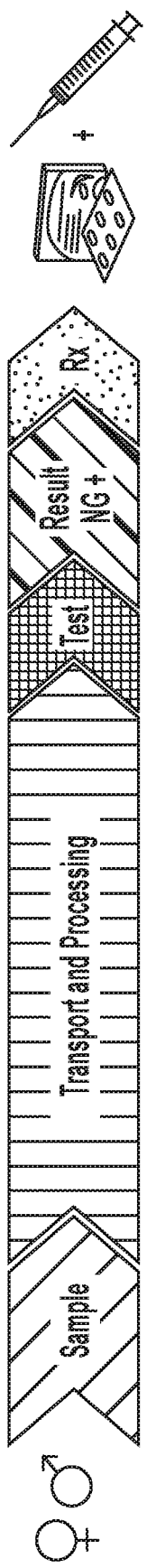
FIG. 1 is a schematic illustration of a method detecting NG, ciprofloxacin-susceptible NG, and/or ceftriaxone-susceptible NG in a combined test, according to an embodiment.
Figure 1:
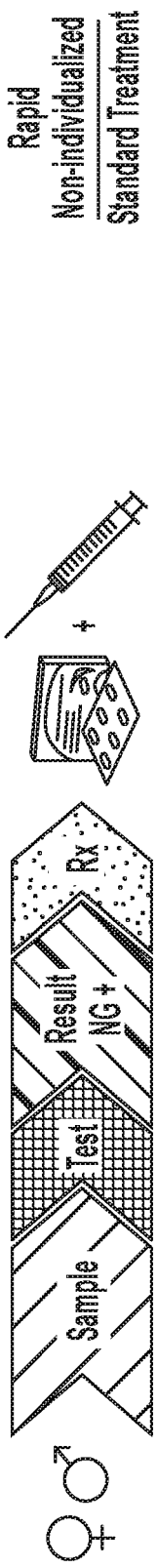
Figure 1:
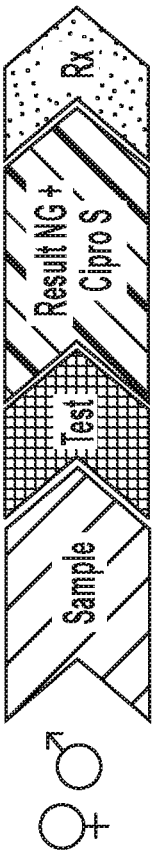

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction, isothermal amplification, or the like), and detection.

As used in this specification and the appended claims, the term "reagent" includes any substance that is used in connection with any of the reactions described herein. For example, a reagent can include an elution buffer, a PCR reagent (e.g., a primer), an enzyme, a substrate, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

The term "nucleic acid molecule," "nucleic acid," or "polynucleotide" may be used interchangeably herein, and may refer to deoxyribonucleic acid (DNA) or ribonucleic acid (RNA), including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA. The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can be derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs. The source of nucleic acid for use in the devices, methods, and compositions described herein can be a biological sample comprising the nucleic acid.

Terms and symbols of nucleic acid chemistry, biochemistry, genetics, and molecular biology used herein follow those of standard treatises and texts in the field, e.g., Komberg and Baker, *DNA Replication*, Second Edition (W. H. Freeman, New York, 1992); Lehninger, Biochemistry, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Polymorphisms, in general, refer to changes of a nucleotide at a single base-pair location on a nucleic acid. A polymorphism means a substitution, inversion, insertion, or deletion of one or more nucleotides at a genetic locus, or a translocation of DNA from one genetic locus to another genetic locus. A "single nucleotide polymorphism" or "SNP" as used herein refers to a substitution of one nucleotide in the polynucleotide sequence of a genome of an organism with respect to a reference sequence (e.g. the wild-type sequence of the organism, or any alternative sequence variant present in a population of organisms of the same species). For example, a SNP in a bacterium is a nucleotide position that differs between representatives of that species; a SNP is a human population is a nucleotide position that differs between representatives between individuals; and a SNP in the context of cancer is a nucleotide position that differs between the genome of the subject and the genome of tumor cells within the subject.

An "allele" refers a particularly nucleotide at the SNP whose detection is desired. When the SNP is in a coding sequence, the allele may encode a change in the protein encoded by the polynucleotide (or "target region"). An "antiallele" refers to nucleotide present at the same position (i.e. the SNP locus) in the reference sequence. In the case of drug-resistance detection, the drug-resistance allele is the nucleotide whose presence in the polynucleotide confers a resistant phenotype on the bacteria. The antiallele refers to a nucleotide that confers a sensitive phenotype on the bacteria. Conversely, in the detection of drug sensitivity, the "allele" is the nucleotide at the SNP locus that covers sensitivity to the drug; the "antiallele" is the nucleotide at the SNP locus of the reference sequence, the same organism having resistance to the drug. When more than two alternative nucleotides are observed at the same position in a sequence (the SNP locus), the "allele" is the nucleotide to be detected, and the two or three alternative nucleotides are "antialleles."

Such SNPs can occur in organisms with highly variable genomes, such as pathogens in general. One of skill will readily understand and identify pathogens in general and those characterized with highly variable genomes. Such pathogens include such as viruses, bacteria, parasites and fungi. The devices and methods described herein are not limited to any particular SNP, as the devices and methods described herein are intended to determine the presence of a various SNPs. SNP can readily be identified in literature in various organisms.

Once an organism is selected, target nucleic acid sequences for the organism, for example a SNP locus, may be determined as being known in the literature or may be determined by sequencing methods (e.g., by comparative analysis of drug-resistant and drug-sensitive organisms). Once a target SNP locus is identified, the 5' and 3' flanking sequences can be identified by retrieving the sequence from any of various public databases (e.g. GenBank) or sequencing the locus anew. A 5' flanking region is a nucleic acid sequence which lies 5' to a target nucleotide position. A 3' flanking region is a nucleic acid sequence which lies 3' to a target nucleotide position. In some cases, the 5' flanking region is immediately adjacent to, or within about 20 bp, 40 bp, 60 bp, 80 bp, or 100 bp of the SNP locus. In some case, the 3' flanking region is immediately adjacent to, or within about 20 bp, 40 bp, 60 bp, 80 bp, or 100 bp of the target nucleotide position. From the sequence information of the target nucleotide (i.e. the allele) at the target nucleotide position (i.e., the SNP locus) and the 5' and 3' flanking regions, a probe including can be designed as described herein.

The term "probe" as used herein refers to an unlabeled oligonucleotide used to capture a target amplicon. Generally the probe is covalently conjugated to a surface of the detection module, although non-covalent conjugated methods may also be employed. An illustrative, non-limiting, means for conjugating a probe to a substrate is a amide coupled. In some embodiments, the surface of the detection module comprises an amorphous polymer (e.g., a cyclic olefin copolymer (COC)). Surface modification of a COC substrate surface can be achieved by oxygen plasma treatment, such as described in Hwang et al. *Surface and Coatings Technology* 202:3669-74 (2008); Gubala et al. *Colloids and Surfaces B: Biointerfaces* 81:544-48 (2010); or Carvalho et al. *ACS Applied Materials and Interfaces* 9:16644-50 (2017). Following activation of the substrate (e.g. a COC substrate) to yield an amine-reactive substrate (e.g. carboxylated COC), amino-modified oligonucleotides can be coupled to the surface by various attachment chemistries including but not limited to acrylic phosphoramidite (Acrydite™), adenylation, azide (NETS ester), I-Linker™ (to aldehyde or ketone-modified substrates), or amino modifiers. A primary amino group can be used to attach the oligonucleotide probes to the surface. Amino modifiers can be positioned at the 5'-end with either a standard (C6) or longer (C12) spacer arm. Amino modifications can also be positioned at the 3'-end. Internal amino modifications can be introduced using an amino-dT base. Illustrative amino modifiers include a 3' amino modifier C6, 3' amino modifier C12, 5' amino modifier C6, and a 5' amino modifier C12.

The devices and methods described herein are not limited to detection of one SNP. Rather, two or more or a plurality of SNP locuses in the same target amplicon may be detected. In some embodiments, a single oligonucleotide probe is designed to specifically bind a probe binding region comprising two or three SNP locuses. In some embodiments, the device includes a detection module having probes against one, two, three, or more sites present on a single target amplicon. In some embodiments, the device is configured to detect SNPs in multiple target amplicons from the same and/or different organisms. In certain embodiments, the device is configured to detect one, two, three, or four SNPs in the same organism. In certain embodiments, the device is configured to detect one, two, three, or four SNPs in the different organisms. For example, and without limitation, in some embodiments, the devices of the disclosure comprise probes for detection of one or more of chlamydia, gonorrhoea, and/or trichomonas. In some embodiments, the probes for each pathogen are specific for a drug-resistance SNP or drug-sensitivity SNP. In some embodiments, the devices of the disclosure further comprises a second probe specific for (e.g., substantially complementary to) a non-overlapping region of the target amplicon. In some embodiments, this second probe serves as a control for the presence of absence of the organism in the biological sample.

"Genetic locus" or "locus" refers to a contiguous sub-region or segment of a genome. As used herein, a "SNP locus" refers the nucleotide position within a genome where a single nucleotide polymorphism occurs. The SNP locus can be named to according to its position within the genome, or by its position in the coding sequence of a protein gene product encoded by the genome of the organism. For example, a SNPs at the gyrA Ser-91 site refers to a SNP at one of the three nucleotide positions in the genome of the organism that correspond to the codon that, during translation of the messenger RNA transcribed from the gyrA gene, directs the ribosome to add a serine as the 91st amino acid in the gyrA gene product.

Target nucleic acid sequences include genomic nucleic acids of a particular organism. Such target nucleic acid sequences may be single stranded or double stranded and may include a sense strand and/or an antisense strand. Such target nucleic acid sequences may be a deoxyribonucleic acid ("DNA") or a ribonucleic acid ("RNA").

As used herein, a "biological sample" refers to any tissue or fluid obtained from an organism (e.g. a subject, e.g. a human or animal subject) that contains a polynucleotide (e.g., DNA or RNA) that can be amplified and/or detected by the devices described herein. In some embodiments, any of the devices and methods described herein can be conducted on a variety of different types of samples. Such sample types can include, for example, vaginal swab, penile meatal swab sample, a buccal swab, stool, sputum, nasal wash, nasal aspirate, throat swab, bronchial lavage, blood, blood cells (e.g. white blood cells), fine needle biopsy samples, peritoneal fluid, visceral fluid, pleural fluid, a urine sample, rectal swab sample and/or pharyngeal swab sample, or cells therefrom. A series of tests was performed with vaginal swab samples. Other biological samples useful in the present invention include tumor samples (e.g. biopsies) and blood samples from subjects having or suspected of having a lymphoproliferative disorder.

In some embodiments, methods of the present disclosure are utilized to detect infections with microorganisms which are potentially resistant to antimicrobial drug treatment. Non-limiting examples of microorganisms include: e.g. one or more of *Acinetobacter, Escherichia*, e.g. *E. coli, Enterobacter, Klebsiella*, e.g. *Klebsiella pneumonia* and/or *Klebsiella oxytoca, Mycobacterium*, e.g. *Mycobacterium tuberculosis, Neisseria*, e.g. *Neisseria meningitides* and/or *Neisseria gonorrhoaea, Proteus*, e.g. *Proteus mirabilis, Pseudomonas*, e.g. *Pseudomonas aeruginosa, Salmonella*, e.g. *Salmonella enterica, Serratia*, e.g. *Serratia marcescens, Staphylococcus*, e.g. *Staphylococcus aureus, Stenotrophomonas*, e.g. *Stenotrophomonas maltophilia, Streptococcus*, e.g. *Streptococcus pneumonia* and/or *Streptococcus pyogenes* and/or *Streptococcus parauberis, Shigella, Haemophilus*, e.g. *Haemophilus influenza, Vibrio*, e.g. *Vibrio harveyi*, and/or *Edwardsiella*, e.g. Edwardsiella *tarda*.

In some embodiments, identification of organisms will define an antimicrobial treatment regime. For example if a Gram-positive organism is determined to the primary pathogen, the patient would receive a gram-positive appropriate antibiotic such as vancomycin. In addition, if the assay determines that a specific organism is present that possesses resistance determinants for a number of antibiotics, these therapeutic options would be avoided for that particular patient.

Non-limiting examples of antimicrobials include β-lactams, β-lactam inhibitors, guinolones and derivatives thereof, e.g. fluoroquinolones, aminoglycosides, glycopeptides, lincosamides, macrolides, nitrofuranes, oxazolidinones, polyketides, respectively tetracyclines, and folate synthesis inhibitors, e.g. benzene derived/sulfonamide antibiotics. According to certain embodiments, the antimicrobial drug, e.g. antibiotic drug, is selected from the group consisting of Amoxicillin/K Clavulanate (AUG), Ampicillin (AM), Aztreonam (AZT), Cefazolin (CFZ), Cefepime (CPE), Cefotaxime (CFT), Ceftazidime (CAZ), Ceftriaxone (CAX), Cefuroxime (CRM), Cephalotin (CF), Ciprofloxacin (CP), Ertapenem (ETP), Gentamicin (GM), Imipenem (IMP), Levofloxacin (LVX), Meropenem (MER), Piperacillin/Tazobactam (P/T), Ampicillin/Sulbactam (A/S), Tetracycline (TE), Tobramycin (TO), and Trimethoprim/Sulfamethoxazole (T/S).

In some embodiments, antimicrobial resistance is identified by detecting SNPs in bacterial genes. The SNP targets represent selected genes known to be associated with bacterial antibiotic resistance bearing mutations in those genes that are deemed determinants of resistance.

In some embodiments, methods of the present disclosure detect one or more bacterial SNPs in genes selected from the group consisting of 16S rRNA, ethA, ndh, 23S rRNA, fabG1, parC, ahpC, folP, parE, alr, gyrA, pncA, embA, gyrB, rlmN, embB, kasA, rpoB, embC, katG, rpsL, vraR, vraS, parC, mtrR, penA, penB, mtrR, ponA, rpsJ, and atpE.

In some embodiments, methods of the present disclosure detect spectinomycin resistance associated with one or more SNPs in the gene encoding mtrR.

In some embodiments, methods of the present disclosure detect penicillin resistance associated with one or more SNPs in the group of genes consisting of bla, penA, ponA, penB, and mtrR.

In some embodiments, methods of the present disclosure detect vancomycin resistance associated with one or more SNPs in vraR and/or vraS.

In some embodiments, methods of the present disclosure are used to detect tetracyclin resistance associated with one or more SNPs in rpsJ, mtrR, and tet(M).

In embodiments, methods of the present disclosure detect cephalosporin resistance associated with one or more SNPs selected from the group consisting of penA, penB, mtrR, and ponA.

In embodiments, methods of the present disclosure are utilized to detect quinolone resistance associated with one or more mutations in gyrA, parC, and mtrR.

In some embodiments, the present disclosure detects azithromycin resistance associated with a SNP in the gene encoding 16S rRNA.

The target nucleic acid sequences may be amplified using methods known to those of skill in the art. Such methods include using a polymerase, primers and nucleotides. "Amplifying" includes the production of copies of a nucleic acid molecule via repeated rounds of primed enzymatic synthesis.

Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391, 544, 6,365,375, 6,294,323, 6,261,797, 6,124,090 and 5,612, 199, or any other nucleic acid amplification method using techniques well known to those of skill in the art. In some embodiments, the methods disclosed herein utilize linear amplification. In some embodiments, the methods disclosed herein utilize PCR amplification.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, reverse transcription (RT)-PCR, nested PCR, quantitative PCR, multiplexed PCR, and the like. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. e.g., "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) Anal. Biochem., 273:221-228. Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., Biotechniques, 26:112-126 (1999); Becker-Andre et al., Nucleic Acids Research, 17:9437-9447 (1989); Zimmerman et al., Biotechniques, 21:268-279 (1996); Diviacco et al., Gene, 122:3013-3020 (1992); Becker-Andre et al., Nucleic Acids Research, 17:9437-9446 (1989); and the like.

"Oligonucleotide" or "polynucleotide," which are used synonymously, means a linear polymer of natural or modified nucleosidic monomers linked by phosphodiester bonds or analogs thereof. Accordingly the oligonucleotide or polynucleotide may be considered a polymer of natural or modified nucleotides. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence (e.g., an oligonucleotide sequence of an oligonucleotide set or a nucleic acid sequence of interest).

The term "primer set" refers one or more primers configured for amplification of a target region of polynucleotide by PCR, or the like. A "target region" refers to a predetermined region in a polynucleotide sequence (e.g., the gene or gene fragment, e.g. a gene or gene fragment associated with resistance or sensitivity to an antibiotic). According to the methods of the disclosure, a target region is selected to include the SNP locus of interest. Amplification of the target region using the primer set results in a "target amplicon." The target amplicon will have the same polynucleotide sequence as the target region (albeit some insertions, deletions, or substitutions of nucleotides due to polymerase errors may occur and the methods of the disclosure are tolerant of such errors), provided that in some cases the primers of the primer set may be substantially complementary but not perfectly complementary to the primer binding site and will therefore introduce changes in the target amplicon. In cases in which the primer set contains no primer overlapping the probe binding site, such substitutions do not impact (or have margin impact) on detection of the target amplicon using probes. In cases where the assay is designed to have overlap between primer binding site and probe binding site, the probe design is generally adapted by designing the probe against the known or predicted target amplicon sequence, rather than against the target region sequence, as in such cases the two are different. A primer set may comprise 1, 2, 3, 4, 5, 6 or more oligonucleotide primers. For example, a single primer may be used for linear amplification (e.g. rolling circle amplification), two primers, one in forward (5'→3') orientation and one in reverse (3'→5') orientation, can be used for PCR amplification. It is understood by those skill in the art that when the polynucleotide is double-stranded (e.g. double-stranded DNA) the designations "forward" and "reverse" are arbitrary. In certain embodiments, 3, 4, or more oligonucleotide primers form the primer set, such as where the molecular diagnostic device is configured to perform a nest PCR reaction.

In some embodiments, the primer set is included in the molecular diagnostic device. For example, the primer set may be provided as a solid (e.g., a lyophilized powder or a table) in the device, or as a liquid (e.g., a solution or suspension provided in the device). The primer set may be provided in a separate reagent chamber, in-line in the flow path, or in another suitable portion of the device. In some embodiments, the molecular diagnostic device does not, prior to use, comprise the primer set. The primer set may be added to the biological sample before the biological sample is add to the device, or the primer set may be introduced into the device before, concurrent with, or after introduction of the biological sample into the device. Thus, in various embodiments, the molecular diagnostic device comprises the primer set, or comprises a reagent module containing a primer set, or is configured to receive a primer set.

As used herein "targeting" (as in a primer set targeting a SNP locus) refers to selection in assay development of primers in the primer set that will result, under operation of the molecular diagnostic device, in the amplification of the polynucleotide (e.g., gene or gene fragment) in the molecular diagnostic device to generate a target amplicon that includes the SNP locus, thereby permitting detection of which allele is present at the SNP locus in the detection module. In some embodiments, the SNP locus is targeted by design of a primer set comprising two or more oligonucleotides (e.g., at least one forward primer and at least one reverse primer). Where one primer (e.g., the forward primer) is upstream (or 5') to the SNP locus, and the other primer (e.g., the reverse primer) is downstream (or 3') to the SNP locus, the primer set is said to "flank" the SNP locus. A primer set may be "designed to flank the SNP locus" by selecting a first primer binding site upstream (or 5') to the SNP locus and a second primer binding site downstream (or 3') to the SNP locus. Primers are designed to be capable of annealing to each of the selected binding sites (e.g., by being substantially complementary to, or complementary to the primer binding site). Using methods well known in the art, primer binding sites and corresponding oligonucleotide primers can be chosen so as to optimize the performance of the amplification reaction.

In some embodiments of the present disclosure, the precise location of the primer binding sites may be changed without adverse impact on the subsequent detection step. In certain embodiments, the present inventors have observed that the length of the resulting target amplicon is, surprisingly, a result-effective variable for the detection step. Thus, in some embodiments, the target region flanked by the primer set is between about 30 base pairs (bp) and about 500 bp, about 30 bp and about 400 bp, about 30 bp and about 300 bp, about 30 bp and about 200 bp, or about 30 bp and about 150 bp. In some embodiments, the target region flanked by the primer set is between about 40 bp and about 500 bp, about 40 bp and about 400 bp, about 40 bp and about 300 bp, about 40 bp and about 200 bp, or about 40 bp and about 150 bp. In some embodiments, the target region flanked by the primer set is between about 50 bp and about 500 bp, about 50 bp and about 400 bp, about 50 bp and about 300 bp, about 50 bp and about 200 bp, or about 50 bp and about 150 bp. In some embodiments, the target region flanked by the primer set is between about 60 bp and about 500 bp, about 60 bp and about 400 bp, about 60 bp and about 300 bp, about 60 bp and about 200 bp, or about 60 bp and about 150 bp. In some embodiments, the target region flanked by the primer set is between about 70 bp and about 500 bp, about 70 bp and about 400 bp, about 70 bp and about 300 bp, about 70 bp and about 200 bp, or about 70 bp and about 150 bp.

In some embodiments, the target amplicon is between about 30 base pairs (bp) and about 500 bp, about 30 bp and about 400 bp, about 30 bp and about 300 bp, about 30 bp and about 200 bp, or about 30 bp and about 150 bp. In some embodiments, the target amplicon is between about 40 bp and about 500 bp, about 40 bp and about 400 bp, about 40 bp and about 300 bp, about 40 bp and about 200 bp, or about 40 bp and about 150 bp. In some embodiments, the target amplicon is between about 50 bp and about 500 bp, about 50 bp and about 400 bp, about 50 bp and about 300 bp, about 50 bp and about 200 bp, or about 50 bp and about 150 bp. In some embodiments, the target amplicon is between about 60 bp and about 500 bp, about 60 bp and about 400 bp, about 60 bp and about 300 bp, about 60 bp and about 200 bp, or about 60 bp and about 150 bp. In some embodiments, the target amplicon is between about 70 bp and about 500 bp, about 70 bp and about 400 bp, about 70 bp and about 300 bp, about 70 bp and about 200 bp, or about 70 bp and about 150 bp.

In some embodiments, the target region flanked by the primer set is about 30 bp, about 40 bp, about 50 bp, about 60 bp, about 70 bp, about 80 bp, about 90 bp, about 100 bp, about 110 bp, about 120 bp, about 130 bp, about 140 bp, about 150 bp, about 160 bp, about 170 bp, about 180 bp, about 190 bp, about 200 bp, about 210 bp, about 220 bp, about 230 bp, about 240 bp, about 250 bp, about 260 bp, about 270 bp, about 280 bp, about 290 bp, or any length therebetween. In some embodiments, the target amplicon is about 30 bp, about 40 bp, about 50 bp, about 60 bp, about 70 bp, about 80 bp, about 90 bp, about 100 bp, about 110 bp, about 120 bp, about 130 bp, about 140 bp, about 150 bp, about 160 bp, about 170 bp, about 180 bp, about 190 bp, about 200 bp, about 210 bp, about 220 bp, about 230 bp, about 240 bp, about 250 bp, about 260 bp, about 270 bp, about 280 bp, about 290 bp, or any length therebetween.

Primers suitable for use in the methods disclosed herein may be designed with the aid of a computer program, such as, for example, DNAWorks, Gene2Oligo, or using the parameters software described herein. Typically, primers are from about 5 to about 500, about 10 to about 100, about 10 to about 50, or about 10 to about 30 nucleotides in length. In certain exemplary embodiments, a set of primers is designed so as to have substantially similar melting temperatures to facilitate manipulation of a complex reaction mixture. The melting temperature may be influenced, for example, by primer length and nucleotide composition.

"Specific" or "specificity" in reference to the binding of one molecule to another molecule, such as a target sequence to a probe, means the recognition, contact, and formation of a stable complex between the two molecules, together with substantially less recognition, contact, or complex formation of that molecule with other molecules.

"Substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid or between an oligonucleotide probe and a probe binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. In some embodiments, probes described herein have 100% complementarity with their corresponding probe binding site. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) Nucl. Acids Res. 12:203.

As used herein, "substantially complementary" includes "complementary." "Complementary" means having 100% sequence identity across the full length of the sequence. I sequence remains "substantially complementary" or "complementary" even if one or more nucleotide positions comprise artificial nucleotides (e.g. locked nucleic acids). For example, the complementary polynucleotide may contain a chemically modified C (such as 5-methylcytosine) in place of an unmodified C.

In any of the embodiments provided herein, the oligonucleotide primer(s) or probe(s) may comprise one or more locked nucleic acids (LNAs). Locked nucleic acids include, without limitation, nucleotide acidic containing a 2' to 4' methylene bridge. In some embodiments provided herein, the DNA nucleotide at the second nucleotide position contains a chemically modified nitrogenous base. In any of the embodiments provided herein, the chemically modified nitrogenous base is 5-methylcytosine. In some, the oligonucleotide comprises at least one nucleotide that is 2'-deoxy, 2' O-alkyl or 2' halo modified. In some, the oligonucleotide has a 5' cap structure, 3' cap structure, or 5' and 3' cap structure. In some embodiments, the oligonucleotide comprises one or more phosphorothioate linkages.

The oligonucleotides of the present invention may comprise one or more locked nucleic acid (LNAs) residues, or "locked nucleotides." The oligonucleotide of the present invention can contain one or more locked nucleic acid (LNAs) residues, or "locked nucleotides." The oligonucleotides of the present invention may comprise one or more nucleotides containing other sugar or base modifications. The terms "locked nucleotide," "locked nucleic acid unit," "locked nucleic acid residue," "LNA" or "LNA unit" may be used interchangeably throughout the disclosure and refer to a bicyclic nucleoside analogue. For instance, suitable oligonucleotide inhibitors can be comprised of one or more "conformationally constrained" or bicyclic sugar nucleoside modifications (BSN) that confer enhanced thermal stability to complexes formed between the oligonucleotide containing BSN and their complementary target strand. LNAs are described, for example, in U.S. Pat. Nos. 6,268,490, 6,316, 198, 6,403,566, 6,770,748, 6,998,484, 6,670,461, and 7,034, 133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. The term "corresponding locked nucleotide" is intended to mean that the nucleotide has been replaced by a locked nucleotide containing the same base.

A "matched" nucleotide refers to a nucleotide that is the Watson-Crick pair of the nucleotide on the opposing strand or binding site of the probe. For example, a probe for a target allele that has an 'A' as the SNP locus is matched to the target allele if the corresponding nucleotide in the probe is a 'T'; and, likewise the probe is matched to 'T' at the SNP locus if the corresponding nucleotide is 'A'; 'G' for 'C'; and 'C' for 'G.' As is known in the art, other nucleotides, including non-natural nucleotides may be used to match the SNP locus.

"Duplex" refers to at least two oligonucleotides and/or polynucleotides that are fully or partially complementary undergo Watson-Crick type base pairing among all or most of their nucleotides so that a stable complex is formed of a sense strand and an antisense strand. The sense strand may be identified as the strand in the 5' to 3' direction in the hybridized duplex while the antisense strand may be identified as the strand in the 3' to 5' direction in the hybridized duplex. The terms "annealing" and "hybridization" are used interchangeably to mean the formation of a stable duplex. Stable duplex means that a duplex structure is not destroyed by a stringent wash, e.g., conditions including temperature of about 5° C. less that the Tm of a strand of the duplex and low monovalent salt concentration, e.g., less than 0.2 M, or less than 0.1 M. "Perfectly matched" or "100% complementarity" in reference to a duplex means that the polynucleotide or oligonucleotide strands making up the duplex form a double stranded structure with one another such that every nucleotide in each strand undergoes Watson-Crick base pairing with a nucleotide in the other strand, i.e. every nucleotide in a shorter strand undergoes Watson-Crick base pairing with a nucleotide in the other longer strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the Tm for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, Molecular Cloning A Laboratory Manual, 2nd Ed. Cold Spring Harbor Press (1989) and Anderson Nucleic Acid Hybridization, 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

A probe according to the present disclosure may be referred to as a hybridization probe which is a fragment of DNA or RNA of variable length which is used in DNA or RNA samples to detect the presence of nucleotide sequences (the target amplicon) that are complementary or substantially complementary to the sequence in the probe. The probe thereby hybridizes to single-stranded nucleic acid (DNA or RNA) whose base sequence allows probe-target base pairing due to complementarity between the probe and target amplicon. The probe is linked to a surface in the detection module by covalent chemical attachment or other methods of associating an oligonucleotide with a substrate as described herein or known in the art.

To detect hybridization of the target amplicon to the probe, the target amplicon is tagged (or "labeled") with a molecular marker or label, for example a fluorescent marker or other detectable moiety such as a radioactive moiety or any enzyme capable of generating a colored or fluorescent signal in the presence of an appropriate enzyme substrate.

Depending on the method, the probe may be synthesized using the phosphoramidite method, or it can be generated and labeled by PCR amplification or cloning. Methods of making nucleic acid probes are known to those of skill in the art.

Visually detectable markers suitable for use in the devices and methods of the disclosure include various enzymes, prosthetic groups, fluorescent markers, luminescent markers, bioluminescent markers, and the like. Examples of suitable fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. Other suitable markers useful for detection of polynucleotides, are known to those of skill in the art.

In some embodiments, the primer sets of the disclosure comprise a detectable moiety, whereby amplification of a target region using the primer set results in production of a tagged target amplicon. In some embodiments, the detectable moiety is a biotin tag. Either forward primer, reverse primer, or both forward and reverse primers may be biotinylation. In some embodiments, one or both primers is biotin-tagged. After hybridization of the target amplicon to a probe, detection proceeds by introducing into the detection module of a first reagent, the first reagent comprising a biotin-labeled marker (e.g. a fluorescent marker or an enzyme system) is provided. In some embodiments, the first reagent comprises streptavidin-tagged horse radish peroxidase (HRP). After optionally removing excess of the first agent by washing the detection chamber, a second reagent may be provided. In some embodiments, the second reagent is substrate for a peroxidase (e.g. HRP)

The substrate can include, for example, any of tetramethylbenzidine (TMB), 3-ethylbenzothiazoline-6-sulfonic acid, o-phenylenediamine, Amplex Red, homovanillic acid, 3,3'-diaminobenzidine, 3-amino-9-ethylcarbazole, 5-Bromo-4-chloro-3-indolyl phosphate, 5-Bromo-4-chloro-3-indolyl phosphate/nitro blue tetrazolium, Fast Red (Sigma). In some embodiments, the substrate is TMB. In such embodiments, TMB in the detection module 2800 changes color from colorless to blue, and finally yellow above any positive chambers. The yellow color is produced when the detection module 2800 is heated to about 40° C. during the detection operation. In contrast, some ELISA based formats produce a color change that goes to blue or green, and does not proceed to yellow until it is exposed to a stop solution.

In other embodiments, the substrate of the substrate is a precipitating substrate formulated to catalyze the production of the visible signal OP by producing an insoluble colored product when the substrate is in contact with the enzyme. Such precipitating substrates can include, for example, TMB (3,3',5,5' tetramethylbenzidine), DAB (3,3' diaminobenzidine), or 4 CN (4-chloro-1-napthol) based membrane substrates for horseradish peroxidase enzymes, or BCIP (5-bromo-4-chloro-3-indolyl-phosphate) based membrane substrates for alkaline phosphatase. In some embodiments, the precipitating substrate can be the BioFX® TMB HRP Membrane Substrates produced by Surmodics. In some embodiments, the precipitating substrate can maintain stability when stored for up to one year in a liquid form at room temperature. In other embodiments, the precipitating substrate can maintain stability when stored for up to two years in a liquid form at room temperature. Moreover, such precipitating substrates can produce a dark color, which can be easier to visualize and interpret. In some embodiments, the precipitating substrate can produce a colorimetric output that persists for at least one hour, at least two hours, at least three hours, at least 12 hours, at least 24 hours, or at least 48 hours. Further illustrative detection methods are providing in International Patent Publication No. WO2018005710A1, which is incorporated herein by reference in its entirety.

Methods for incorporating detectable labels into nucleic acids are well known. Typically, detectable labels (e.g., as hapten- or fluorochrome-conjugated deoxyribonucleotides) are incorporated into a nucleic acid during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

Detection method(s) used will depend on the particular detectable labels used in the nucleic acid probes. In certain exemplary embodiments, labels may be detected by a microscope, a spectrophotometer, a tube luminometer, x-ray film, a scintillator, or the like.

Methods described herein are useful in determining the presence of organisms having one or more polymorphisms within a population of organisms which include wild type organisms or organisms without the one or more polymorphisms. Organisms within the scope of the present disclosure include viruses, bacteria and fungi. Exemplary viruses include Influenza viruses, Hepatitis C virus, Dengue virus, West Nile virus, Ebola virus, Lassa virus and the like. One of skill will readily understand that this list is non-limiting and that other viruses are well known to and can be readily identified by those of skill in the art. Exemplary bacteria include *Staphylococcus aureus*/methicillin-resistant *S. aureus, Neisseria meningitides, Mycobacterium tuberculosis, Borrelia species, Streptococcus Pneumoniae, Chlamydia Trachomatis, Neisseria Gonorrhoeae* and the like. One of skill will readily understand that this list is exemplary only and that other bacteria are well known to and can be readily identified by those of skill in the art. Exemplary fungi include *Candida* species, *Aspergillus* species, *Histoplasma capsulatum, Cryptococcus neoformans, Cryptococcus gattii, Coccidioides immitis* and the like. One of skill will readily understand that this list is exemplary only and that other fungi are well known to and can be readily identified by those of skill in the art.

"Kit" refers to any system, materials or reagents for carrying out a method of the present disclosure. In the context of method described herein, a kit for identifying a particular polymorphism within a population of particular organisms may include assays, reaction reagents (e.g., primers, enzymes, etc. in the appropriate containers) and/or supporting materials (e.g., buffers, written instructions for performing the assay etc.). For example, kits include one or more enclosures (e.g., boxes) containing the relevant reaction reagents and/or supporting materials for assays or methods of the invention. Such contents may be delivered to the intended recipient together or separately. For example, a first container may contain an enzyme for use in an assay, while a second container contains primers.

"Complementary" to an allele means that the sequence of the oligonucleotide comprises a nucleotide capable of Watson-Crick pairing with the allele. When the primer binding site is on the antisense strand of the SNP locus The terms "melting temperature," abbreviated $T_m$, refers to the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m=81.5+0.41$ (% G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, H. T. & Santa Lucia, J., Jr., *Biochemistry* 36, 10581-94 (1997)) include alternative methods of computation which take structural and environmental, as well as sequence characteristics into account for the calculation of $T_m$. DNASoftware™ Visual OMP™ is a software for designing primers and probes that may be used to calculate $T_m$, e.g. assuming a concentration of monovalent ions of 0.1 M and a concentration of magnesium ions of 0.003 M. The melting temperature of a target amplicon is defined as the calculated melting temperature of an oligonucleotide spanning the entire amplicon—that is, the melting temperature of the complete product of amplification using flanking oligonucleotide primers.

As used herein, "thermodynamic fulcrum" refers to the temperature of fluid in a flow cell at which enough binding of amplicon to capture probe binding occurs to produce signal from the flow cell detectable by eye using colorimetric detection with TMB. For example, the signal intensity from a flow cell at a temperature above the thermodynamic fulcrum may be at least 10%, 50%, 100%, or 200% brighter than the signal from a flow cell at 5° C. or more below thermodynamic fulcrum. The signal intensity from a flow cell at a temperature above the thermodynamic fulcrum may be at least 10%, 50%, 100%, or 200% brighter than the signal from a flow cell a detection surface lacking the probe. Generally, the thermodynamic fulcrum of a probe is at least about 10° C., 9° C., 8° C., 7° C., 6° C., 5° C., or 4° C. lower than calculated probe $T_m$ of the probe. The thermodynamic fulcrum may be determined experimentally.

Unless indicated otherwise, the terms apparatus, diagnostic apparatus, diagnostic system, diagnostic test, diagnostic test system, test unit, and variants thereof, can be interchangeably used.

Figure 2:
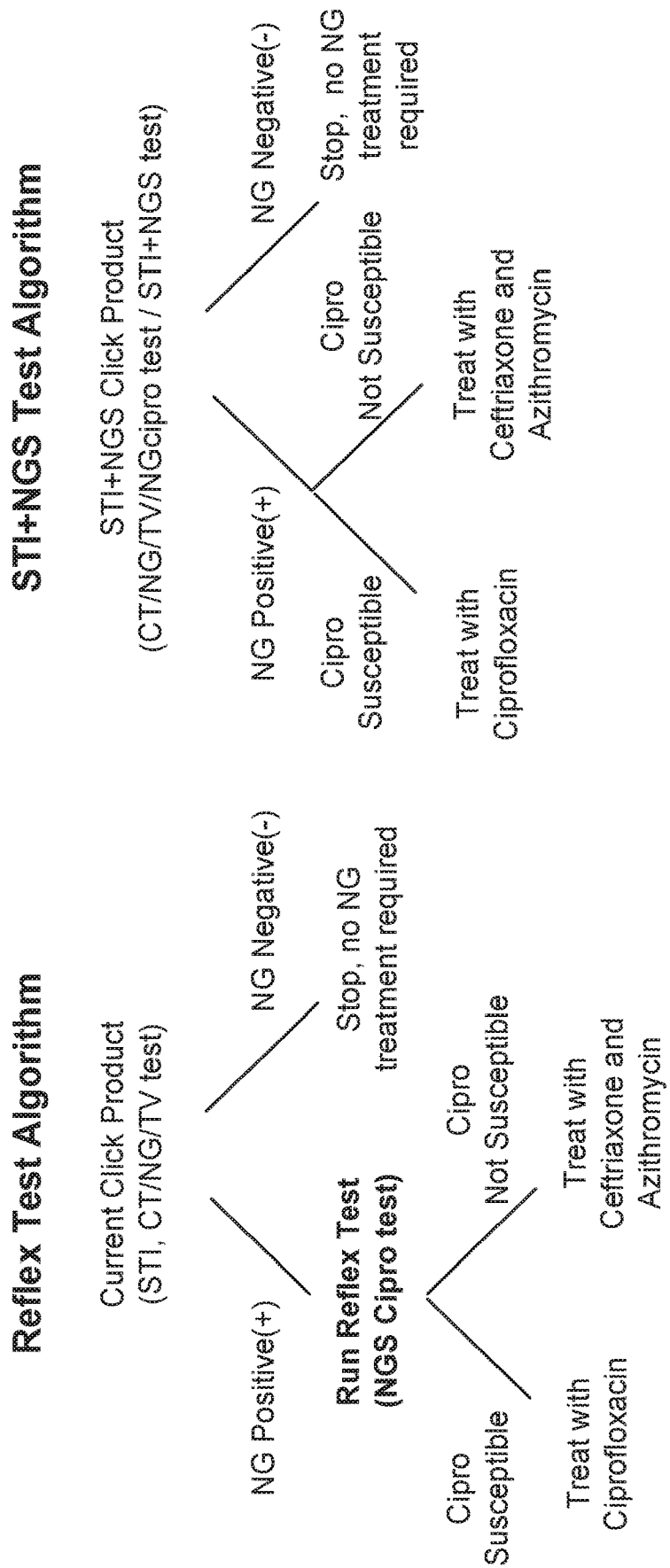
FIG. 2 is a flow chart showing a comparison between current testing methods, which require a reflex test, and a combined test, according to an embodiment.

In some embodiments, a method includes detecting NG, ciprofloxacin-susceptible NG, and/or ceftriaxone-susceptible NG in a combined test. By providing a personalized test via a single test operation (i.e., without the need for one or more follow up or "reflex" tests), patient outcomes can be improved while reducing the proliferation of AMR NG strains. A "negative" NG test eliminates the presumptive prescription of unnecessary antibiotics. A "positive" NG test indicating ciprofloxacin sensitivity reduces the prescription of last resort ceftriaxone. FIG. 1 shows a schematic illustration of the reduced time and improvement associated with such a personalized (or individualized) test. FIG. 2 shows a comparison between current testing methods, which require a reflex test, and a combined test, according to an embodiment. For example, as described above, known tests often result in a parenteral antibiotic.

In some embodiments, a method includes performing a molecular diagnostic test on a biological sample to determine A) the presence of a target bacteria and B) the presence of a gene mutation within the target bacteria that confers resistance to a first antibiotic. Based on a result of the molecular diagnostic test, either the first antibiotic or a second antibiotic is prescribed. For example, in some embodiments, the target bacteria is NG and the first antibiotic is ciprofloxacin. If the test result shows that the NG is susceptible to treatment by ciprofloxacin, then a prescription for ciprofloxacin is provided. In this manner, certain classes of antibiotics (e.g., ciprofloxacin) which are no longer being used to treat NG, can be re-introduced into the treatment protocol. If, however, the test indicates that the NG is resistant to ciprofloxacin, then a second antibiotic, such as, a cephalosporin, is prescribed. Specifically, a "negative" NG test eliminates the presumptive prescription of unnecessary antibiotics. A "positive" NG test indicating ciprofloxacin sensitivity reduces the prescription of last resort ceftriaxone. Identifying susceptibility to oral ciprofloxacin will minimize the use of broad-spectrum ceftriaxone, providing personalized treatments while lowering the evolutionary selection pressure on last-line antibiotics and extending the utility of older antibiotics.

The methods described herein can be performed on any suitable molecular diagnostic device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005870, entitled "Devices and Methods for Detection of Molecules Using a Flow Cell," International Patent Application No. PCT/US17/40112, entitled "Devices and Methods for Nucleic Acid Extraction," and International Patent Publication No. WO2019/060117, entitled "Portable Molecular Diagnostic Test Device and Methods for the Detection of Target Viruses," each of which is incorporated herein by reference in its entirety.

Figure 8:
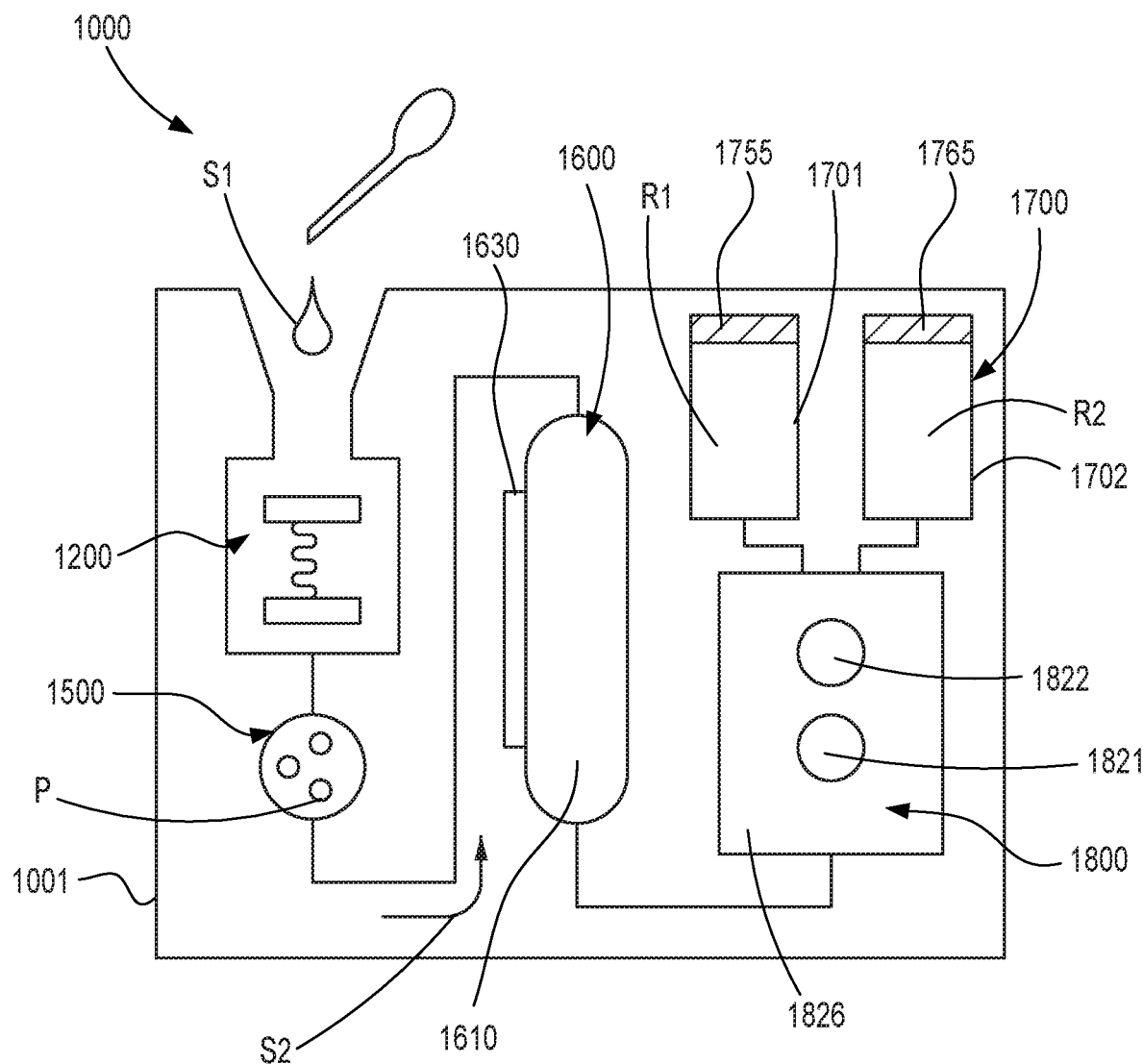
FIGS. 8-10 are schematic illustrations of a molecular diagnostic test device configured to detect a single nucleotide polymorphism (SNP), according to an embodiment, in a first configuration, a second configuration, and a third configuration, respectively
Figure 9:
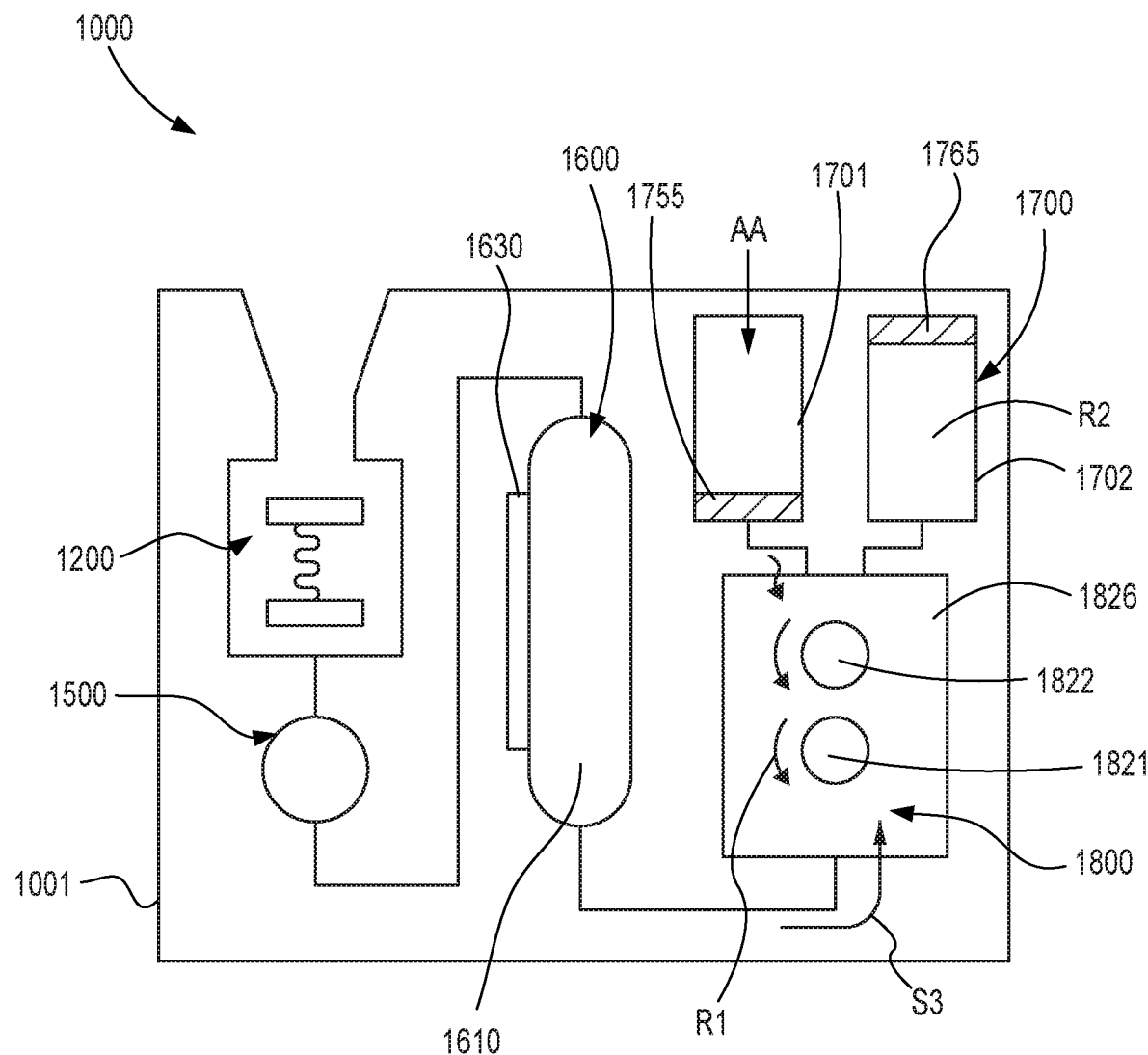
Figure 10:
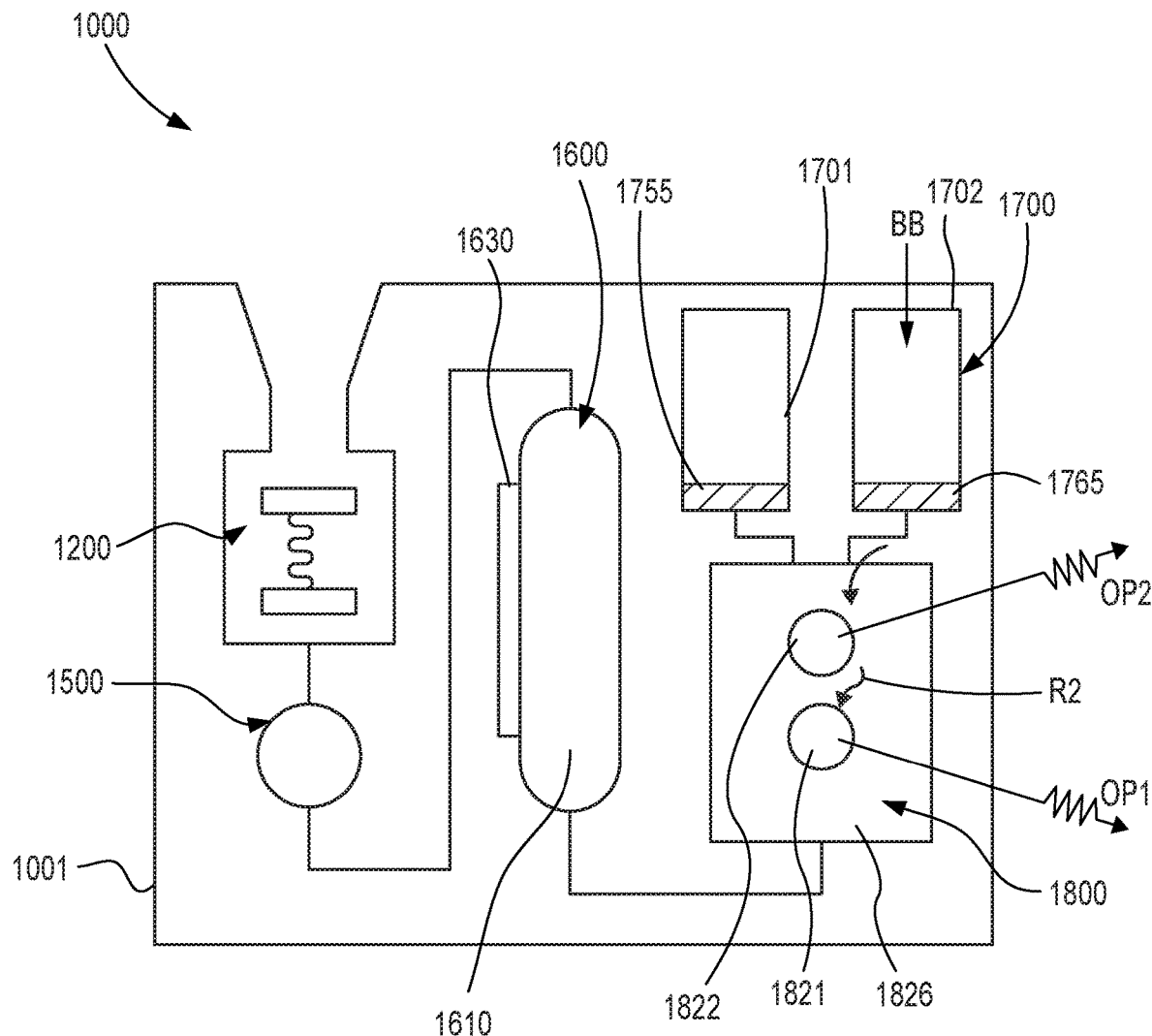

FIGS. 8-10 are schematic illustrations of a molecular diagnostic test device 1000 (also referred to as a "test device" or "device"), according to an embodiment. The test device 1000 contains a primer set targeting a single nucleotide polymorphism (SNP) locus in the polynucleotide and is configured to manipulate a biological sample to produce one or more output signals associated with the SNP, according to any of the methods described herein. In some embodiments, the test device 1000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 1000 can have a size, shape and/or weight such that the device 1000 can be carried, held, used and/or manipulated in a user's hands (i.e., it can be a "handheld" device). In some embodiments, the test device 1000 can be a self-contained, single-use device.

In some embodiments, the device 1000 (and any of the devices shown and described herein) can be a CLIA-waived device and/or can operate in accordance with methods that are CLIA waived. Similarly stated, in some embodiments, the device 1000 (and any of the other devices shown and described herein) is configured to be operated in a sufficiently simple manner and can produce results with sufficient accuracy to pose a limited likelihood of misuse and/or to pose a limited risk of harm if used improperly. In some embodiments, the device 1000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 1000 can be configured for long term storage in a manner that poses a limited likelihood of misuse (spoilage of the reagent(s), expiration of the reagents(s), leakage of the reagent(s), or the like). In some embodiments, the molecular diagnostic test device 1000 is configured to be stored for up to about 16 months, up to about 12 months, up to about 28 months, up to about 24 months, up to about 20 months, up to about 18 months, up to 12 months, up to 6 months, or any values there between.

The test device 1000 includes a housing 1001, a sample preparation module 1200 (also referred to as a sample staging module), an amplification reagent module 1500, an amplification module 1600, a detection reagent module 1700, and a detection module 1800. In some embodiments, the test device 1000 can include any other components or modules described herein, such as, for example, a valve (e.g., to control flow of reagents and/or sample, such as the valve 4340), a fluid transfer module (e.g., the fluid transfer module 4400), and/or an electronic control module (e.g., the electronic control module 4950). The housing 1001 can be any structure within which the sample preparation module 1200 or other components are contained (or partially contained) to form an integrated device for sample preparation and/or molecular testing.

The sample preparation module 1200 defines a sample input volume that receives a biological sample S1. The sample preparation module 1200 can include any components as described herein to manipulate the biological sample S1 for further diagnostic testing and/or to produce a solution for detection of a nucleic acid. For example, in some embodiments, the sample preparation module 1200 can include one or more heaters, one or more chambers within which the biological sample S1 can be manipulated, one or more mixing chambers, and/or certain on-board reagents (e.g., a lysing buffer, an RT enzyme, a control organism, or the like). In some embodiments, the sample preparation module 1200 is configured to extract nucleic acid molecules from the biological sample S1 and can produce, along with the amplification reagent module 1500, an input solution S2 (see FIG. 8) that is conveyed into the amplification module 1600.

The amplification reagent module 1500 is fluidically coupled to the sample preparation module 1200 and contains the desired amplification reagents to facilitate the desired amplification according to any of the methods described herein. As shown in FIG. 8, the amplification reagent module 1500 contains a primer set P targeting a single nucleotide polymorphism (SNP) locus in a polynucleotide of the biological sample S1. The SNP primer set P can include any of the SNP primer sets shown and described herein. The primer set P targets the SNP locus (e.g., by flanking the SNP locus). In addition to the SNP primer set P, the amplification reagent module 1500 can include any other suitable amplification reagents, such as additional primers, nucleotides (e.g., dNTPs), and the DNA polymerase. In RT-PCR applications (e.g., for viral pathogens), the amplification reagent module 1500 may contain a reverse transcriptase. Because the device 1000 is configured for single-use in a point-of-care setting, the amplification reagents can be formulated for and/or packaged within the amplification reagent module 1500 to enhance long term storage. Accordingly, in some embodiments, the SNP primer set P and other amplification reagents can be formulated to have a shelf life of up to about 36 months, up to about 32 months, up to about 26 months, up to about 24 months, up to about 20 months, up to about 18 months, or any values therebetween. For example, in some embodiments, the SNP primer set P can be in the form of a lyophilized pellet or bead.

In some embodiments, the amplification reagent module 1500 can be fluidically coupled to and can convey the SNP primer set P into the sample preparation module 1200 (e.g., for mixing, reconstitution, etc.). In other embodiments, the amplification reagent module 1500 can be configured to receive an output from the sample preparation module 1200 and mix the output with the SNP primer set P and other amplification reagents. In such embodiments, the amplification reagent module 1500 can be configured to hydrate and/or reconstitute the lyophilized beads in a given input volume, while ensuring even local concentrations of reagents in the entirety of the volume. The amplification reagent module 1500 can include any suitable mechanism for producing the desired solution, such as, for example, a continuous flow mixing channel, an active mixing element (e.g., a stir rod) and/or a vibratory mixing element. The mixed sample (referred to as an amplification solution S2) is then conveyed to the amplification module 1600.

The amplification module 1600 includes a flow member 1610 and a heater 1630. The flow member (which functions as a reaction volume) 1610 can be any suitable structure that defines a volume or a series of volumes within which the amplification solution S2 can flow and/or be maintained to amplify the target nucleic acid molecules therein to produce an output detection solution S3 that contains a target amplicon to be detected. The heater 1630 can be any suitable heater or group of heaters coupled to the flow member 1610 that can heat the amplification solution S2 within the flow member 1610 to perform any of the amplification operations as described herein. For example, in some embodiments, the amplification module 1600 (or any of the amplification modules described herein) can be similar to the amplification modules shown and described in U.S. Patent Publication No. 2017/0304829, entitled "Printed Circuit Board Heater for an Amplification Module," which is incorporated herein by reference in its entirety. In other embodiments, the amplification module 1600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety.

In some embodiments, the flow member 1610 defines a single volume within which the amplification solution S2 is maintained and heated to amplify the nucleic acid molecules thereby producing the detection solution S2. In other embodiments, the flow member 1610 can define a "switchback" or serpentine flow path through which the amplification solution S2 flows. Similarly stated, in some embodiments, the flow member 1610 defines a flow path that is curved such that the flow path intersects the heater 1630 at multiple locations. In this manner, the amplification module 1600 can perform a "flow through" amplification reaction where the amplification solution S2 flows through multiple different temperature regions.

The heater 1630 can be any suitable heater or collection of heaters that can perform the functions described herein to amplify the prepared solution. In some embodiments, the heater 1630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 40 cycles). The heater 1630 (and any of the heaters described herein) can be of any suitable design. For example, in some embodiments, the heater 1630 can be a resistance heater, a thermoelectric device (e.g. a Peltier device), or the like. In some embodiments, the heater 1630 can be one or more linear "strip heaters" arranged such that the flow path crosses the heaters at multiple different points. In other embodiments, the heater 1630 can be one or more curved heaters having a geometry that corresponds to that of the flow member 1610 to produce multiple different temperature zones in the flow path.

Although the amplification module 1600 is generally described as performing a thermal cycling operation on the amplification solution S2, in other embodiments, the amplification module 1600 (and any of the amplification modules described herein) can perform any suitable thermal reaction to amplify nucleic acids within the solution. In some embodiments, the amplification module 1600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

The detection reagent module 1700 is disposed within the housing 1001 and includes a first reagent container 1701, a first reagent actuator 1755, a second reagent container 1702, and a second reagent actuator 1765. The detection reagent module 1700 provides on-board storage of a first reagent R1 (within the first reagent container 1701) and a second reagent R2 (within the second reagent container 1702) used in connection with the molecular diagnostic tests described herein. In some embodiments, the first reagent R1 is sealed within the first reagent container 1701 and the second reagent R2 is sealed within the second reagent container 1702. In some embodiments, the detection reagent module 1700 can include one or more puncturers that, upon device actuation, can release the reagents for use.

The first reagent R1 is a detection reagent formulated to facilitate production of a signal that indicates a presence of a target amplicon (e.g., a from the amplified solution S3). In some embodiments, the first reagent R1 comprises streptavidin-tagged horse radish peroxidase (HRP) of the compositions shown and described herein. The second reagent R2 is a substrate formulated to produce an output signal (e.g., OP1, OP2) when catalyzed by the first reagent R1. For example, in some embodiments, the second reagent R2 can be a substrate (e.g., a precipitating substrate) of the types shown and described herein. The detection module 1800 is configured to react the amplified solution S3 from the amplification module 1600 with the first reagent R1 and the second reagent R2 to produce one or more signals (or outputs) OP1, OP2 to indicate presence or absence of a target organism and/or presence or absence of a target allele at a SNP locus in the genome of a target organism in the biological sample S1. Specifically, the detection module 1800 defines a detection channel and includes a first detection surface 1821 and a second detection surface 1822 within the detection channel. The first detection surface 1821 includes a first probe linked to said first detection surface 1821 to permit annealing or hybridization of a target amplicon with sufficient specificity to permit detection of the presence (or absence) of a target amplicon if the allele is present (or absent) in an allele-specific manner. The second detection surface 1822 includes a second probe linked to said second detection surface 1822 to permit annealing or hybridization of a target amplicon with sufficient specificity to permit detection of the presence (or absence) of the target amplicon, regardless of the presence (or absence) of the allele at the SNP locus. The detection module 1800 also includes non-detection surfaces 1826 that are adjacent to, surround, or contact either or both of the first detection surface 1821 and the second detection surface 1822. The non-detection surfaces 1826 can provide a background region that can enhance the overall accuracy detection of the output signals from the device 1000. Although the first detection surface 1821 and the second detection surface 1822 are shown and described as having defined positions within the detection module 1800, in other embodiments, a detection module can include any number of detection surfaces in any desired order or spatial position within the module. Similarly stated, in other embodiments, the first detection surface 1821 and the second detection surface 1822 can be configured to permit detection of the presence or absence of any of the target amplicons as described herein. Moreover, in some embodiments, the detection module 1800 can include additional detection surfaces for controls, additional targets, or the like.

The detection channel is in (or can be placed in) fluid communication with each of the amplification module 1600 and the detection reagent module 1700. In this manner, the amplification solution S3 containing the target amplicon can be conveyed into the detection channel and across the detection surfaces 1821, 1822. Additionally, as shown in FIG. 9, the first reagent R1 can also be conveyed into the detection channel and across the detection surfaces 1821, 1822. The detection surfaces 1821, 1822 include a series of capture probes to which the target amplicon can be bound when the amplification solution S3 flows across the detection surfaces 1821, 1822. The probes can be any suitable probe of the types described herein, e.g., formulated to capture or bind to the target amplicon.

The first reagent R1 can be conveyed by moving the first reagent actuator 1755 as shown by the arrow AA. The first reagent can flow across the detection surfaces, as shown. When the first reagent R1 (i.e., detection reagent) is conveyed into the detection channel, it binds to the captured amplicon. In some embodiments, the detection module 1700 includes a heater (not shown in FIGS. 3-5) configured to incubate the detection reagent R1 within the detection channel in the presence of the captured amplicon to facilitate binding. In some embodiments, the heater can be controlled to maintain the temperature of the detection module 1700 to within about 5° C. of the melting temperature of the capture probe. In other embodiments, the heater can be controlled to maintain the temperature of the detection module 1700 to within about 10° C. or about 15° C. of the melting temperature of the capture probe. In this manner, detection of an allele at a SNP locus can be achieved with sufficient sensitivity and specificity to permit testing and therapeutic intervention at the point-of-care. The present inventors have determined that computational prediction of melting temperature, while a guide to probe design, is not alone sufficient to accurately determine the optimal probe design. Without being bound by theory, it is believed that melting temperature calculations assume polynucleotides interacting in solution, whereas here the probe is linked to the surface of the detection module. Experimental screening of candidate probes is required to achieve the desired operation characteristics. Illustrative methods for such screening are provided in the examples of the present disclosure. In particular, microtiter plate assays can be used to select and optimize probe design prior to construction of a molecular diagnostic device according to the present disclosure.

The second reagent R2 can be conveyed by moving the second reagent actuator 1765 as shown by the arrow BB. When the second reagent R2 reacts with captured amplicon and the bound detection reagent, the first signal OP1 is produced from the first detection surface 1821 and the second signal OP2 is produced from the second detection surface 1822.

Although not shown in FIG. 8-10, in some embodiments, the detection reagent module 1700 can contain any other suitable reagents to facilitate detection of the target SNP according to any of the methods described herein. For example, in some embodiments, the detection reagent module 1700 can include a wash solution comprises one or more buffers, ionic compounds, excipients, detergents, preservatives, or blocking reagents. In some embodiments, the wash solution can be conveyed into the detection channel to remove unbound PCR products and/or any remaining solution. In some embodiments, the wash buffer comprises phosphate buffered saline (PBS), potassium chloride (KCl), magnesium chloride ($MgCl_2$), PROCLIN300™, and/or polysorbate 20 (TWEEN® 20). Optionally, the wash buffer further comprises a blocking agent (e.g., bovine serum albumin (BSA). In certain embodiments, the wash buffer comprises about 0.5×, about 1.0×, or about 1.5×PBS, where 1.0×PBS has a final concentration of 137 mM NaCl, 10 mM Phosphate, 2.7 mM KCl, and a pH of about 7.4. In some embodiments, the wash buffer comprises (in addition to any KCl in the PBS) about 50 mM, about 60 mM, about 70 mM, about 80 mM, about 90 mM, about 100 mM, about 110 mM, or about 120 mM KCl. In some embodiments, the wash buffer comprises (in addition to any KCl in the PBS) about 60 mM to about 90 mM, about 70 mM to about 80 nM, or about 75 mM KCl. In some embodiments, the wash buffer comprises about 0.5 mM to about 10 mM $MgCl_2$, about 1 mM to about 7.5 mM $MgCl_2$, about 1 mM to about 5 mM $MgCl_2$, about 1 mM to about 4 mM $MgCl_2$, about 1 mM to about 3 mM $MgCl_2$, or about 1 mM to about 2 mM $MgCl_2$. In some embodiments, the wash buffer comprises about 1 mM, about 1.5 mM, about 2 mM, about 2.5 mM about 3 mM, about 3.5 mM, or about 4.0 mM $MgCl_2$. In certain embodiments, the wash buffer comprises 1×PBS, about 70 mM to about 80 mM KCl, about 1 mM to about 3 mM $MgCl_2$, about 0.01% (v/v) to about 0.5% (v/v) polysorbate 20 at a pH of about 7.0 to about 7.5 (or pH about 7.4), and optionally a preservative (e.g. 0.03% (v/v) PROCLIN300™). Without limiting the disclosure to any particular wash buffer, the present inventors have surprisingly discovered that in some cases the wash buffers of the disclosure provide increased sensitivity and/or specificity for the apparatuses and methods of the disclosure.

Figure 12:
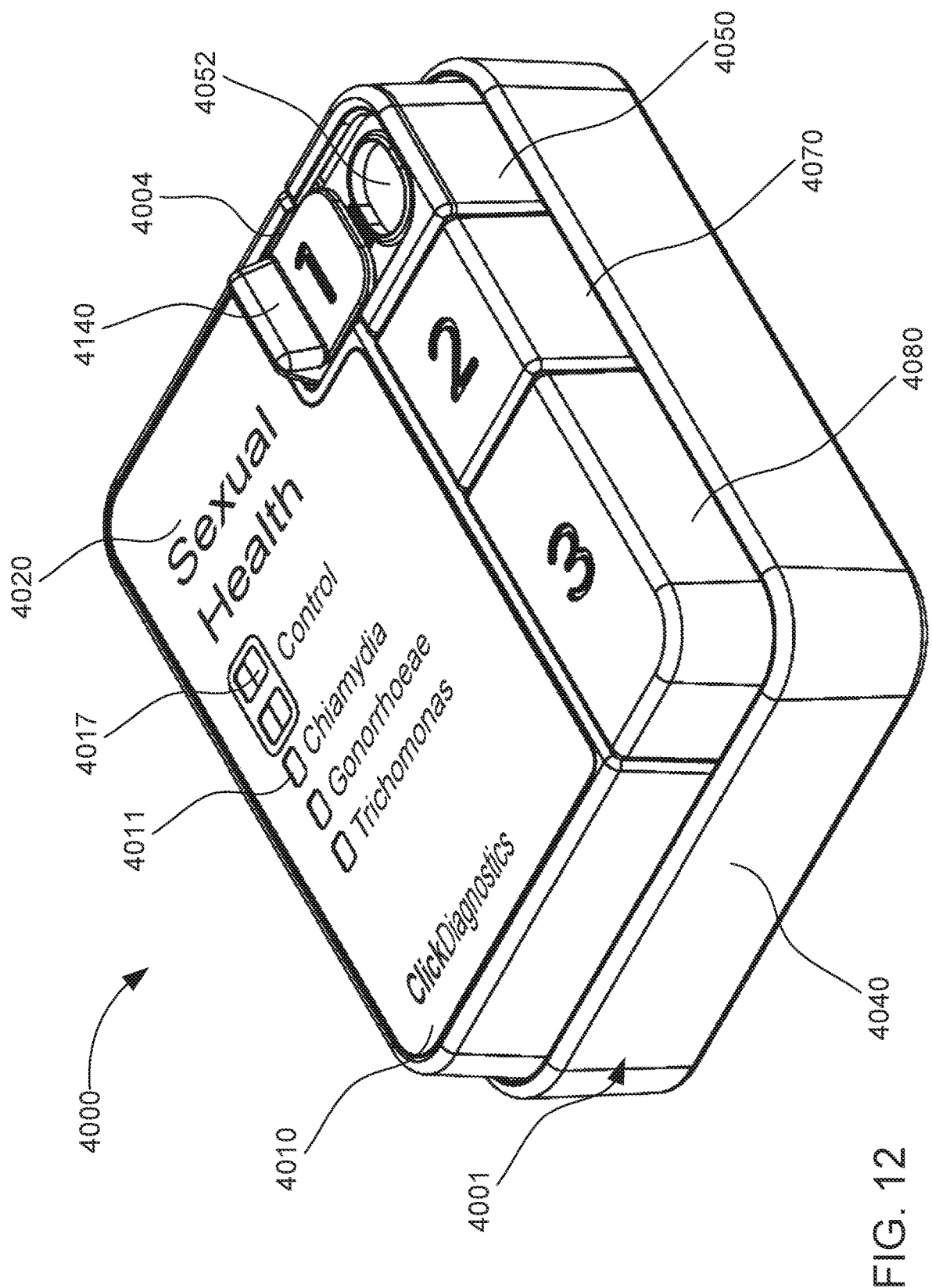
FIGS. 12 and 13 are a perspective view and a top view, respectively, of a molecular diagnostic test device, according to an embodiment.
Figure 13:
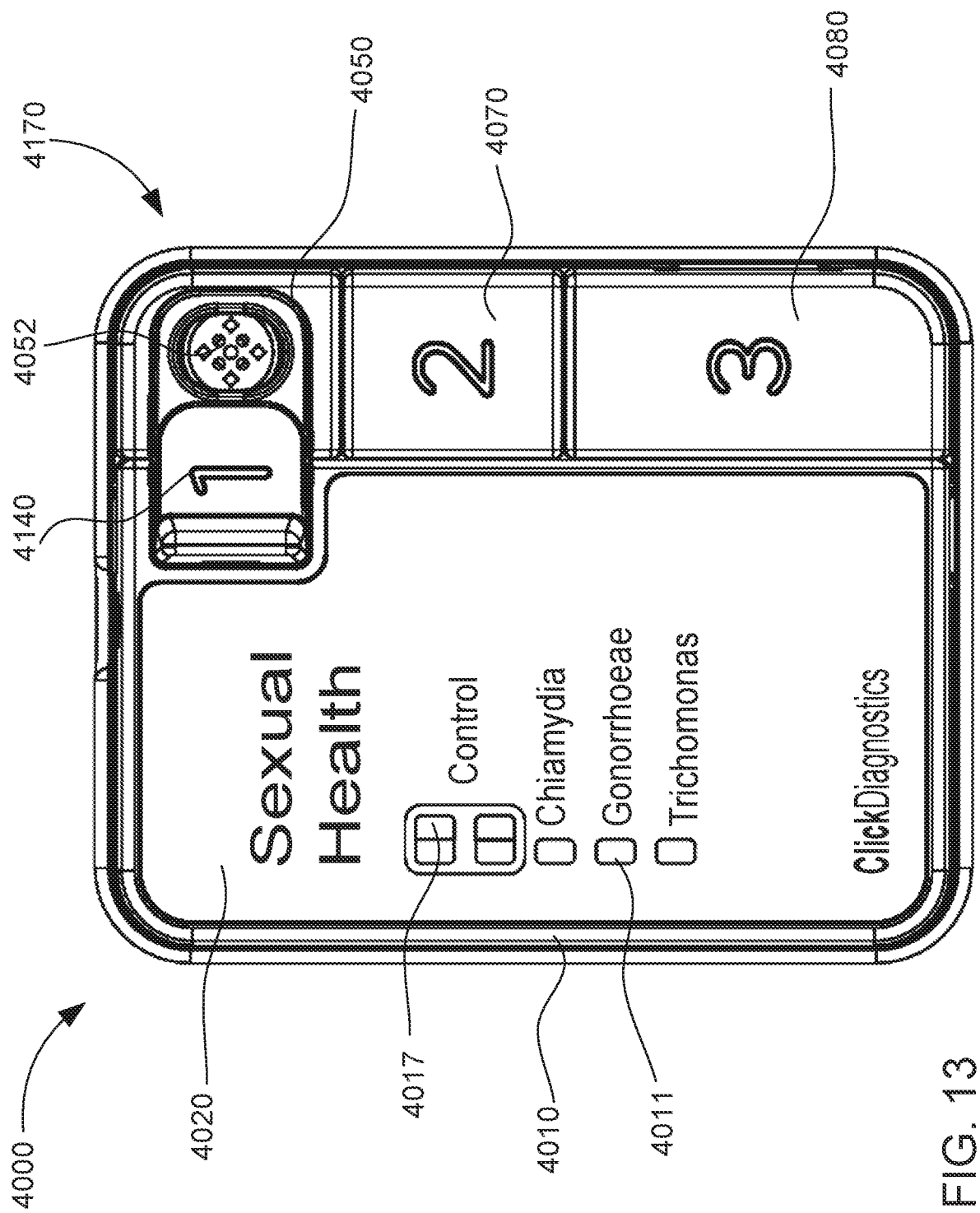

FIG. 13 is a schematic illustration of a molecular diagnostic test device 4000 (also referred to as a "test device" or "device"), according to an embodiment. The schematic illustration describes the primary components of the test device 4000 as shown in FIG. 12. The test device 4000 is an integrated device (i.e., the modules are contained within a single housing) that is suitable for use within a point-of-care setting (e.g., doctor's office, pharmacy or the like), decentralized test facility, or at the user's home. In some embodiments, the device 4000 can have a size, shape and/or weight such that the device 4000 can be carried, held, used and/or manipulated in a user's hands (i.e., it can be a "handheld" device). In other embodiments, the test device 4000 can be a self-contained, single-use device. In some embodiments, the test device 4000 can be configured with lock-outs or other mechanisms to prevent re-use or attempts to re-use the device.

Further, in some embodiments, the device 4000 can be a CLIA-waived device and/or can operate in accordance with methods that are CLIA waived. Similarly stated, in some embodiments, the device 4000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 4000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 4000 can be configured for long term storage in a manner that poses a limited likelihood of misuse (spoilage of the reagent(s), expiration of the reagents(s), leakage of the reagent(s), or the like). In some embodiments, the molecular diagnostic test device 4000 is configured to be stored for up to about 36 months, up to about 32 months, up to about 26 months, up to about 24 months, up to about 20 months, up to about 48 months, or any values there between.

The test device 4000 is configured to manipulate a biological sample S1 to produce one or more output signals associated with a target amplicon (e.g., a target SNP), and can be used to perform any of the molecular diagnostic methods described herein. Specifically, the device 4000 includes a sample preparation module 4200, an inactivation module 4300 (also referred to as a lysing module), a fluidic drive (or fluid transfer) module 4400, a mixing chamber (which functions as an amplification reagent module) 4500, an amplification module 4600, a detection module 4800 and a power and control module (not shown). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 4400) is not provided herein.

Figure 11:
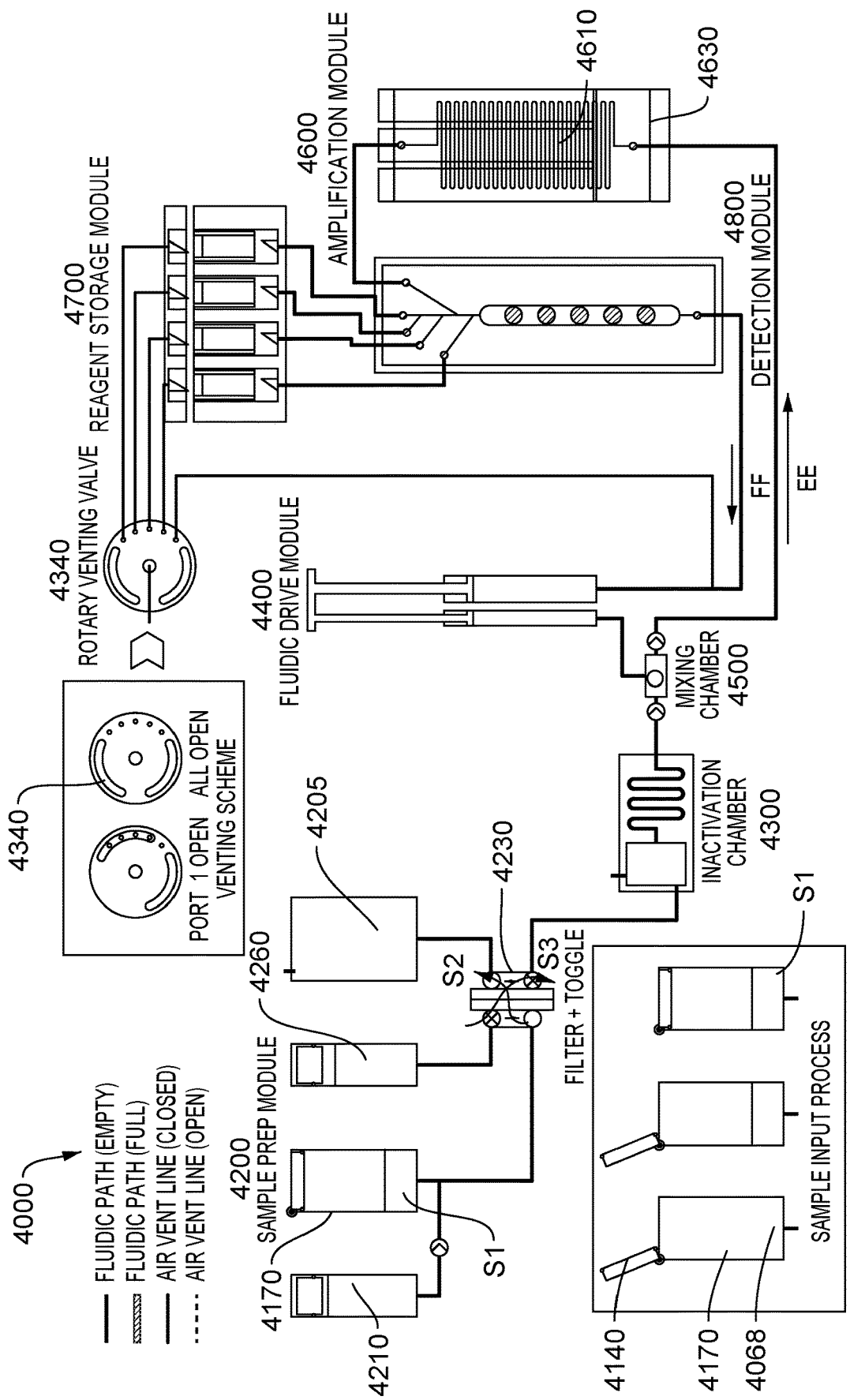
FIG. 11 is a schematic illustration of a molecular diagnostic test device, according to an embodiment.

The diagnostic test device 4000 includes a housing 4001 (including a top portion 4010 and a bottom portion 4030), within which the modules described herein are fully or partially contained. Similarly stated, the housing 4001 (including the top portion 4010 and/or the bottom portion 4030) at least partially surround and/or enclose the modules. As shown in FIGS. 11-12, the device 4000 includes a sample input module 4170, a sample preparation module 4200, an inactivation module 4300, a fluidic drive (or fluid transfer) module 4400, an amplification reagent module 4500 (see FIG. 11), an amplification module 4600, a detection module 4800, a reagent storage module 4700, a rotary venting valve 4340, and a power and control module 4950. In some embodiments, the sample preparation module 4200 can be considered as including the sample input module 4170 and/or the inactivation (also referred to as the lysing) module 4300, but in other embodiments, these modules can be considered as distinct from the sample preparation module 4200. In some embodiments, the sample preparation module 4200 can be considered as including the amplification reagent (or mixing) module 4500.

The housing assembly 4001 includes the top housing 4010, the bottom housing 4040, the vertical manifold 4035, and the sample transfer manifold 4100. As shown, the top housing 4010 includes a label 4020 that defines a series of detection openings 4011 that are aligned with the detection module 4800. In this manner, the signal produced by and/or on each detection surface of the detection module 4800 is visible through the appropriate detection opening 4011. In some embodiments, the top housing 4010 and/or the label 4020 is opaque (or semi-opaque), thereby "framing" or accentuating the detection openings. In some embodiments, for example, the top housing 4010 can include markings 4017 (e.g., thick lines, colors or the like) to highlight the detection opening 4011. For example, in some embodiments, the top housing 4010 can include indicia 4017 identifying the detection opening to a specific disease (e.g., *Chlamydia trachomatis* (CT), *Neisseria* gonorrheae (NG) and *Trichomonas vaginalis* (TV)) or control.

The top housing 4010 includes a lid portion to which the sample lid 4140 is movably coupled. The top housing 4010 includes a lock surface to which the lid 4140 engages to prevent downward motion of the lid 4140 and the sample input actuator 4050 when the lid 4140 is in the opened position.

Figure 16:
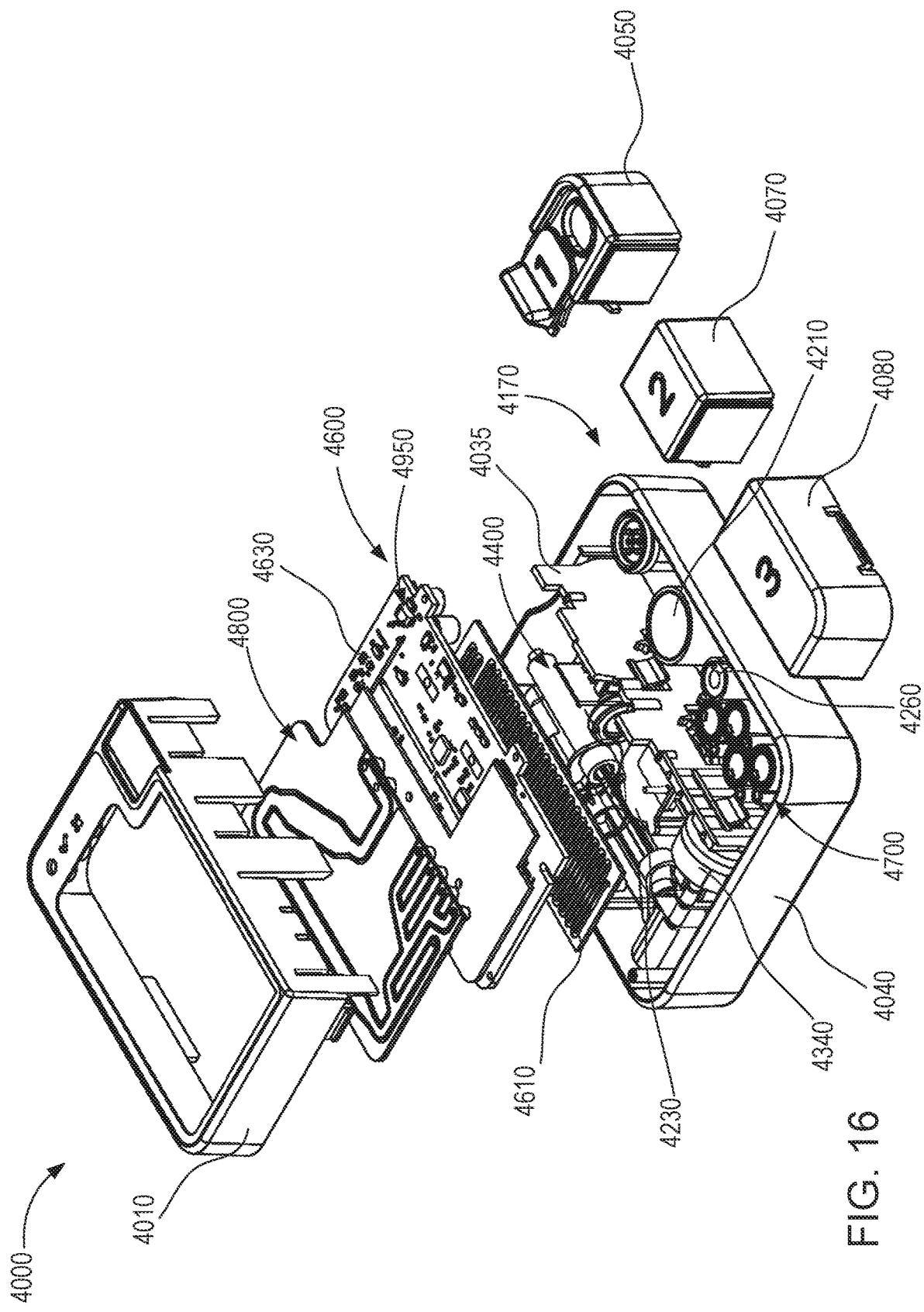
FIG. 16 is an exploded view of the molecular diagnostic test device shown in FIGS. 12 and 13.

Referring to FIG. 16, the housing assembly 4001 includes the vertical manifold 4035, which provides both structural support and defines flow paths for various fluids that are conveyed within the device 4000. In particular, the vertical manifold 4035 defines a series of reagent passages through which reagents are conveyed from the reagent module 4700 to the detection module 4800. Additionally, the vertical manifold 4035 defines on or more vent passages to allow venting to facilitate fluid movement throughout the device 4000.

The housing assembly 4001 includes the sample transfer manifold 4100, which provides both structural support and defines flow paths for various fluids that are conveyed within the device 4000. In particular, the sample transfer manifold 4100 includes a sample input portion 4102, a wash portion 4103, an elution portion 4104, and a reagent portion 4105.

The sample preparation module 4200 includes a sample input module 4170, a wash module 4210, an elution module 4260, a filter assembly 4230, and various fluidic conduits (e.g., tubes, lines, valves, etc.) connecting the various components. The device 4000 also includes the lysing module 4300 and the amplification reagent (or mixing) module 4500, which, together with the sample preparation module 4200, performs the nucleic acid extraction and preparation of an amplification solution according to any of the methods described herein. Thus, although the sample preparation module 4200, the sample input module 4170, the inactivation module 4300, and the amplification reagent module 4500 are described as separate modules, in other embodiments, the structure and function of the sample preparation module 4200 can be included within or performed by the inactivation module 4300, the amplification reagent module 4500, and/or the sample input module 4170, and vice-versa. Similarly stated, any of the sample input modules, sample preparation modules, inactivation modules and/or lysing modules described herein can include any of the structure and/or perform any of the functions of the other modules to perform any of the methods of sample preparation or nucleic acid extraction described herein. By eliminating the need for external sample preparation and a cumbersome instrument, the device 4000 is suitable for use within a point-of-care setting (e.g., doctor's office, pharmacy or the like) or at the user's home, and can receive any suitable biological sample S1. The biological sample S1 (and any of the input samples described herein) can be any of the types of samples described herein.

Figure 17:
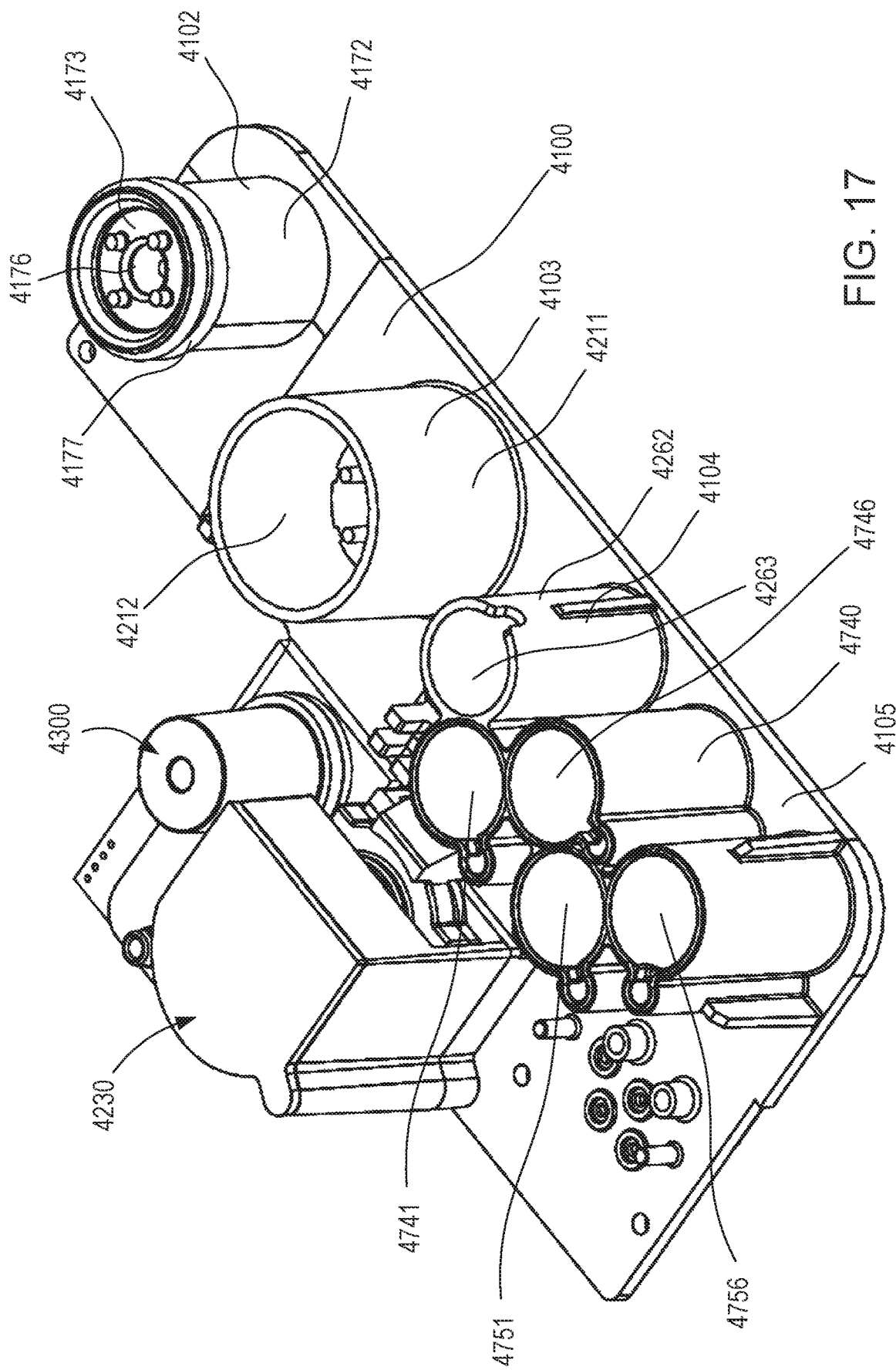
FIG. 17 is a perspective view of the molecular diagnostic test device shown in FIGS. 12 and 13, including a filter assembly and an inactivation assembly coupled thereto.
Figure 18:
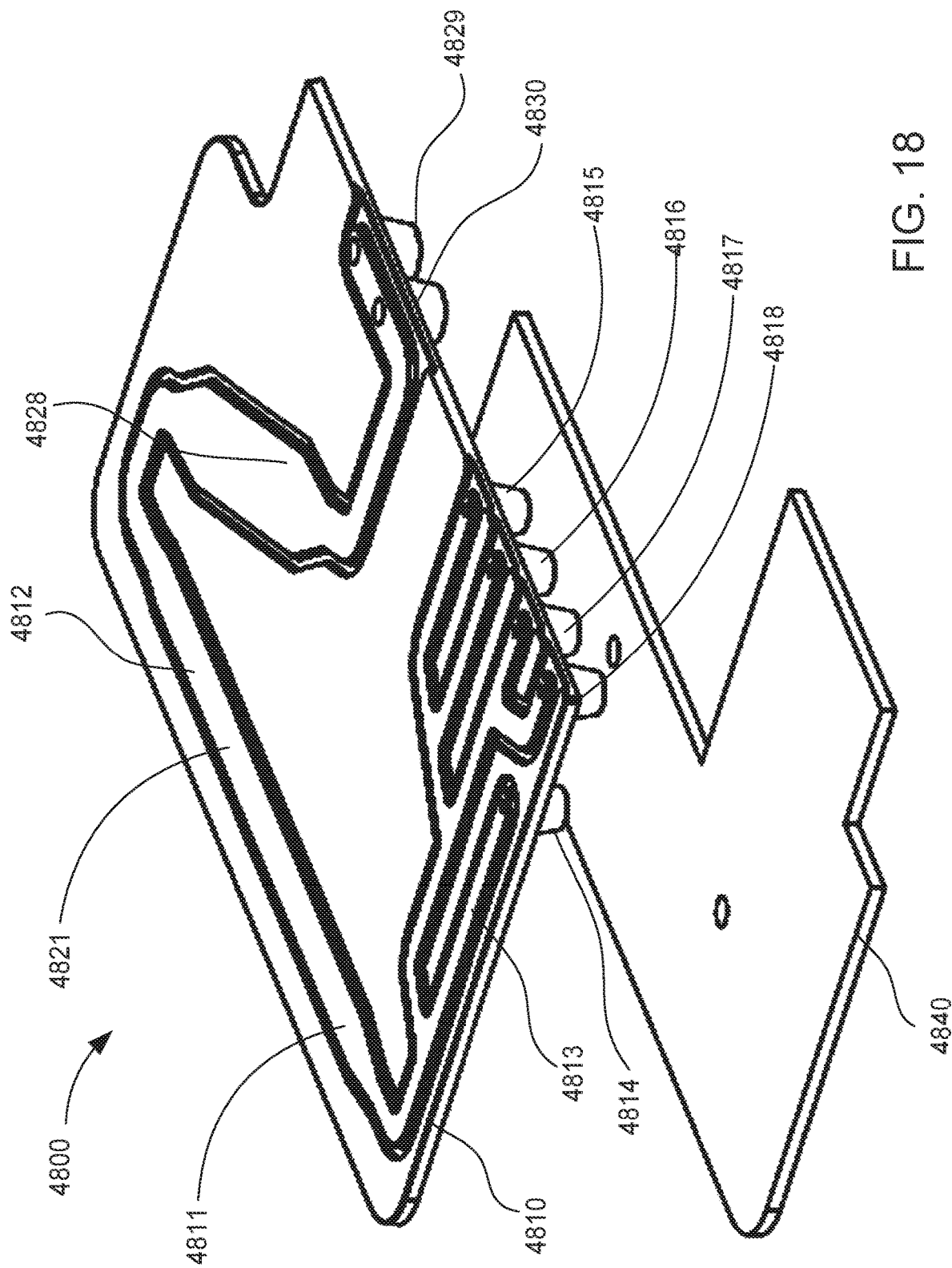
FIGS. 18 and 19 are a perspective exploded view and a front view, respectively, of a detection module of the molecular diagnostic test device shown in FIGS. 12 and 13.
Figure 19:
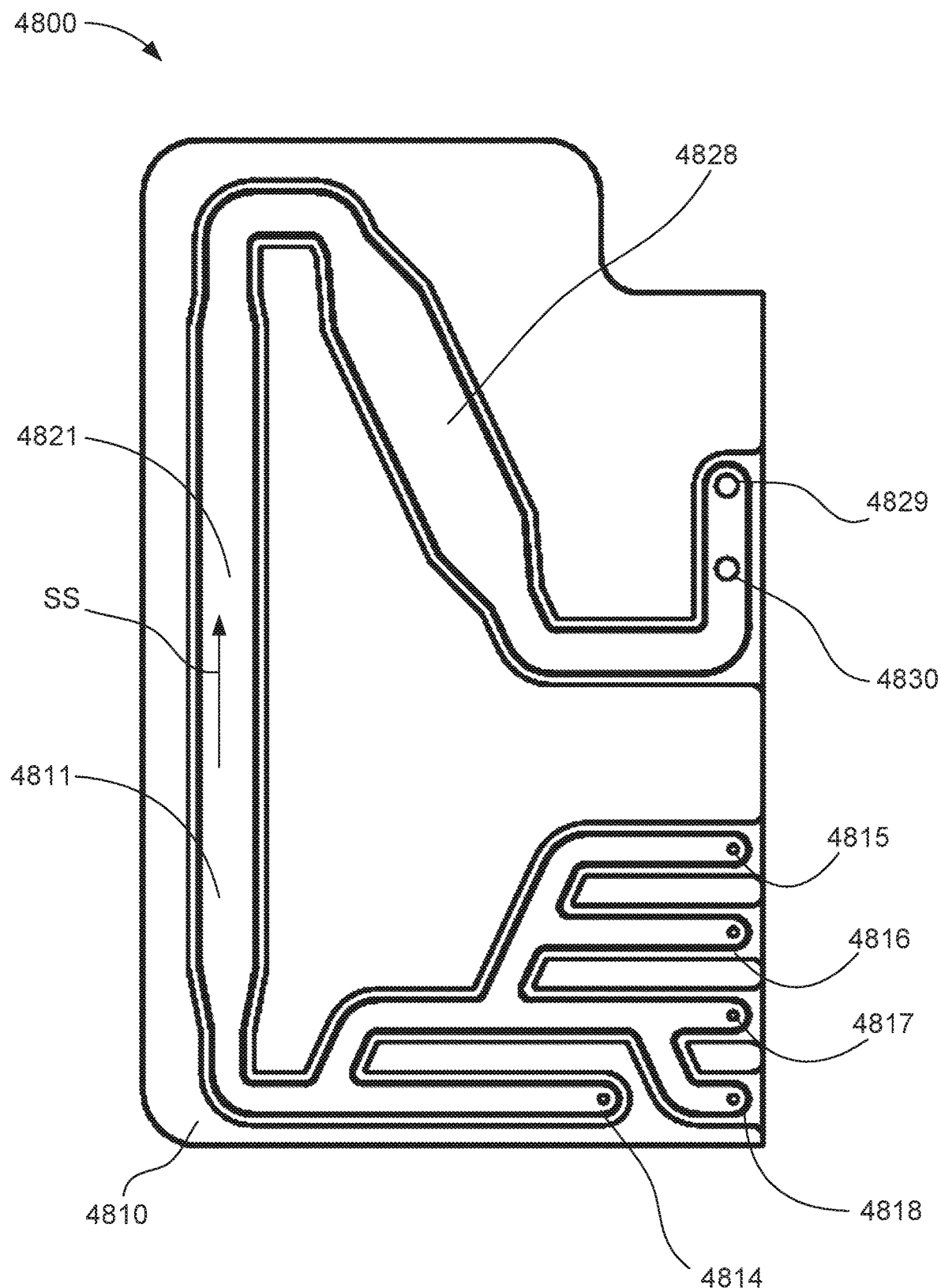

The sample input module 4170 is configured to receive a biological sample S1 containing a biological entity, and convey the biological sample toward the remaining elements of the sample preparation module 4200 (e.g., the filter assembly 4230). The sample input module 4170 includes the sample input portion 4102 of the sample transfer manifold 4100, the sample input (or first) actuator 4050, and the lid 4140. Referring to FIG. 17, the sample input portion 4102 of the sample transfer manifold 4100 includes a cylindrical housing 4172 and a cover. As shown, the top surface of the cylindrical housing 4172 (including the top surface 4173 and/or portions of the cover) and an inner surface of the first actuator 4050 define a sample input volume 4068, within which the biological sample is conveyed at the start of a test. The outer portion of the cylindrical housing 4172 includes one or more seals 4177 that slidingly engage the inner surface of the first actuator 4050 to form a fluid-tight seal. In some embodiments, the sample input volume 4068 or other portions of the sample input module 4170 can include a reagent (e.g., a positive control or other reagent as described herein).

The cylindrical housing 4172 defines a first (or vertical) fluid passage 4176 that is between (and fluid communication with) a sample input passage defined by the sample transfer manifold 4100 and that is in fluid communication with the wash module 4210 and the filter assembly 4230. In this manner, when the biological sample is compressed by the first actuator 4050 it is conveyed from the sample input volume 4068, through the first fluid passage and towards the filter assembly 4230.

The wash module 4210 is configured to convey a wash solution toward the remaining elements of the sample preparation module 4200 (e.g., the filter assembly 4230). In some embodiments, the wash module 4210 is configured such that it cannot be actuated out of the desired sequence of operations. Specifically, in some embodiments, the wash module 4210 is configured to be locked until after the biological sample has been conveyed to the sample preparation module 4200. The wash module 4210 includes the wash portion 4103 of the sample transfer manifold 4100, the wash (or second) actuator 4070, and a wash container. Referring to FIG. 17, the wash portion 4103 of the sample transfer manifold 4100 includes a cylindrical housing 4211 and a top surface (or cover) (not shown). The upper portion of the cylindrical housing 4211 defines a volume 4212 within which a wash container (not shown) is disposed. The wash container can be a sealed wash container that allows the sample wash solution to be stored for long periods of time (e.g., 6 months or longer). The wash solution within the wash container can be any suitable solution. The wash module 4210 is actuated by the wash (or second) actuator 4070

As described herein, the biological sample and the wash solution are conveyed through the filter assembly 4230. The filter assembly is configured to receive an elution buffer (via a backflush operation) to convey the desired particles (and the elution buffer) to the lysing module 4300. After the filtering operation, the elution buffer and the captured particles flow out of the filter assembly 4230 and toward the lysing module 4300 via a sample outlet port.

The elution module (or assembly) 4260 of the sample preparation module 4200 is contained within the housing, and defines an elution volume within which an elution composition is stored. The elution composition can be any of the elution compositions described herein. In some embodiments, the elution composition can include proteinase K, which allows for the release of any bound cells and/or nucleic acid molecules (e.g., DNA) from the filter membrane. The output from the elution module 4260 can be selectively placed in fluid communication with the filter assembly 4230, when the filter assembly is toggled into a backflow configuration, as described above. Thus, the elution module 4260 can include any suitable flow control devices, such as check valves, duck-bill valves, or the like to prevent flow back towards and/or into the elution volume.

In some embodiments, the elution module 4260 is configured such that it cannot be actuated out of the desired sequence of operations. Specifically, in some embodiments, the elution module 4260 is configured to be locked until after the biological sample has been conveyed to the sample preparation module 4200 and the wash operation (described above) has occurred. The elution module 4260 includes the elution portion 4104 of the sample transfer manifold 4100, the reagent (or third) actuator 4080, and an elution plunger (not shown). Referring to FIG. 17, the elution portion 4104 of the sample transfer manifold 4100 includes a cylindrical housing 4262 that defines an elution volume 4263 within which the elution buffer (or composition) is contained. The elution module 4260 is actuated by the reagent (or third) actuator 4080.

The lysing module 4300 includes a chamber body and a heater. In use, the sample (e.g., the filtered sample) is conveyed into the chamber body and heated to a first temperature within a lysing temperature range to lyse certain constituents in the solution or de-activate the enzymes present in input fluid after lysis occurs. In some embodiments, the lysing module 4300 can be used in conjunction with RT-PCR and can heat or maintain the solution at a temperature to release a ribonucleic acid (RNA) molecule within the solution.

After the lysing and/or inactivation operations, the output from the lysing module 4300 can be conveyed into the mixing module (also referred to as the amplification reagent module) 4500, which mixes the output of inactivation module 4300 with the reagents to produce an amplification solution. In some embodiments, the amplification reagent module 4500 contains a primer set targeting a single nucleotide polymorphism (SNP) locus in a polynucleotide of the biological sample S1. The SNP primer set P can include any of the SNP primer sets shown and described herein. In some embodiments, the amplification reagent module 4500 is configured to reconstitute the reagent in a predetermined input volume, while ensuring even local concentrations of reagents in the entirety of the volume. In some embodiments, the mixing chamber module 4500 is configured to produce and/or convey a sufficient volume of liquid for the amplification module 4600 to provide sufficient volume output to the detection module 4800. The mixing module 4500 can be any suitable mixing module, such as those shown and described in International Patent Publication No. WO2016/109691, entitled "Devices and Methods for Molecular Diagnostic Testing," which is incorporated herein by reference in its entirety The fluidic drive (or transfer) module 4400 can be a pump or series of pumps configured to produce a pressure differential and/or flow of the solutions within the diagnostic test device 4000. Similarly stated, the fluid transfer module 4400 is configured to generate fluid pressure, fluid flow and/or otherwise convey the biological sample and the reagents through the various modules of the device 4000. The fluid transfer module 4400 is configured to contact and/or receive the sample flow therein. Thus, in some embodiments, the device 4000 is specifically configured for a single-use to eliminate the likelihood that contamination of the fluid transfer module 4400 and/or the sample preparation module 4200 will become contaminated from previous runs, thereby negatively impacting the accuracy of the results. The fluid transfer module 4500 can be any suitable fluid transfer module, such as those shown and described in International Patent Publication No. WO2016/109691, entitled "Devices and Methods for Molecular Diagnostic Testing," which is incorporated herein by reference in its entirety.

Figure 14:
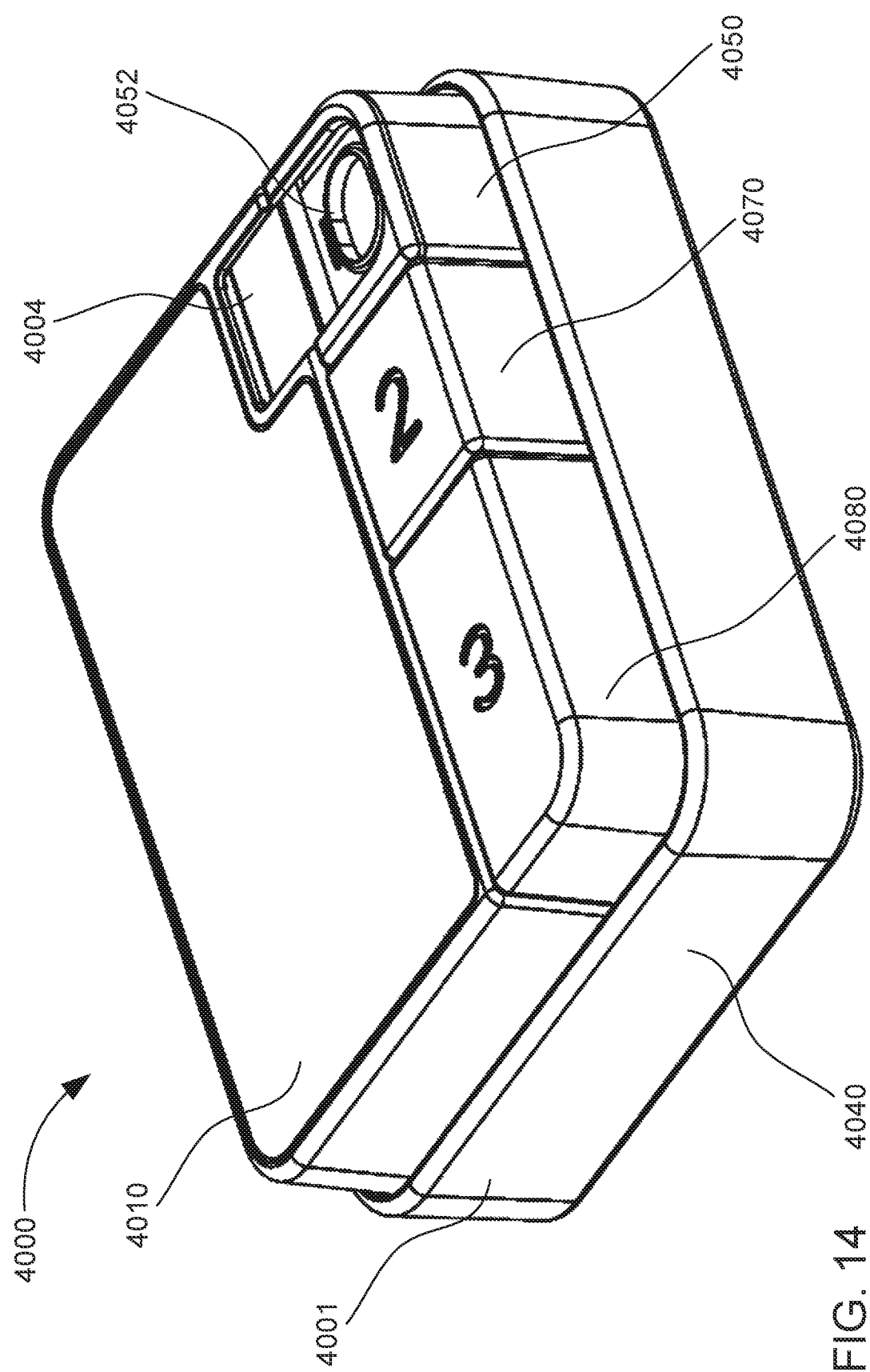
FIG. 14 is a perspective view of the molecular diagnostic test device shown in FIGS. 12 and 13, with the lid removed to show the sample input opening.
Figure 15:
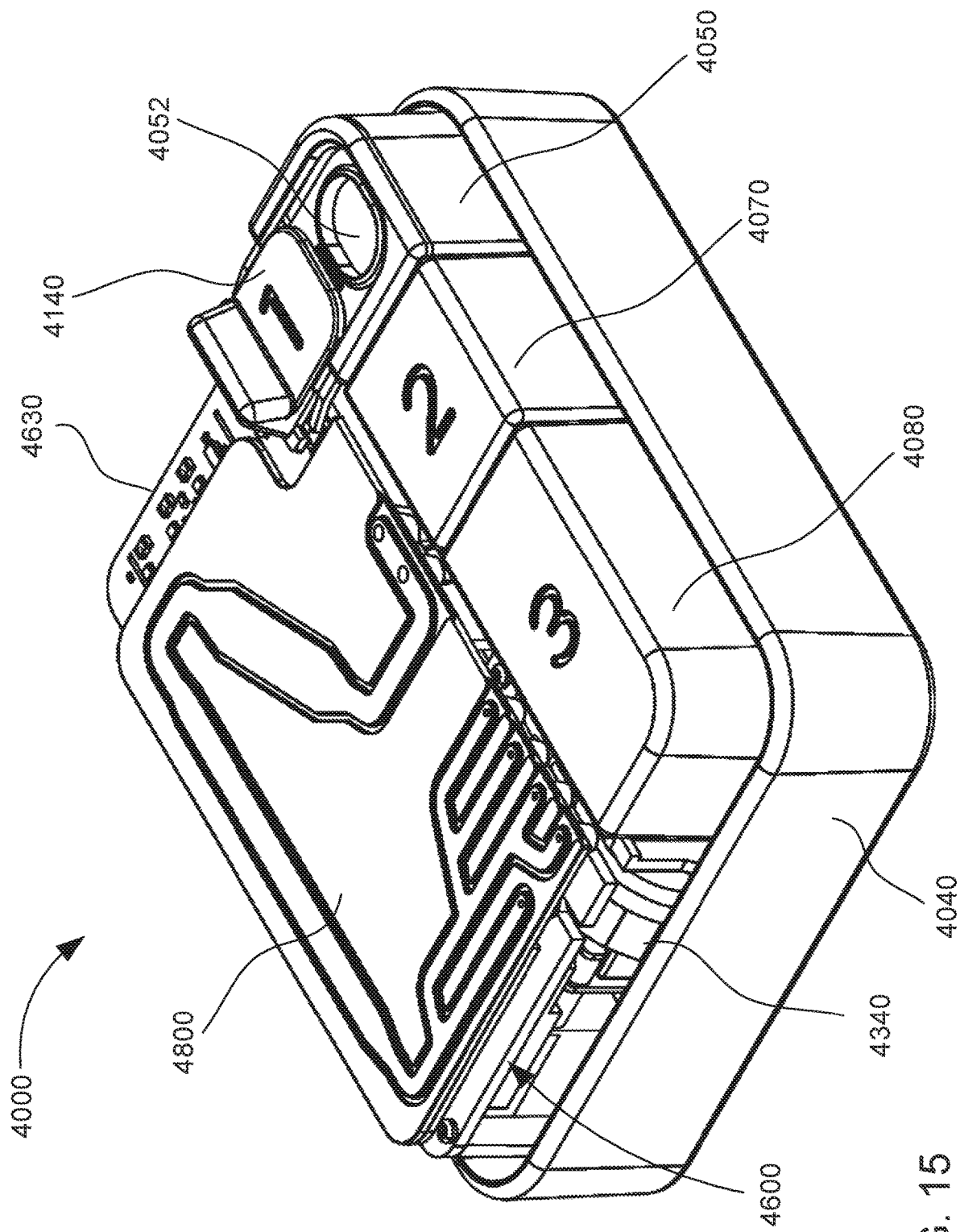
FIG. 15 is a perspective view of the molecular diagnostic test device shown in FIGS. 12 and 13, with the top portion of the housing removed to show the internal components.

After being mixed within the amplification reagent module 4500, the prepared sample is then conveyed to the amplification module 4600 (as shown by the arrow EE in FIG. 14). The amplification module 4600 includes a flow member 4610 and a heater 4630. The flow member 4610 can be any suitable flow member that defines a volume or a series of volumes within which the that prepared solution can flow and/or be maintained to amplify the target nucleic acid molecules within the solution. The heater 4630 can be any suitable heater or group of heaters coupled to the flow member 4610 that can heat the prepared solution within the flow member 4610 to perform any of the amplification operations as described herein.

In some embodiments, the flow member 4610 defines a single volume within which the prepared solution is maintained and heated to amplify the nucleic acid molecules within the prepared solution. In other embodiments, the flow member 4610 can define a "switchback" or serpentine flow path through which the prepared solution flows. Similarly stated, the flow member 4610 defines a flow path that is curved such that the flow path intersects the heater 4630 at multiple locations. In this manner, the amplification module 4600 can perform a "flow through" amplification reaction where the prepared solution flows through multiple different temperature regions.

Although the amplification module 4600 is generally described as performing a thermal cycling operation on the prepared solution, in other embodiment, the amplification module 4600 can perform any suitable thermal reaction to amplify nucleic acids within the solution. In some embodiments, the amplification module 4600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process The detection methods enabled by the device 4000 include sequential delivery of the detection reagents and other substances within the device 4000. Further, the device 4000 is configured to be an "off-the-shelf" product for use in a point-of-care location (or other decentralized location), and is thus configured for long-term storage. Accordingly, the reagent storage module 4700 is configured for simple, non-empirical steps for the user to remove the reagents from their long-term storage containers, and for removing all the reagents from their storage containers using a single user action. In some embodiments, the reagent storage module 4700 and the rotary selection valve 4340 are configured for allowing the reagents to be used in the detection module 4800, one at a time, without user intervention.

Specifically, the device 4000 is configured such that the last step of the initial user operation (i.e., the depressing of the reagent actuator 4080) results in dispensing the stored reagents. This action crushes and/or opens the sealed reagent containers present in the assembly and relocates the liquid for delivery. The rotary venting selector valve 4340 allows the reagent module 4700 to be vented for this step, and thus allows for opening of the reagent containers, but closes the vents to the tanks once this process is concluded. Thus, the reagents remain in the reagent module 4700 until needed in the detection module 4800. When a desired reagent is needed, the rotary valve 4340 opens the appropriate vent path to the reagent module 4700, and the fluidic drive module 4400 applies vacuum to the output port of the reagent module 4700 (via the detection module 4800), thus conveying the reagents from the reagent module 4700. The reagent module 4700 and the valve 4340 can be similar to the reagent modules and valves shown and described in International Patent Publication No. WO2016/109691, entitled "Devices and Methods for Molecular Diagnostic Testing," which is incorporated herein by reference in its entirety.

The detection module 4800 is configured to receive output from the amplification module 4600 and reagents from the reagent module 4700 to produce a colorimetric change to indicate presence or absence of target organism in the initial input sample. The detection module 4800 also produces a colorimetric signal to indicate the general correct operation of the test (positive control and negative control). In some embodiments, color change induced by the reaction is easy to read and binary, with no requirement to interpret shade or hue. Referring to FIGS. 13 and 14, the detection module includes a lid (not shown), a detection housing 4810 and a heater 4840. The heater 4840 can be similar to any of the circuit board heaters described herein and also shown and described in International Patent Publication No. WO2016/109691, entitled "Devices and Methods for Molecular Diagnostic Testing," which is incorporated herein by reference in its entirety.

The lid and the detection housing 4810 form a flow cell for detection. The housing 4810 defines a detection chamber/channel 4812 having a sample inlet portion 4813, a reagent inlet portion, a detection portion 4821, and an outlet portion 4828. The sample inlet portion 4813 includes the sample inlet port 4814, which is fluidically coupled to the outlet of the amplification module 4600 and receives the amplified sample. The reagent inlet portion includes a first reagent inlet port 4815, a second reagent inlet port 4816, a third reagent inlet port 4817, and a fourth reagent inlet port 4818. The first reagent inlet port 4815 is coupled to the reagent module 4700 via the vertical manifold 4035. Thus, in use a first reagent (e.g., a detection reagent, such as the first reagent R1 described above with reference to the reagent module 1700) can be conveyed into the detection channel 4812 via the first reagent inlet port 4815. The second reagent inlet port 4816 is coupled to the reagent module 4700 via the vertical manifold 4035. Thus, in use a second reagent (e.g., a wash solution) can be conveyed into the detection channel 4812 via the second reagent inlet port 4816. The third reagent inlet port 4817 is coupled to the reagent module 4700 via the vertical manifold 4035. Thus, in use a third reagent (e.g., a detection reagent, such as the second reagent R2 described above with reference to the reagent module 1700) can be conveyed into the detection channel 4812 via the third reagent inlet port 4817. The fourth reagent inlet port 4818 is coupled to the reagent module 4700 via the vertical manifold 4035. Thus, in use a fourth reagent (e.g., a second flow of a detection reagent, such as the second reagent R2 described above with reference to the reagent module 1700) can be conveyed into the detection channel 4812 via the first reagent inlet port 4818.

The detection channel 4812 includes an entrance portion 4811, a detection portion 4821, and outlet portion 4828. The detection portion (or "read lane") 4821 is defined, at least in part by, and/or includes a series of detection surfaces. The detection surfaces 4821 include a series of capture probes to which the target amplicon can be bound when the detection solution flows across the detection surface 4821. For example, the capture probes may include one or more allele-specific probes, one or more capture probe that bind the target amplicon outside the SNP locus, and/or one or more capture probes that bind an second target amplicon for the same organism. In some embodiments, the detection surfaces 4821 are configured for multiplex detection and/or drug-sensitivity determination using multiple SNP loci and/or multiple target organisms. The capture probes can be any suitable probes formulated to capture or bind to the target amplicon, such as those described above with respect to the detection module 1800.

The device 4000 can be used to perform any of the methods described herein. To use the device, a biological sample is first placed into the sample input volume 4068, as described above. The lid 4140 is then moved to it closed position, thereby sealing the sample input volume 4068. After the lid 4140 is closed, the first actuator 4050 can be manipulated to actuate the sample input module 4170. Movement of the first actuator 4050 compresses the sample input volume 4068 and pushes the sample to the filter assembly 4230. The second actuator 4070 can then be depressed. This causes the wash solution to be conveyed into the filter assembly 4230, as described above. The third actuator 4080 can then be depressed to actuate the filter assembly 4230 and also causes the elution solution to be conveyed into the filter assembly 4230, as described above. The movement of the third actuator 4080 also releases the reagents from the reagent canisters.

Although the device 4000 is described as including a filter assembly 4230, in some embodiments, a sample preparation device need not include a filter or filter assembly. For example, in some embodiments, the sample input may be directly linked to a lysing/inactivation chamber, similar to the lysing chamber 4300 as shown above. Advantages of a device without a filter assembly include lower pressures in the device, no risk of breaking a filter, fewer parts, fewer reagents required, higher recovery of target organisms from the clinical sample matrix and higher recovery of DNA from target organisms. In such embodiments, a device differs from the device 4000 in that the sample is flowed from the input module 4170 directly to the lysing module 4300. In some embodiments, the sample may be lysed by heating without need for a specialized lysis buffer or lysis enzymes. Any proteases or nucleases released from the cells of the sample will be inactivated by heating. For example, a sample may be flowed into the lysing module and held until the module reaches a set temperature (for example greater than 90 C) and then flowed through an inactivation segment. In the inactivation segment, the sample is rapidly heated to 95 C causing the cells in the sample to lyse and proteins from within the cells to be inactivated.

In an aspect, the disclosure provides, a molecular diagnostic device, comprising a sample preparation module configured to receive a biological sample, wherein the biological sample comprises a polynucleotide; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele.

In some embodiments, the primer set is designed to flank the SNP locus.

In some embodiments, a length of a target region flanked by the primer set is between about 60 and about 140 base pairs.

In some embodiments, a length of a target region flanked by the primer set is between about 80 and about 120 base pairs.

In some embodiments, the target amplicon comprises minimal secondary structure.

In some embodiments, wherein the primer set designed to target a SNP locus comprises: i) an upstream oligonucleotide primer substantially complementary to an upstream primer binding site at the 5' terminus of the target region on the antisense strand; and ii) a downstream oligonucleotide primer substantially complementary to a downstream primer binding site at the 3' terminus of the target region on the sense strand.

In some embodiments, the molecular diagnostic device comprises a temperature controller configured to maintain the temperature of the detection module at about 5° C., about 10° C., or about 15° C. less than the melting temperature of the first probe.

In some embodiments, the detection module comprises a temperature controller configured to maintain a predetermined temperature for the detection module, and wherein the first probe is designed to have a melting temperature at about 5° C., about 10° C., or about 15° C. less than the predetermined temperature.

In some embodiments, the probe is substantially complementary to a probe binding site comprising the SNP locus, and comprises a nucleotide matched the target allele.

In some embodiments, the probe comprises at most two nucleotide mismatches to the probe binding site.

In some embodiments, the probe is perfectly complementary to the probe binding site.

In some embodiments, the probe does not overlap the primer set design to target the SNP locus.

In some embodiments, the detection module comprises a second probe substantially complementary to a second probe binding site, wherein the second probe binding site does not comprise the SNP locus.

In some embodiments, the second probe binding site does not overlap the binding site of the first probe. In some embodiments, the binding site for the first probe and the binding site for the second probe have partial overlap (e.g., overlap of 1 nt, 2 nt, 3 nt, or more). In some embodiments, the binding site for the second probe does not comprise the SNP locus, as the second probe is designed not to discriminate between alleles at the SNP locus.

In some embodiments, the detection module comprises a second probe substantially complementary to a second probe binding site within the target amplicon, wherein the second probe binding site does not overlap the binding site of the first probe.

In some embodiments, the target allele is a drug-resistance allele.

In some embodiments, the molecular diagnostic device specifically detects the drug-resistance allele in the biological sample.

In some embodiments, the allele is a drug-sensitivity allele.

In some embodiments, the molecular diagnostic device specifically detects the drug-resistance allele in the biological sample.

In some embodiments, the SNP locus is within a gyrA region.

In some embodiments, the primer set is designed to flank the gyrA 91 locus.

In some embodiments, a length of the gyrA region flanked by the primer set is between about 60 and about 140 base pairs.

In some embodiments, a length of the gyrA region flanked by the primer set is between about 80 and about 120 base pairs.

In some embodiments, a length of the gyrA region flanked by the primer set includes a secondary structure.

In some embodiments, the first probe is designed to maximize binding to the wild type, ciprofloxacin-sensitive gyrA Ser-91 genotype while minimizing binding to other SNPs at a gyrA Ser-91 site that confers a drug resistance.

In some embodiments, the first probe is substantially complementary to a first probe binding site comprising the codon encoding gyrA Ser-91, and wherein the first probe comprises a nucleotide that matches an allele encoding ciprofloxacin-sensitive gyrA Ser-91 genotype.

In some embodiments, the first probe discriminates between an allele encoding the ciprofloxacin-sensitive gyrA Ser-91 genotype and the antiallele encoding the gyrA Ser-91 site that confers resistance to ciprofloxacin.

As used here, the term "discriminates" refers to the ability or capacity of a device to determine the presence of a particular SNP of interest within an amplified region of sequence. For example, the device may produce an intensity of signal from the SNP-specific capture probe that indicates the presence of the target allele at the SNP locus in the target amplicon (or other polynucleotide) introduced into the detection module (whether the target amplicon is produced on a device having both amplification and detection module; supplied to a device having a detection module but no amplification module; or transferred from a device having an amplification module to a device having a detection module). In some embodiments, the signal (e.g., a colorimetric change) produced by the device at test spot (e.g., detection surface detection surface 4821) having the capture probe is compared to the signal produced by the same or equivalent device when the target amplicon (or other polynucleotide) lacking the target allele at the SNP locus is provided to the detection module. Stated differently, response criteria can be set by standardization of signal intensity from similarly manufactured devices. The control probe is an optimal feature of the device. In some embodiments, the signal produced by the device from the test spot is compared to the signal produced by the device at a control spot (e.g., a detection surface 4821) having a control capture probe. For example, the device may be engineered or calibrated to produce a similar or substantially equal signal at the two detection surfaces (capture probe and control capture probe) as an indicator for presence of the target allele; and to produce a reduced signal from the capture probe, compared to the control capture probe, where the target amplicon (or other polynucleotide) lacks the target allele at the SNP locus.

Stated different, the signal from the two detection surfaces may be similar or substantially equal when the biological sample comprising a polynucleotide from a drug-sensitive (or drug-resistant) pathogen (e.g. an antibiotic-sensitive bacteria); and different when the biological sample comprising a polynucleotide from a drug-resistant (or drug-sensitive) pathogen (e.g. an antibiotic-resistant bacteria). Thus, in some embodiments of the devices and methods of the disclosure, the device produces a test signal in response to a test polynucleotide that differs sufficiently in comparison from the reference signal produced in response to a reference polynucleotide so that the test signal and be distinguished from the reference signal, permitting an instrument or user to distinguish between a test polynucleotide have a characteristic (e.g., presence of an allele) and a test polynucleotide not having that characteristic (e.g., absence of an allele). Without being bound by theory, the control probe may serve, in some embodiments, one or more of at least three roles: 1) to assure that the target (e.g., gyrA) amplicon was in fact generated by the device; 2) to permit a user (or the device itself) to compare signal intensity between the SNP-specific capture probe and the control capture probe in order to make a call: of "SNP present" or "SNP absent"; and 3) to serve to detection the presence of an organism (regardless of presence of absence of the SNP) (e.g., when the user does not intend to determine drug resistance but merely wishes to employ the device for detection of the pathogen).

In some embodiments, the first probe is characterized by a thermodynamic fulcrum and/or melting temperature of about 52° C.

In some embodiments, the first probe comprises between 12 and 25 nucleotides.

In some embodiments, the first probe comprises between 18 and 22 nucleotides.

In some embodiments, the first probe has a melting temperature of between 50° C. and 60° C.

In some embodiments, the first probe comprises, consists essentially of, or consists of a sequence selected from any one of SEQ ID NO: 14-20.

In some embodiments, the second probe comprises between 12 and 25 nucleotides.

In some embodiments, the second probe comprises between 18 and 22 nucleotides.

In some embodiments, the second probe has a melting temperature of between 50° C. and 60° C.

In some embodiments, the second probe comprises, consists essentially of, or consist of a sequence selected from any one of SEQ ID NO: 6 or 22.

In some embodiments, the molecular diagnostic device detects the allele in a biological sample comprising at least about 0.5 nM, at least about 1 nM, at least about 1.5 nM, at least about 2 nM, at least about 6 nM, at least about 8 nM, at least about 10 nM, or at least about 15 nM of the polynucleotide comprising the SNP locus if the SNP locus comprises the allele.

In some embodiments, the molecular diagnostic device determines whether a subject suspected of having a drug-sensitive bacterial infection has a drug-sensitive bacterial infection.

In some embodiments, the molecular diagnostic device determines whether a subject suspected of having a drug-resistant bacterial infection has a drug-resistant bacterial infection.

In another aspect, the disclosure a provides method, comprising a) introducing into any of the molecular diagnostic devices of the disclosure a biological sample from a subject having or suspected of having a disease or disorder characterized by one or more SNPs associated with susceptibility to a treatment, wherein the biological sample comprising a polynucleotide from the subject, b) administering the treatment if the molecular diagnostic device indicates the polynucleotide comprises a SNP locus comprising an allele associated with susceptibility to the treatment.

In some embodiments, the disease or disorder is a bacterial infection.

In another aspect, the disclosure a method, performed in a molecular diagnostic device comprising a sample preparation module configured to receive a biological sample, wherein the biological sample comprises a polynucleotide from a target bacteria; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising amplifying a target amplicon from the polynucleotide from the target bacteria; optionally, amplifying a second target amplicon from the polynucleotide from the target bacteria; reacting the first target amplicon with a first probe to produce a first signal indicating susceptibility of the target bacteria to drug; optionally, reacting the first target amplicon with a second probe to produce a second signal indicating presence of the target bacteria in the biological sample and/or amplification of the target amplicon; and optionally, reacting the second target amplicon with a third probe to produce a third signal indicating presence of the target bacteria in the biological sample and/or amplification of either or both of the first target amplicon and the second target amplicon.

In some embodiments, the amplifying the first gene and the amplifying the second gene are performed simultaneously within a stand-alone device.

In some embodiments, the first signal, second signal, and/or third signal are produced without performing any melting curve analysis.

In some embodiments, the target bacteria is *Neisseria gonorrheae* (NG); the SNP locus is within the gyrA gene of NG; the amplifying the target amplicon comprises mixing a biological sample with a primer set designed to target a gyrA region; and thermal cycling the mixture of the biological sample and the primer set between a first temperature and a second temperature at a rate sufficient to produce the first target amplicon and optionally the second target amplicon.

In another aspect, the disclosure provides a method, performed in a molecular diagnostic device comprising a sample preparation module configured to receive a biological sample, wherein the biological sample comprises a polynucleotide from a target bacteria; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising: performing a molecular diagnostic test on the biological sample to determine A) the presence of a target bacteria and B) the presence of the target allele within the target bacteria that confers resistance to a first antibiotic; and administering, based on a result of the molecular diagnostic test, a second antibiotic.

Methods and Devices for an NG Ciprofloxacin-Susceptible PCR Assay

Figure 3:
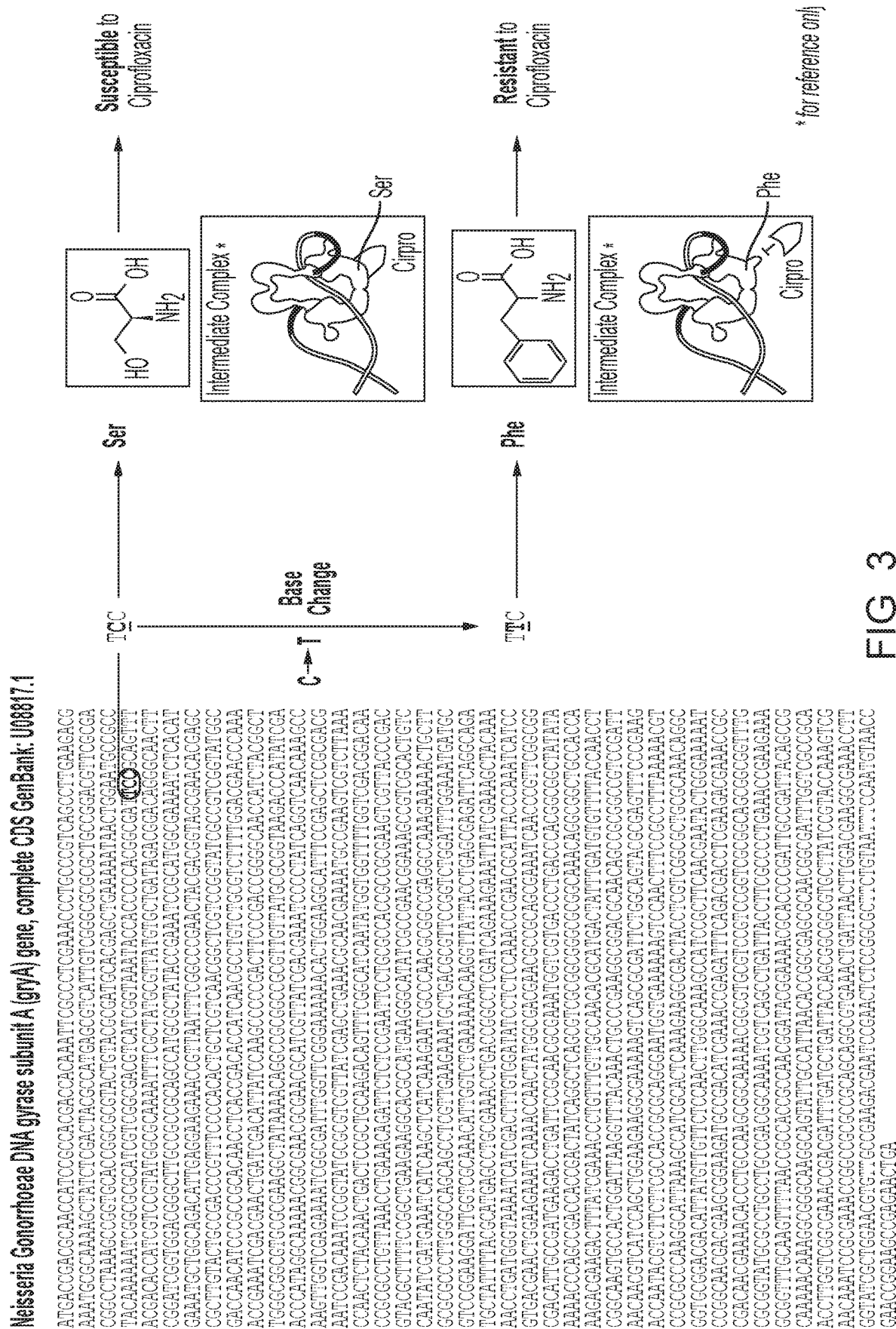
FIG. 3 illustrates a single nucleotide polymorphism (SNP) at codon 91 of the gyrA gene (gyrA Ser91) (Genbank U08817.1) (SEQ ID NO: 1).

Ciprofloxacin-susceptible isolates of NG harbor a single nucleotide polymorphism (SNP) at codon 91 of the gyrA gene (gyrA Ser91) (SEQ ID NO: 1) (FIG. 3). Although mutations in other codons (gyrA Asp95) and genes (parC) have been detected, mutations in the gyrA Ser91 codon are necessary and sufficient to confer ciprofloxacin resistance.

The device performs PCR amplification of target amplicons through targeted primers followed by end point detection using capture probes and enzyme-based signal amplification. Based on this product design, it is possible to discriminate SNP's either at the PCR stage, the capture stage, or both. We have empirically determined that discriminating the SNP using capture probes is the most feasible approach. Thus, the primer set was designed to amplify the gyrA region in which subsequent probes would discriminate the Ciprofloxacin-susceptible SNP.

Figure 4:
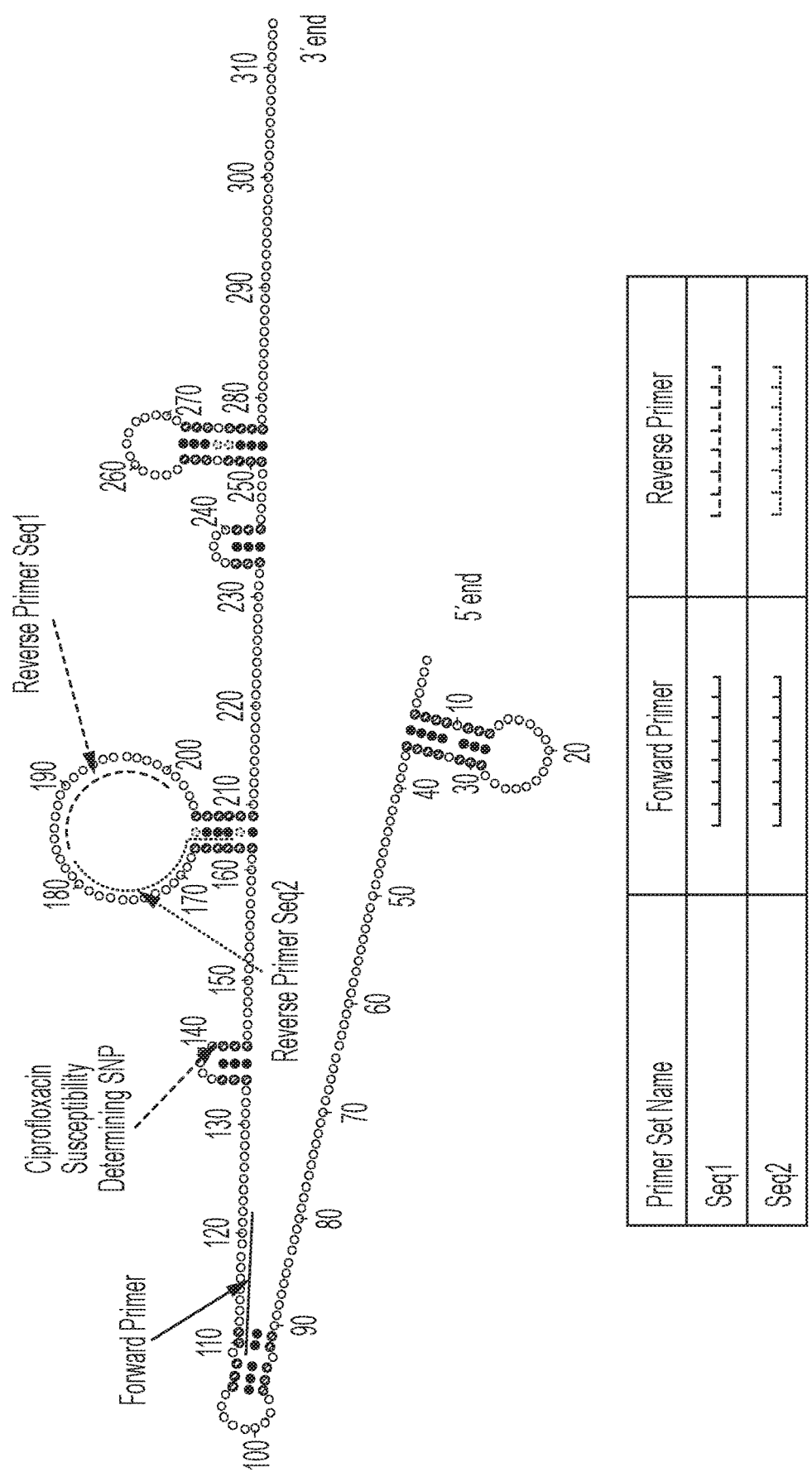
FIG. 4 illustrates forward and reverse PCR primers, according to an embodiment.

The forward and reverse PCR primers were designed to flank the gyrA 91 locus so they will amplify all NG gyrA genotype variants (including those containing the ciprofloxacin-susceptible gyrA Ser-91 wild type SNP and those containing the ciprofloxacin-resistant gyrA Phe-91, gyrA Tyr-91, gyrA Asn-95 and gyrA Gly-95 SNPs (FIG. 4). Since the ciprofloxacin-susceptibility test is intended to integrate with the current NT/TV product, design parameters focused on primer candidates with a Tm of 60 degrees to match current STI assay (see International Patent Publication No. WO2016/109691, entitled "Devices and Methods for Molecular Diagnostic Testing," which is incorporated herein by reference in its entirety), and targeting regions with minimal secondary structure and avoiding regions of high G+C (guanine and cytosine) content. Alignment with other related *Neisseria* species, such as *Neisseria meningitidis*, were assessed to ensure primers only amplify NG.

The PCR performance of these primers was studied using ciprofloxacin-susceptible and ciprofloxacin-resistant NG strains obtained from the CDC antibiotic resistant NG strain isolate bank. We performed real-time PCR experiments in TE buffer using the master mix composition optimized for the single-plex and existing 4-plex STI assay and employed a laboratory thermocycler programmed to cycling conditions of time and temperature that simulate the fast cycling performance of the Click serpentine PCR module. The best performing primer sets were then further assessed and optimized in subsequent experiments with allele-specific probes as described in the following section.

In some embodiments, the devices and method of the disclosure have the ability to detect SNPs without the use of melt curves, which are difficult to read even by trained laboratorians. A challenge to be overcome was designing an efficient primer set around a SNP. This can be problematic because the target region could contain sequences that result in secondary structures in the amplicon. Without being bound by theory, it is believed that in some cases, the devices described herein are able to solve this problem because the temperature ramp rates are extremely fast. Without being bound by theory, it is believed that in some cases, as the amplicon is cooling from 95° C. to 60° C. the primer can bind to the appropriate site before interfering structures are formed. In some embodiments, the flow rate of the solution containing the amplicon as it is transferred from the amplification module to the detection module is between about 0.1 µL and about 2 µL. In some embodiments, the flow rate is about 0.1 µL/sec, about 0.2 µL/sec, about 0.3 µL/sec, about 0.4 µL/sec, about 0.5 µL/sec, about 0.6 µL/sec, about 0.7 µL/sec, about 0.8 µL/sec, about 0.9 µL/sec, about 1.0 µL/sec, about 1.1 µL/sec, about 1.2 µL/sec, about 1.3 µL/sec, about 1.4 µL/sec, about 1.5 µL/sec, about 1.6 µL/sec, about 1.7 µL/sec, about 1.8 µL/sec, about 1.9 µL/sec, or about 2.0 µL/sec.

In some embodiments, the methods and device can include a capture probe as described herein. The capture probe is specific for amplicons containing the ciprofloxacin-susceptible gyrA Ser-91 genotype. In silico design tools were used to identify probe candidates. We initially considered linear (simple) probes and molecular inversion probes. A key design goal was the develop a probe that maximizes binding to the ciprofloxacin-susceptible gyrA Ser-91 wild type, while minimizing/eliminating false positives resulting from binding to the gyrA sequence containing the drug resistant SNP. Through numerous design iterations, we concluded that a simple linear probe would provide a suitable degree of specificity, while minimizing design complexity.

In some embodiments, the capture probe hybridization to designed or determined to be on a thermodynamic fulcrum at 52° C. (the default temperature of the amplicon detection flow cell in certain embodiments of the devices of the disclosure) so the match SNP has a $T_m$ below that temperature and the mismatch SNP has a $T_m$ above that temperature. Achieving maximum separation between the match and mismatch TMs is critical to ensure the colorimetric enzymatic reaction provides maximum color for ciprofloxacin-susceptible strains and minimal/no color production for resistant strains. In other embodiments, a capture probe can be characterized by a thermodynamic fulcrum at temperatures either greater than or less than 52° C. For example, in some embodiments, a capture probe can be characterized by a thermodynamic fulcrum at less than 52° C. (e.g., between about 35° C. and 50° C.; between about 38° C. and 45° C., or about 40° C.). In such embodiments, the capture probe could be made with fewer bases, thereby giving the SNP position more of a relative impact. In some embodiments, a method can include modifying the operating temperature of the flow cell (e.g., detection module) based on the thermodynamic fulcrum temperature of the capture probe therein. Such modification can be performed by any suitable mechanism, such as for example, by firmware, software, or hardware.

Figure 5A:
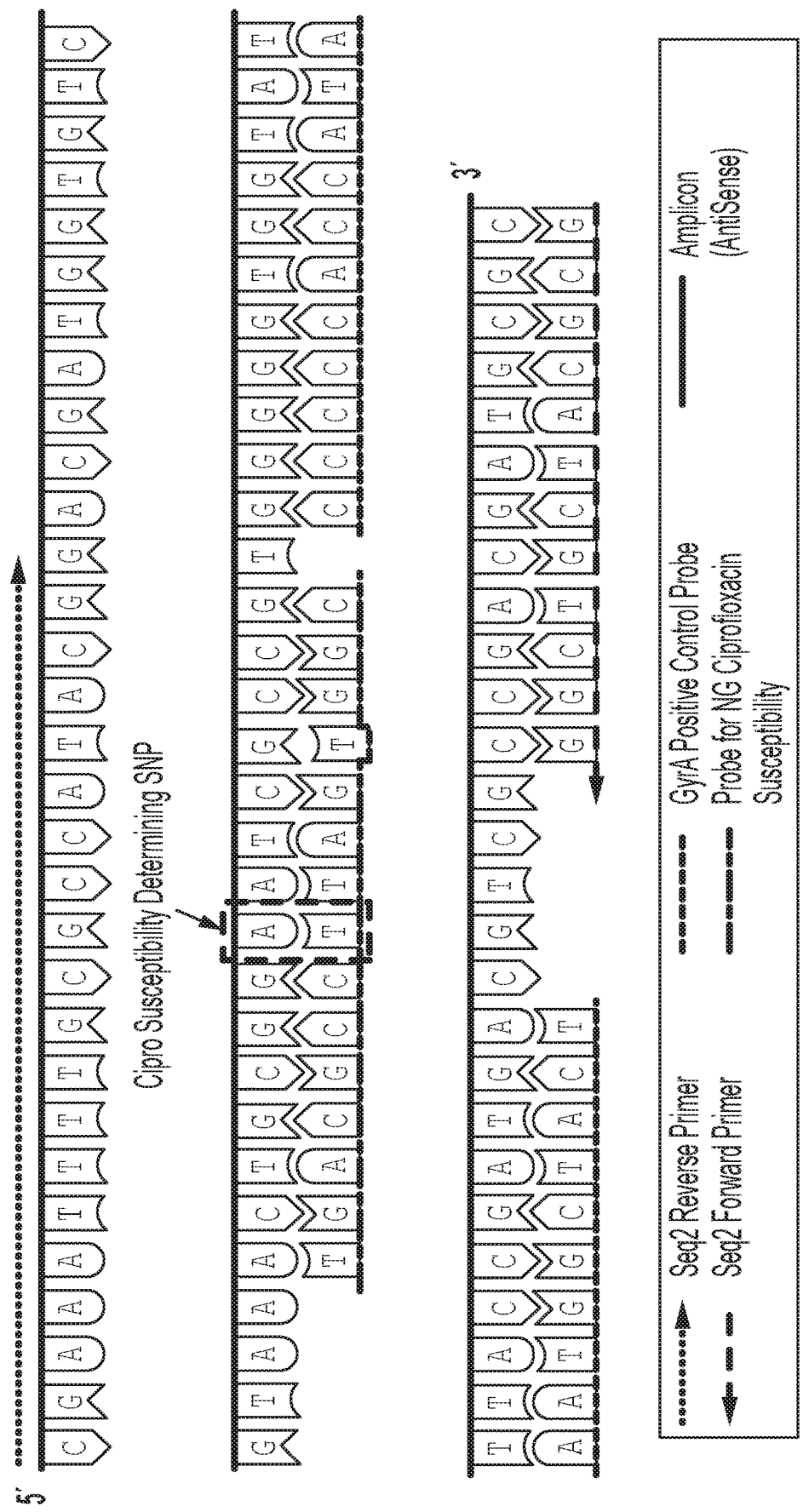
FIG. 5A is a schematic illustration of a primer set, ciprofloxacin susceptibility detection probe, and gyrA positive control, according to an embodiment. The sequences shown are SEQ ID NO: 2-6.

The primer set, ciprofloxacin susceptibility detection probe, and gyrA positive control used are shown in FIG. 5A. In this probe design, in addition to the probe matching the ciprofloxacin-susceptibility determining SNP, an intentional mismatch was created to improve the hybridization kinetics.

A Three-Antibiotic Susceptibility Test

In some embodiments, a method includes determining if a patient is infected with NG, and using the same clinical sample, providing antibiotic susceptibility information for three classes of antibiotics—fluoroquinolones (ciprofloxacin), extended spectrum cephalosporins (cefixime), and the novel spiropyrimidinetrione (zoliflodacin, currently in development). Table 1 shows a clinical treatment algorithm based on all combinations of potential test results. This test is still useful even without ZOL-resistance information (ZOL has yet to be FDA approved) as clinicians will know that the presence of a reduced susceptibility CFX isolate means that the patient can receive 1) recommended dose of CRO+AZI plus follow up with a test of cure one week later; 2) higher dose of CRO+AZI if test of cure is not available; or 3) alternate antibiotics (such as i.v. ertapenem), which was used to treat the patient in the UK with multi-drug resistant NG. By including three antibiotics into the antimicrobial susceptibility test, the time for triple-resistant strains to reach 1% prevalence can be delayed by up to six years, which could provide the much-needed time for development and introduction of new antibiotics to treat NG.

TABLE 1

Three drug treatment algorithm

| Ciprofloxacin (Cip) | Cefixime (Cfx) | Zoliflodacin (Zol) | 3-drug Test Result | Recommended Treatment |
|---|---|---|---|---|
| S | S | S | $Cip^S/Cfx^S/Zol^S$ | Cip |
| S | RS | S | $Cip^S/Cfx^{RS}/Zol^S$ | Cip |
| S | S | R | $Cip^S/Cfx^S/Zol^R$ | Cip |
| S | RS | R | $Cip^S/Cfx^{RS}/Zol^R$ | Cip |
| R | S | S | $Cip^R/Cfx^S/Zol^S$ | Cfx |
| R | RS | S | $Cip^R/Cfx^{RS}/Zol^S$ | Zol |
| R | S | R | $Cip^R/Cfx^S/Zol^R$ | Cfx |
| R | RS | R | $Cip^R/Cfx^{RS}/Zol^R$ | Consultation |

S = susceptible; R = reduced susceptibility; R = resistant

Ciprofloxacin (CIP). CIP is a broad-spectrum fluoroquinolone that inhibits DNA gyrase and topoisomerase IV proteins necessary for bacterial DNA synthesis and repair and thus chromosomal replication. CIP used to be, but is no longer, a CDC-recommended therapy for gonorrhea. According to the CDC, CIP resistance rates hover at ~30%, thus about 389,000 cases of NG in the US in 2017 were infected with CIP-sensitive strains. CIP has been shown to be >99% effective in treating phenotypically susceptible strains even when the infection is located at extra-genital sites. Molecular studies of CIP-susceptible strains show that the absence of a mutation of the wild type Ser91 residue of the gyrase A protein (designated gyrA 91Ser) has been shown to reliably predict susceptibility to CIP. Yet, despite the low cost and efficacy of oral CIP for such strains, nearly all patients with gonorrhea are treated with CRO+AZI. Thus, the current devices and methods allow for the judicious reintroduction of CIP based on molecular antimicrobial susceptibility tests. In this manner, the emergence of CRO-resistant strains can be reduced.

Cefixime (CFX). CFX, like CRO, is a third-generation (extended spectrum) cephalosporin (ESC) that inhibits mucopeptide synthesis in the bacterial cell wall. Although the CDC no longer recommends CFX to treat gonorrhea in the US, CFX remains part of the WHO STD Treatment Guidelines. According to the latest CDC 2018 Surveillance data, the percentage of isolates with elevated cefixime minimum inhibitory concentrations (MICs) (>0.25 ug/ml) declined from 1.4% in 2011 to 0.4% in 2017, while 0.2% of isolates had elevated MICs to CRO. The penA mosaic allele XXXIV has been shown to be sufficient for reduced susceptibility to CFX, whereas additional mutations in the mtrR and porB genes also confer reduced susceptibility to CRO. Thus, in some embodiments, the method includes prescribing CFX for those patients that are susceptible to ESCs (i.e. containing the WT penA gene). In this manner, the use of CRO remains a true last resort antibiotic, thereby slowing the emergence of resistance to CRO. Specifically, if mosaic penA alleles that confer reduced susceptibility (penA XXXIV and related sequences) are detected, then the clinician would have three treatment options: 1) treat with recommended dose of CRO+AZI followed by a test of cure 7 days posttreatment; 2) where follow up test of cure is not possible or unavailable then treat the patient with a higher than recommended dose of CRO+1 g AZI; or 3) treat with an alternate antibiotic like i.v. ertapenem. Moreover, the use of CFX is advantageous because CFX is a single-dose oral antibiotic compared to the more expensive injectable CRO, and will likely be better accepted by patients.

Zoliflodacin (ZOL). ZOL is a novel topoisomerase II inhibitor that appears to have a different mode of action than CIP and is being developed by Entasis Therapeutics to specifically treat gonorrhea. ZOL has demonstrated potent in vitro activity against NG, including against isolates resistant to fluoroquinolones and ESCs, and has shown promising safety and efficacy after a single oral dose in a recent Phase II clinical study (see, e.g., clinicaltrials.gov identifiers NCT02257918 and NCT0340416). Although the frequency of spontaneous resistance was very low in an in vitro study, resistant isolates with three different mutations in the gyrB gene were recovered (D429N, K450T, S467N).

Figure 5B:
FIG. 5B is a photograph of a molecular diagnostic test device that performs a method of a combined test for detection and antibiotic susceptibility, according to an embodiment.

In some embodiments, a diagnostic platform includes a multiplexed assay to simultaneously detect NG in urogenital clinical sample (from men or women) and determine whether the infecting strain of NG is susceptible to ciprofloxacin (CIP), cefixime (CFX), or zoliflodacin (ZOL). Specifically, the platform performs one or more molecular assays to determine if an NG strain is: sensitive to CIP, has reduced susceptibility to CFX, or is resistant to ZOL. The determination can be based on the presence of a particular genotype previously shown to be necessary and sufficient for the corresponding antibiotic susceptibility phenotype, as determined using the agar dilution method. For each of these antibiotic susceptibility genotypes the region of a gene that determines the antibiotic susceptibility phenotype will be amplified and the resulting amplicon exposed to two independent capture probes located in separate positions of the flow cell. One capture probe will hybridize selectively with the sequence within the amplicon that corresponds to the antibiotic susceptibility genotype. If the genotype is present in the amplicon, then hybridization will occur generating a color (e.g., purple) spot as illustrated in FIG. 5B. If the genotype is absent in the amplicon, then hybridization will occur poorly or not at all as indicated by a faint or absent color, as illustrated in FIG. 5B. As a control that the amplicon was successfully amplified, the second capture probe is designed to recognize a conserved sequence in the same amplicon that is present both in antibiotic sensitive and antibiotic resistant NG strains. Successful generation of the amplicon from either antibiotic sensitive or resistant NG strains will be indicated by a color (e.g., purple) spot.

In some embodiments, an assay includes at least one linear capture probes (gyrA Ser91 SNP-specific capture probe and/or gyrA amplicon positive-control capture probe). In some embodiments, primers to a conserved region of the gyrA gene are used to amplify all variants of the resistance determining region of the gene. The resulting amplicon can be captured by the SNP-specific capture probe only if the amplicon contains the exact complementary sequence. In some embodiments, a second control capture probe will capture all variants of the amplicon equally well, i.e., whether it is derived from an antibiotic-resistant or antibiotic sensitive version of the amplicon. The hybridization of the amplicon by the control capture probe denotes successful production of the amplicon and the resulting color intensity provide a basis for computing the color intensity ratio difference between the two capture probes. Thus, in some embodiments, a method can include determining a difference or ratio between the color intensity of the two test spots. The color intensity ratio difference can be used as an input for further methods of determining whether the sample is classified as a SNP-present or SNP-absent result.

In some embodiments, a method includes using bioinformatics tools and a NG penA sequence database to identify primers that amplify the region of the NG penA gene that contains the XXXIV mosaic motif Alterations in the penA gene, which encodes the penicillin-binding protein 2, is a key determinant of susceptibility and resistance to extended spectrum cephalosporins, like CFX and CRO. The penA mosaic XXXIV allele is sufficient for reduced susceptibility to CFX, whereas additional mutations in the mtrR and porB genes also confer reduced susceptibility to CRO. Specifically, at least one study has demonstrated that detection of strains harboring the penA mosaic XXXIV genotype is associated with reduced susceptibility of a gonococcal strain to CFX and CRO with a sensitivity of 98% and 91%, respectively. O. In some embodiments, a real time PCR assay includes PCR primers designed to amplify the penA gene (WT and mosaic) from all NG strains and design capture probes that specifically recognize the penA mosaic XXXIV sequence (and related genotypes) within the penA amplicon.

In some embodiments, a method includes using bioinformatics tools and a NG gyrB sequence database to design, fabricate and test primers that selectively amplify the NG gyrB gene from both ZOL sensitive and ZOL resistant NG strains. In some embodiments, an assay includes at least three capture probes designed to selectively detect the three NG gyrB SNPs that confer resistance to ZOL (D429N, K450T, S467N). Therefore, the presence of even one of these three mutations in the NG gyrB amplicon will result in a color change in the detection flow cell. In addition, an NG gyrB positive control capture probe that corresponds to an invariant region of the gyrB amplicon can be located in a different position of the flow cell. NG gyrB amplicons from ZOL-sensitive and ZOL-resistant NG strains will bind this gyrB amplicon positive control capture probe equally well, indicating that the gyrB amplicon was successfully produced. The color intensity ratio difference between the control capture probe and the D429N or K450T or S467N capture probe will lead via a call algorithm to ZOL resistance present or ZOL resistance absent.

In some embodiments, an assay includes PCR primers and capture probes selected and/or optimized based on the following criteria. 1) SNP detection accuracy (>95% sensitivity and specificity) and 2) Limit of detection (LoD) as determined for genomic DNA from: a) gyrA Ser91 CIPS strains; b) penA CFXRS strain; and c) gyrB ZOLR genetically engineered strains that is equivalent to the LoD of a baseline device (described herein) for detection of NG strains via the opaA amplicon and its capture probe on the flow cells of the integrated STI device. Using the performance of the opaA primer probe set as the standard, the NG LoD for different NG strains is expected to range from 9-114 cfu/ml.

In some embodiments, an optimized multiplexed PCR assay includes five primer pairs designated NS/NG/NGcipS/NGcfxRS/NGrolR. The table below describes the terminology "NS/NG/NGcipS/NGcfxRS/NGrolR." The PCR assay conditions can be selected (and/or optimized) by modulating primer concentration, temperature of the detection chip, wash conditions, and other factors. Thus, the resulting 5-plex assay will have functionality comparable with that for current STI assays (LoD 9-114 cfu/ml) with a PCR efficiency that will not vary >2Ct values.

| NS | *N. subflavca* PCR control primers | Positive Control |
|---|---|---|
| NG | *N. gonorrhoeae* species-specific opaA gene primers | NG detection |
| NG$^{cipS}$ | NG gyrA gene primers | ciprofloxacin susceptibility |
| NG$^{cfxRS}$ | NG mosaic XXXIV penA gene primers | cefixime reduced susceptibility |
| NG$^{zolR}$ | gyrB gene primers | zoliflodacin resistance |

Test Results for a Disposable Molecular Diagnostic Test Device

In some embodiments, any of the methods described herein can be conducted with a single-use, stand-alone molecular diagnostic test device, such as any of those shown and described in International Patent Publication No. WO2016/109691, entitled "Devices and Methods for Molecular Diagnostic Testing," International Patent Publication No. WO2018/005710, entitled "Devices and Methods for the Detection of Molecules Using a Flow Cell," International Patent Publication No. WO2018/005870, entitled "Devices and Methods for Nucleic Acid Extraction," and U.S. patent application Ser. No. 16/186,067, entitled "Portable Molecular Diagnostic Device and Methods for the Detection of Target Viruses," each of which is incorporated herein by reference in its entirety. In some embodiments, a single-use, stand-alone molecular diagnostic test device is capable of detecting clinically-relevant low concentrations of CT (4-36 EB/ml), NG (9-114 cfu/ml), and TV (2-6 trophozoites/ml). Moreover, the device can amplify the CT, NG, and TV DNA templates with ≥90% efficiency, including amplification during multiplexed amplification. In this manner, the device (and methods performed thereon) can have an excellent limit of detection that is clinically relevant. For example, in some embodiments, methods and devices can produce limit of detection (LoD) values for CT, NG and TV from single-target samples of approximately 5 EB/ml, 18 cfu/ml, and 2 troph/ml. In other embodiments, methods and devices according to an embodiment have been shown to produce limit of detection (LoD) values for CT, NG and TV from single-target samples of approximately 5.25 EB/ml and 0.39 cfu/ml. In yet other embodiments, methods and devices according to an embodiment could produce limit of detection (LoD) values for TV as low as 0.2 troph/ml.

Figure 6:
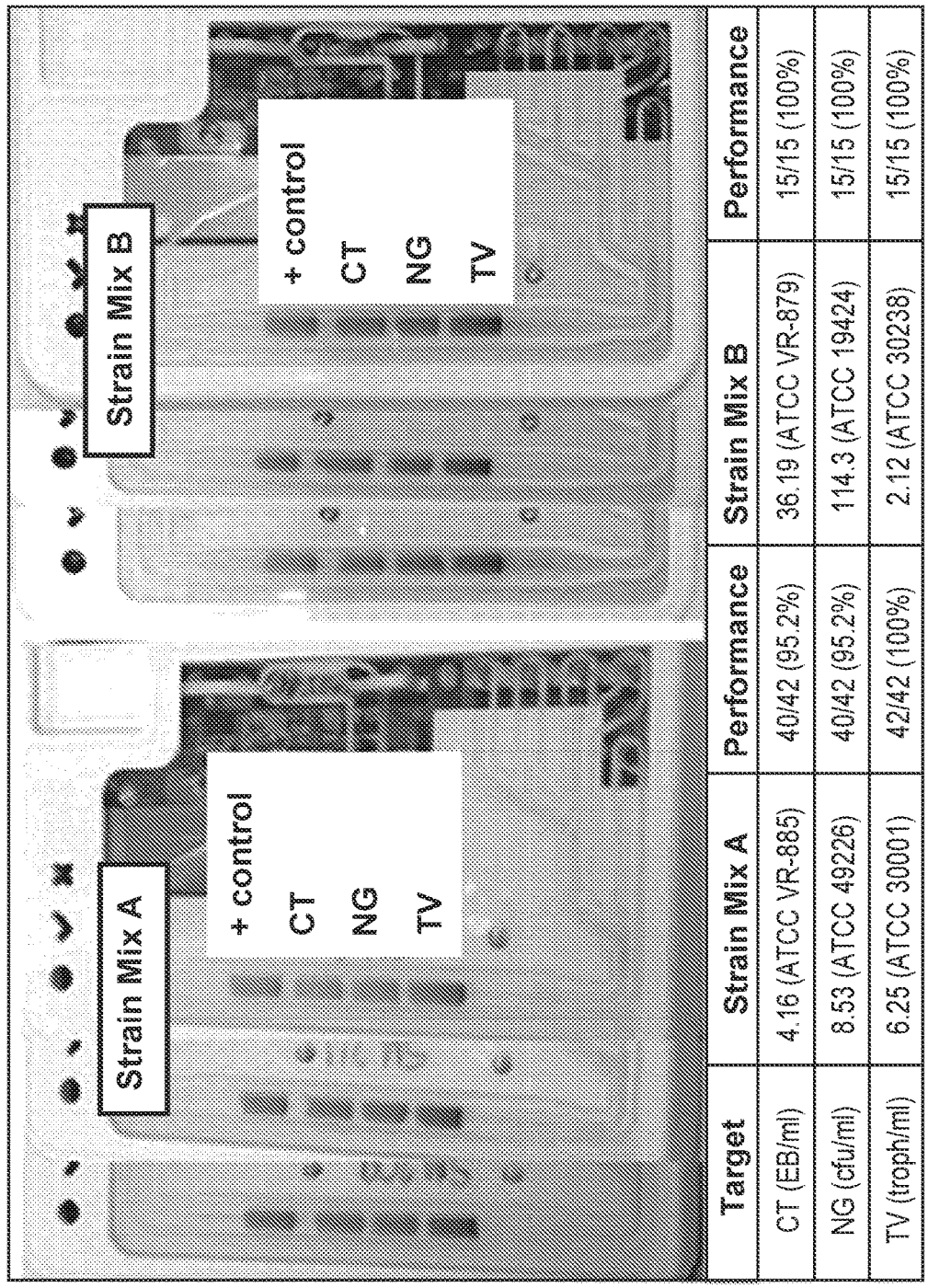
FIG. 6 are photographs showing test results performed for preliminary Limit of Detection (LoD) determination.

Specifically, FIG. 6 shows a photograph of test results conducted on a molecular diagnostic test device, according to an embodiment. Tests were conducted with a multiplex reaction across a total of 60 devices spanning three lots (20 devices per lot). To evaluate inclusivity of the device, diverse secondary strains of the same three species (70 NG, 16 CT, and 31 TV strains) were tested with strains of the target organisms other than the two primary strains tested in the LoD study. Samples were created that were double-target samples (either CT+NG or TV+NG) at 3×LoD and tested in duplicate. This inclusivity testing demonstrated that the selected PCR primer sets can detect all the secondary strains tested (data not shown).

To evaluate the cross-reactivity of the device, 32 phylogenetically related non-STI organisms (i.e., our "nearest neighbor" exclusivity list of species) were tested in the presence and absence CT, NG, and TV. Samples were tested with pools of 8 organisms per pool at approximate concentrations of 1,000,000 organisms/mL each. Samples containing 2×LoD of CT, NG, and TV were spiked with these "nearest-neighbor" pools and tested in triplicate. The test results demonstrated that only the three target organisms (NG, CT, or TV) were amplified; none of the phylogenetically related non-STI organisms were amplified using the CT, NG, or TV primer sets (data not shown).

Figure 7:
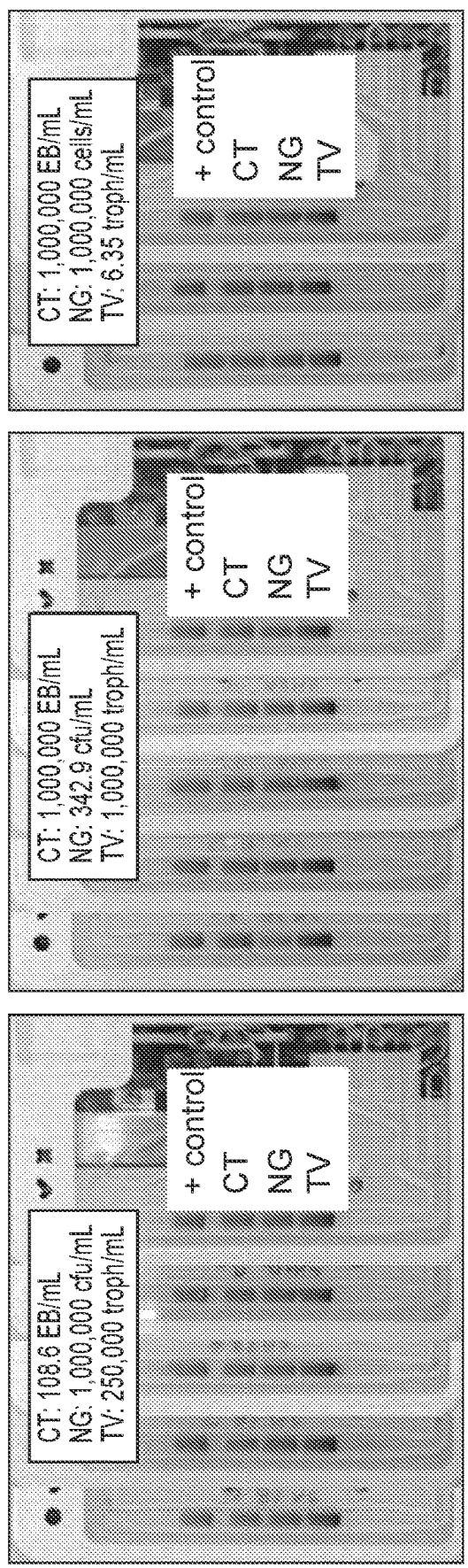
FIG. 7 are photographs showing test results performed to evaluate competitive inhibition.

In some embodiments a multiplex test device and/or methods can ensure that the presence of one pathogen does not produce a false negative result for another pathogen in the same sample. FIG. 7 shows photographs of test results from tests in which samples containing all three target organisms were made where two target organisms were at high concentrations and the third was at 3× the LoD. Each of these combinations was tested in triplicate over three lots of devices. The device successfully identified the spiked pathogen in the sample despite a significant difference in pathogen concentrations. For all combinations, the pathogen present at a low concentration (3×LoD) was easily detected in the presence of the other two pathogens present at high concentrations.

In some embodiments, any of the devices and methods described herein can be conducted on a variety of different types of samples. Such sample types can include, for example, vaginal swab, penile meatal swab sample, urine sample, rectal swab sample and/or pharyngeal swab sample. A series of tests was performed with vaginal swab samples.

The first test assessed samples collected by clinicians where patients from a single site were enrolled in the study after a "callback" from an initial positive result from a FDA-approved comparator device (Call-back Study). The other assessed self-collected vaginal swab samples that included both symptomatic and asymptomatic patients (n=400) from three different sites (Beta Study) distributed across the US. The Beta Study informed and preceded the 1,700 patient, 4-6 month ongoing pivotal clinical trial. In addition, archived vaginal (30 samples for CT and NG) and endocervical swabs (8 samples for CT and 18 samples for NG) were also assessed. Each Click device result was compared against the patient infected status as determined by 2 to 3 FDA-approved NAAT comparator instruments. If two comparators were used, and the results were discordant, that sample was excluded from analysis. Where three comparators were used, results from at least 2 out of 3 comparators had to match to determine the patient infected status (PIS). Test results are shown in Table 2, below. The instruments used to compare results were Aptima, BDMax, and BDProbeTec. The table below represents a summary of all preclinical studies—beta, call-back, and archived swab (vaginal and endocervical) samples.

TABLE 2

Sensitivity and Specificity Analysis from Clinical Feasibility Studies.

| | | Comparator | | | | | |
|---|---|---|---|---|---|---|---|
| | | Positive | Negative | Total | Sensitivity | Specificity | Prevalence |
| CT | | | | | | | |
| Click | Positive | 73 | 1 | 74 | 98.65% | 99.65% | 20.44% |
| | Negative | 1 | 287 | 288 | | | |
| | Total | 74 | 288 | 362 | | | |
| NG | | | | | | | |
| Click | Positive | 57 | 2 | 59 | 100.005 | 99.40% | 14.69% |
| | Negative | 0 | 329 | 329 | | | |
| | Total | 57 | 331 | 388 | | | |
| TV | | | | | | | |
| Click | Positive | 52 | 16* | 68 | 100.00% | 94.01%** | 16.30% |
| | Negative | 0 | 251 | 251 | | | |
| | Total | 52 | 267 | 319 | | | |

Any of the sample input modules, sample preparation modules, amplification modules, heater assemblies, and detection modules shown and described herein can be used in any suitable diagnostic device. Such devices can include, for example, a single-use device that can be used in a point-of-care setting and/or in a user's home. Similarly stated, in some embodiments, the device (and any of the other devices shown and described herein) can be configured for use in a decentralized test facility. Further, in some embodiments, any of the sample input modules, sample preparation modules, amplification modules, heater assemblies, and detection modules shown and described herein can be included within a CLIA-waived device and/or can facilitate the operation of a device in accordance with methods that are CLIA waived. Similarly stated, in some embodiments, the sample input modules, the sample preparation modules, the amplification modules, and the detection modules shown and described herein can facilitate operation of a device in a sufficiently simple manner that can produce results with sufficient accuracy to pose a limited likelihood of misuse and/or to pose a limited risk of harm if used improperly. In some embodiments, the sample input modules, the sample preparation modules, the amplification modules, and the detection modules shown and described herein can be used in any of the diagnostic devices shown and described in International Patent Publication No. WO2016/109691, entitled "Devices and Methods for Molecular Diagnostic Testing," which is incorporated herein by reference in its entirety.

Although the amplification modules are generally described herein as performing a thermal cycling operation on the prepared solution, in other embodiment, an amplification module can perform any suitable thermal reaction to amplify nucleic acids within the solution. In some embodiments, any of the amplification modules described herein can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process The devices and methods described herein can be used to analyze any suitable type of biological sample, such as a tissue sample (e.g., a blood sample). In some cases, the biological sample comprises a bodily fluid taken from a subject. In some cases, the bodily fluid includes one or more cells comprising nucleic acids. In some cases, the one or more cells comprise one or more microbial cells, including, but not limited to, bacteria, archaebacteria, protists, and fungi. In some cases, the biological sample includes one or more virus particles. In some cases, the biological sample includes one or more microbes that causes a sexually-transmitted disease. A sample may comprise a sample from a subject, such as whole blood; blood products; red blood cells; white blood cells; buffy coat; swabs; urine; sputum; saliva; semen; lymphatic fluid; endolymph; perilymph; gastric juice; bile; mucus; sebum; sweat; tears; vaginal secretion; vomit; feces; breast milk; cerumen; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may include cells of a primary culture or a cell line. Examples of cell lines include, but are not limited to 293-T human kidney cells, A2870 human ovary cells, A431 human epithelium, B35 rat neuroblastoma cells, BHK-21 hamster kidney cells, BR293 human breast cells, CHO Chinese hamster ovary cells, CORL23 human lung cells, HeLa cells, or Jurkat cells. The sample may include a homogeneous or mixed population of microbes, including one or more of viruses, bacteria, protists, monerans, chromalveolata, archaea, or fungi. The biological sample can be a urine sample, a vaginal swab, a cervical swab, an anal swab, or a cheek swab. The biological sample can be obtained from a hospital, laboratory, clinical or medical laboratory.

In some embodiments, a method includes detecting, from a sample, an infecting microbe and a SNP that is associated with (or that determines) the antimicrobial susceptibility. Such samples can include, for example, blood, urine, sputum, cerebral spinal fluid, joint fluid, feces, pus, tissue, and swabs from urogenital sites, rectum, pharynx (and nasal pharynx), and conjunctivae.

The devices and methods described herein, however, are not limited to performing a molecular diagnostic test on human samples. In some embodiments, any of the devices and methods described herein can be used with veterinary samples, food samples, and/or environmental samples. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Examples of subjects from which polynucleotides may be isolated include multicellular organisms, such as fish, amphibians, reptiles, birds, and mammals. Examples of mammals include primates (e.g., apes, monkeys, gorillas), rodents (e.g., mice, rats), cows, pigs, sheep, horses, dogs, cats, or rabbits. In some examples, the mammal is a human. Further, the sample of the present invention is not limited to biological samples, the sample of the present invention may be environmental (air, water, soil, etc.), animal (see above), or plant (e.g., cells obtained from any portion of a plant where the species of plant is without limit).

In some embodiments, the sample is a processed or unprocessed food product. In other aspects, the food sample comprises at least one of meat, turkey, chicken and other poultry, milk, eggs, eggs products, dairy products, fresh or dried fruits and vegetables and their juices, grains, fish, seafood, pet food, baby food and infant formula. In another embodiment, the sample is a bacterial isolate, to confirm or identify the strain and its antibacterial resistance profile. It is anticipated that the organism-specific and antibiotic resistance (AR) probes in an array system can be used as a clinical diagnostics tool in hospitals, to aid in epidemiological research and tracking as well as for infection control.

In some embodiments, any of the amplification modules described can be configured to conduct a "rapid" PCR (e.g., completing at least 30 cycles in less than about 10 minutes), and rapid production of an output signal (e.g., via a detection module). Similarly stated, the amplification modules described herein can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

In some embodiments, any of the devices and methods described herein can be a "rapid" PCR (e.g., completing at least 30 cycles in less than about 10 minutes) that provides sample-to-answer capability, without the need for an external instrument, in about 27 minutes, 25 minutes, 22 minutes, 20 minutes, or less. Similarly stated, the device can be a stand-alone device that does not require any external instrument to add reagents, manipulate actuators, mix constituents, or read the test result. In some embodiments, the device can be connected to an external power source (e.g., an A/C power source, which is not considered to be an "external instrument.").

In some embodiments, any of the devices and methods described herein (and the methods can be performed rapidly: an integrated sample-to-result requiring only 10 to 15 seconds of hands-on time, giving a test result in less than about 25 minutes. The device and methods described herein are accurate and use the same PCR technology as market leading laboratory-based systems. The device and methods described herein allow for simultaneous detection of multiple pathogens. The device and methods described herein are single-use/disposable tests that eliminate instrument cleaning, servicing, and decontamination. The device and methods described herein are applicable for unlimited surge testing—one or many tests can be performed simultaneously/asynchronously.

In some embodiments, any of the devices described herein can be shelf-stable. Specifically, the devices described herein can have no special temperature or humidity requirements for transport and storage, thus easing stockpiling.

Any of the devices described herein can be easily and portably powered. Any of the devices can be powered by a wall adapter or battery, and are thus ideal for field use.

In some embodiments, a method of detection of NG and other STI's can be performed on a stand-alone device. The device is configured to detect (and the method includes detection of) all FDA required strains (70 strains of NG, 16 strains of CT, and 31 strains of TV). Moreover, the device (and the methods) have no cross-reactivity against 142 strains of phylogenetically related non-STI organisms typically found in the urogenital tract. The device is capable of, and the methods include detection of low concentrations of CT (50-150 EB/ml), NG (50-150 cfu/ml), and TV (20 trophs/ml) typically found in patients with low microbial loads. For example, certain test results from 79 patient samples containing CT or NG, and 78 samples containing TV showed a sensitivity of 100% across all pathogens, and a specificity of 98% for CT and NG, and 94% for TV as compared to an FDA-approved NAAT device performed at a Planned Parenthood clinic.

Although the methods are described herein as being applicable to testing for STI's in other embodiments, the devices and methods described herein can be used to detect any infectious disease. For example, the methods and devices described herein can be used for detection of SNPs in bacteria, viruses, fungi, protozoa that confer resistance or susceptibility to antimicrobials and therefore which guide selection of the most effective medicine. Other methods can include the use of SNPs to genotype infecting microbes as companion or complementary diagnostics to accelerate clinical trials of new antimicrobials Any of the devices, compositions, and methods described herein can be used in connection with the diagnosis and/or treatment of any applicable disease, disorder, or condition.

For example, in some embodiments, any of the devices, compositions, and methods described herein can be used to detect SNPs in tissue biopsies and/or blood to genotype cancers for diagnosis, prognostication, treatment (selection of optimal cancer drugs and biologicals), and/or to detect recurrence. In some embodiments, a method can include detection of SNPs to determine (or quantify) a hereditary risk of cancer. In some embodiments, a method can include modifying a treatment protocol in response to the detection. Similarly stated, in some embodiments, a method can include intensified screening (e.g., more frequent colonoscopies or mammograms) in response to the detected SNP.

In some embodiments, a method can include detection of SNPs in human DNA to determine (or quantify) the efficacy of a drug for treatment of an indication. Similarly stated, the methods described herein can be used to determine the effectiveness of a particular drug for a particular patient. In particular, because the SNP can affect drug metabolism (and thus drug dosing), the result can be used to predict an adverse reaction, or has prognostic significance, the methods described herein can be used as a part of a personalized medicine protocol to prescribe a drug and/or dosing regimen.

In some embodiments, a method can include detection of SNPs in maternal blood or amniotic fluid. In this manner, the method can include predicting or quantifying a risk profile for a fetus (e.g., to assess the risk for developmental abnormalities).

Although the methods have been described herein as being applicable to diagnostics, treatment, or other health care applications, in other embodiments, any of the devices, compositions, and methods described herein can be used for any suitable purposes, including food safety, agriculture, environmental preservation, and forensic applications. For example, in some embodiments, any of the devices, compositions, and methods described herein can be used to determine if a crime scene sample is genotypically identical to samples from a list of persons of interest. In other embodiments, any of the devices, compositions, and methods described herein can be used for genotyping to determine if two persons are genetically related, including for paternity assignment purposes.

ENUMERATED EMBODIMENTS

Embodiment Set I

Embodiment I-1

A molecular diagnostic device, comprising a sample preparation module configured to receive a biological sample; a reagent module containing a primer set designed to target a gyrA region; an amplification module including a reaction volume and a heater, the reaction volume configured to receive the biological sample and the primer set amplification solution, the heater configured to convey thermal energy into the reaction volume to amplify the gyrA region to produce an output containing a target amplicon; and a detection module configured to receive the target amplicon, the detection module including a probe designed to maximize binding to a drug-susceptible portion of the target amplicon while minimizing binding to a drug-resistant portion of the target amplicon.

Embodiment I-2

The molecular diagnostic device of Embodiment I-1, wherein the primer set is designed to flank the gyrA 91 locus.

Embodiment I-3

The molecular diagnostic device of Embodiment I-2, wherein a length of the gyrA region flanked by the primer set is between about 60 and about 140 base pairs.

Embodiment I-4

The molecular diagnostic device of Embodiment I-3, wherein a length of the gyrA region flanked by the primer set is between about 80 and about 120 base pairs.

Embodiment I-5

The molecular diagnostic device of Embodiment I-2, wherein a length of the gyrA region flanked by the primer set includes a secondary structure.

Embodiment I-6

The molecular diagnostic device of Embodiment I-1, wherein the probe is designed to maximize binding to the wild type, ciprofloxacin-sensitive gyrA Ser-91 genotype while minimizing binding to other SNPs at the gyrA Ser-91 site that confer a drug resistance.

Embodiment I-7

The molecular diagnostic device of Embodiment I-3, wherein the probe is characterized by a thermodynamic fulcrum of about 52° C.

Embodiment I-8

A method, comprising amplifying a first gene to produce a first target amplicon associated with a target bacteria; amplifying a second gene to produce a second target amplicon associated a drug resistant mutation; reacting the first target amplicon with a first probe to produce a first signal indicating a presence of the target bacteria; and reacting the second target amplicon with a second probe to produce a second signal indicating that the target bacteria is susceptible to a drug.

Embodiment I-9

The method of Embodiment I-8, wherein the amplifying the first gene and the amplifying the second gene are performed simultaneously within a stand-alone device.

Embodiment I-10

The method of Embodiment I-8, wherein the second signal is produced without performing any melting curve analysis.

Embodiment I-11

The method of Embodiment I-8, wherein the target bacteria is *Neisseria* gonorrheae (NG); the second gene is the gyrA gene of NG; the amplifying the gyrA gene includes: mixing a biological sample with a primer set designed to target a gyrA region; and thermal cycling the mixture of the biological sample and the primer set between a first temperature and a second temperature at a rate sufficient to produce the first target amplicon and the second target amplicon.

Embodiment I-12

A method, comprising performing a molecular diagnostic test on a biological sample to determine A) the presence of a target bacteria and B) the presence of a gene mutation within the target bacteria that confers resistance to a first antibiotic; and prescribing, based on a result of the molecular diagnostic test, a second antibiotic.

Embodiment I-13

The method of Embodiment I-12, wherein the target bacteria is *Neisseria* gonorrheae (NG); and the gene mutation is a single-nucleotide polymorphism.

Embodiment I-14

The molecular diagnostic device of Embodiment I-2, wherein a length of the gyrA region flanked by the primer set is between about 20 and about 240 base pairs.

Embodiment I-15

The molecular diagnostic device of Embodiment I-14, wherein a length of the gyrA region flanked by the primer set is between about 20 and about 60 base pairs.

Embodiment I-16

The molecular diagnostic device of Embodiment I-14, wherein a length of the gyrA region flanked by the primer set is between about 140 and about 240 base pairs.

Embodiment Set II

Embodiment II-1

A molecular diagnostic device, comprising:
- a sample preparation module configured to receive a biological sample, wherein the biological sample comprises a polynucleotide;
- a reagent module containing a primer set targeting a single nucleotide polymorphism (SNP) locus in the polynucleotide;
- an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and
- a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele.

Embodiment II-2

The molecular diagnostic device of Embodiment II-1, wherein the primer set is designed to flank the SNP locus.

Embodiment II-3

The molecular diagnostic device of Embodiment II-2, wherein a length of a target region flanked by the primer set is between about 60 and about 140 base pairs.

Embodiment II-4

The molecular diagnostic device of Embodiment II-3, wherein a length of a target region flanked by the primer set is between about 80 and about 120 base pairs.

Embodiment II-5

The molecular diagnostic device of any one of Embodiments II-1 to II-4, wherein the target amplicon comprises minimal secondary structure.

Embodiment II-6

The molecular diagnostic device of any one of Embodiments II-1 to II-5, wherein the primer set designed to target a SNP locus comprises:
i) an upstream oligonucleotide primer substantially complementary to an upstream primer binding site at the 5' terminus of the target region on the antisense strand; and
ii) a downstream oligonucleotide primer substantially complementary to a downstream primer binding site at the 3' terminus of the target region on the sense strand.

Embodiment II-7

The molecular diagnostic device of any one of Embodiments II-1 to II-6, wherein the molecular diagnostic device comprises a temperature controller configured to maintain the temperature of the detection module at about 5° C., about 10° C., or about 15° C. less than the melting temperature of the first probe.

Embodiment II-8

The molecular diagnostic device of any one of Embodiments II-1 to II-7, wherein the detection module comprises a temperature controller configured to maintain a predetermined temperature for the detection module, and wherein the first probe is designed to have a melting temperature at about 5° C., about 10° C., or about 15° C. less than the predetermined temperature.

Embodiment II-9

The molecular diagnostic device of any one of Embodiments II-1 to II-8, wherein the probe is substantially complementary to a probe binding site comprising the SNP locus, and comprises a nucleotide matched the target allele.

Embodiment II-10

The molecular diagnostic device of any one of Embodiments II-1 to II-9, wherein the probe comprises at most two nucleotide mismatches to the probe binding site.

Embodiment II-11

The molecular diagnostic device of any one of Embodiments II-1 to II-10, wherein the probe is perfectly complementary to the probe binding site.

Embodiment II-12

The molecular diagnostic device of any one of Embodiments II-1 to II-11, wherein the probe does not overlap the primer set design to target the SNP locus.

Embodiment II-13

The molecular diagnostic device of any one of Embodiments II-1 to II-12, wherein the detection module comprises a second probe substantially complementary to a second probe binding site, wherein the second probe binding site does not comprise the SNP locus.

Embodiment II-14

The molecular diagnostic device of Embodiment II-13, wherein the second probe binding site does not overlap the binding site of the first probe.

Embodiment II-15

The molecular diagnostic device of any one of Embodiments II-1 to II-12, wherein the detection module comprises a second probe substantially complementary to a second probe binding site within the target amplicon, wherein the second probe binding site does not overlap the binding site of the first probe.

Embodiment II-16

The molecular diagnostic device of any one of Embodiments II-1 to II-15, wherein the target allele is a drug-resistance allele.

Embodiment II-17

The molecular diagnostic device of any one of Embodiments II-1 to II-16, wherein the molecular diagnostic device specifically detects the drug-resistance allele in the biological sample.

Embodiment II-18

The molecular diagnostic device of any one of Embodiments II-1 to II-15, wherein the allele is a drug-sensitivity allele.

Embodiment II-19

The molecular diagnostic device of any one of Embodiments II-1 to II-15 or Embodiment II-18, wherein the molecular diagnostic device specifically detects the drug-resistance allele in the biological sample.

Embodiment II-20

The molecular diagnostic device of any one of Embodiments II-1 to II-19, wherein the SNP locus is within a gyrA region.

Embodiment II-21

The molecular diagnostic device of any one of Embodiments II-1 to II-20, wherein the primer set is designed to flank the gyrA 91 locus.

Embodiment II-22

The molecular diagnostic device of Embodiment II-21, wherein a length of the gyrA region flanked by the primer set is between about 60 and about 140 base pairs.

Embodiment II-23

The molecular diagnostic device of Embodiment II-22, wherein a length of the gyrA region flanked by the primer set is between about 80 and about 120 base pairs.

Embodiment II-24

The molecular diagnostic device of any one of Embodiments II-21 to II-23, wherein a length of the gyrA region flanked by the primer set includes a secondary structure.

Embodiment II-25

The molecular diagnostic device of any one of Embodiments II-1 to II-24, wherein the first probe is designed to maximize binding to the wild type, ciprofloxacin-sensitive gyrA Ser-91 genotype while minimizing binding to other SNPs at a gyrA Ser-91 site that confers a drug resistance.

Embodiment II-26

The molecular diagnostic device of any one of Embodiments II-1 to II-25, wherein the first probe is substantially complementary to a first probe binding site comprising the codon encoding gyrA Ser-91, and wherein the first probe comprises a nucleotide that matches an allele encoding ciprofloxacin-sensitive gyrA Ser-91 genotype.

Embodiment II-27

The molecular diagnostic device of any one of Embodiments II-1 to II-26, wherein the first probe discriminates between an allele encoding the ciprofloxacin-sensitive gyrA Ser-91 genotype and the antiallele encoding the gyrA Phe-91 site that confers resistance to ciprofloxacin.

Embodiment II-28

The molecular diagnostic device of any one of Embodiments II-1 to II-27, wherein the first probe is characterized by a thermodynamic fulcrum and/or melting temperature of about 52° C.

Embodiment II-29

The molecular diagnostic device of any one of Embodiments II-1 to II-28, wherein the first probe comprises between 12 and 25 nucleotides.

Embodiment II-30

The molecular diagnostic device of Embodiment II-29, wherein the first probe comprises between 18 and 22 nucleotides.

Embodiment II-31

The molecular diagnostic device of any one of Embodiments II-1 to II-30, wherein the first probe has a melting temperature of between 50° C. and 60° C.

Embodiment II-32

The molecular diagnostic device of any one of Embodiments II-1 to II-31, wherein the first probe comprises, consists essentially of, or consists of a sequence selected from any one of SEQ ID NO: 14-20.

Embodiment II-33

The molecular diagnostic device of any one of Embodiments II-1 to II-32, wherein the second probe comprises between 12 and 25 nucleotides.

Embodiment II-34

The molecular diagnostic device of Embodiment II-33, wherein the second probe comprises between 18 and 22 nucleotides.

Embodiment II-35

The molecular diagnostic device of any one of Embodiments II-1 to II-34, wherein the second probe has a melting temperature of between 50° C. and 60° C.

Embodiment II-36

The molecular diagnostic device of any one of Embodiments II-1 to II-35, wherein the second probe comprises, consists essentially of, or consist of a sequence selected from any one of SEQ ID NO: 6 or 22.

Embodiment II-36

The molecular diagnostic device of any one of Embodiments II-1 to II-34, wherein the molecular diagnostic device detects the allele in a biological sample comprising at least about 0.5 nM, at least about 1 nM, at least about 1.5 nM, at least about 2 nM, at least about 6 nM, at least about 8 nM, at least about 10 nM, or at least about 15 nM of the polynucleotide comprising the SNP locus if the SNP locus comprises the allele.

Embodiment II-37

The molecular diagnostic device of any one of Embodiments II-1 to II-36, wherein the molecular diagnostic device determines whether a subject suspected of having a drug-sensitive bacterial infection has a drug-sensitive bacterial infection.

Embodiment II-38

The molecular diagnostic device of any one of Embodiments II-1 to II-37, wherein the molecular diagnostic device determines whether a subject suspected of having a drug-resistant bacterial infection has a drug-resistant bacterial infection.

Embodiment II-39

A method, comprising:
a) introducing into the molecular diagnostic device of any one of Embodiments II-1 to 11-38 a biological sample from a subject having or suspected of having a disease or disorder characterized by one or more SNPs associated with susceptibility to a treatment, wherein the biological sample comprising a polynucleotide from the subject,
b) administering the treatment if the molecular diagnostic device indicates the polynucleotide comprises a SNP locus comprising an allele associated with susceptibility to the treatment.

Embodiment II-40

The method of Embodiment II-39, wherein the disease or disorder is a bacterial infection.

Embodiment II-38

A method, performed in a molecular diagnostic device comprising:
a sample preparation module configured to receive a biological sample, wherein the biological sample comprises a polynucleotide from a target bacteria;
a reagent module containing a primer set targeting a single nucleotide polymorphism (SNP) locus in the polynucleotide;
an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and
a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele;
the method comprising:
amplifying a target amplicon from the polynucleotide from the target bacteria;
optionally, amplifying a second target amplicon from the polynucleotide from the target bacteria;
reacting the first target amplicon with a first probe to produce a first signal indicating susceptibility of the target bacteria to drug;
optionally, reacting the first target amplicon with a second probe to produce a second signal indicating presence of the target bacteria in the biological sample and/or amplification of the target amplicon; and
optionally, reacting the second target amplicon with a third probe to produce a third signal indicating presence of the target bacteria in the biological sample and/or amplification of either or both of the first target amplicon and the second target amplicon.

Embodiment II-42

The method of Embodiment II-41, wherein the amplifying the first gene and the amplifying the second gene are performed simultaneously within a stand-alone device.

Embodiment II-43

The method of Embodiment II-41 or Embodiment II-42, wherein the first signal, second signal, and/or third signal are produced without performing any melting curve analysis.

Embodiment II-44

The method of any one of Embodiments II-41 to II-43, wherein:
the target bacteria is *Neisseria* gonorrheae (NG);
the SNP locus is within the gyrA gene of NG;
the amplifying the target amplicon comprises:
mixing a biological sample with a primer set designed to target a gyrA region; and
thermal cycling the mixture of the biological sample and the primer set between a first temperature and a second temperature at a rate sufficient to produce the first target amplicon and optionally the second target amplicon.

Embodiment II-45

A method, performed in a molecular diagnostic device comprising:
a sample preparation module configured to receive a biological sample, wherein the biological sample comprises a polynucleotide from a target bacteria;
a reagent module containing a primer set targeting a single nucleotide polymorphism (SNP) locus in the polynucleotide;
an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and
a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele;
the method comprising:
performing a molecular diagnostic test on the biological sample to determine A) the presence of a target bacteria and B) the presence of the target allele within the target bacteria that confers resistance to a first antibiotic; and
administering, based on a result of the molecular diagnostic test, a second antibiotic.

Embodiment II-46

The method of Embodiment II-46, wherein the target bacteria is *Neisseria* gonorrheae (NG).

Embodiment II-47

The method of any one of Embodiments II-42 to II-46, wherein the primer set is designed to flank the SNP locus.

Embodiment II-48

The method of any one of Embodiments II-42 to II-47, wherein a length of a target region flanked by the primer set is between about 60 and about 140 base pairs.

Embodiment II-49

The method of any one of Embodiments II-42 to II-48, wherein a length of a target region flanked by the primer set is between about 80 and about 120 base pairs.

Embodiment II-50

The method of any one of Embodiments II-42 to II-49, wherein the target amplicon comprises minimal secondary structure.

Embodiment II-51

The method of any one of Embodiments II-42 to II-50, wherein the primer set designed to target a SNP locus comprises:
 i) an upstream oligonucleotide primer substantially complementary to an upstream primer binding site at the 5' terminus of the target region on the antisense strand; and
 ii) a downstream oligonucleotide primer substantially complementary to a downstream primer binding site at the 3' terminus of the target region on the sense strand.

Embodiment II-52

The method of any one of Embodiments II-42 to II-51, wherein the method comprises a temperature controller configured to maintain the temperature of the detection module at about 5° C., about 10° C., or about 15° C. less than the melting temperature of the first probe.

Embodiment II-53

The method of any one of Embodiments II-42 to II-52, wherein the detection module comprises a temperature controller configured to maintain a predetermined temperature for the detection module, and wherein the first probe is designed to have a melting temperature at about 5° C., about 10° C., or about 15° C. less than the predetermined temperature.

Embodiment II-54

The method of any one of Embodiments II-42 to II-53, wherein the probe is substantially complementary to a probe binding site comprising the SNP locus, and comprises a nucleotide matched the target allele.

Embodiment II-55

The method of any one of Embodiments II-42 to II-54, wherein the probe comprises at most two nucleotide mismatches to the probe binding site.

Embodiment II-56

The method of any one of Embodiments II-42 to II-55, wherein the probe is perfectly complementary to the probe binding site.

Embodiment II-57

The method of any one of Embodiments II-42 to II-56, wherein the probe does not overlap the primer set design to target the SNP locus.

Embodiment II-58

The method of any one of Embodiments II-42 to II-57, wherein the detection module comprises a second probe substantially complementary to a second probe binding site, wherein the second probe binding site does not comprise the SNP locus.

Embodiment II-59

The method of Embodiment II-58, wherein the second probe binding site does not overlap the binding site of the first probe.

Embodiment II-60

The method of any one of Embodiments II-42 to II-57, wherein the detection module comprises a second probe substantially complementary to a second probe binding site within the target amplicon, wherein the second probe binding site does not overlap the binding site of the first probe.

Embodiment II-61

The method of any one of Embodiments II-42 to II-60, wherein the target allele is a drug-resistance allele.

Embodiment II-62

The method of any one of Embodiments II-42 to II-61, wherein the method specifically detects the drug-resistance allele in the biological sample.

Embodiment II-63

The method of any one of Embodiments II-42 to II-60, wherein the allele is a drug-sensitivity allele.

Embodiment II-64

The method of any one of Embodiment II-42 to II-60 or Embodiment II-63, wherein the method specifically detects the drug-resistance allele in the biological sample.

Embodiment II-65

The method of any one of Embodiments II-42 to II-64, wherein the SNP locus is within a gyrA region.

Embodiment II-66

The method of any one of Embodiments II-42 to II-65, wherein the primer set is designed to flank the gyrA 91 locus.

Embodiment II-67

The method of Embodiment II-66, wherein a length of the gyrA region flanked by the primer set is between about 60 and about 140 base pairs.

Embodiment II-68

The method of Embodiment II-67, wherein a length of the gyrA region flanked by the primer set is between about 80 and about 120 base pairs.

Embodiment II-69

The method of any one of Embodiments II-66 to II-68, wherein a length of the gyrA region flanked by the primer set includes a secondary structure.

Embodiment II-70

The method of any one of Embodiments II-42 to II-69, wherein the first probe is designed to maximize binding to the wild type, ciprofloxacin-sensitive gyrA Ser-91 genotype while minimizing binding to other SNPs at a gyrA Ser-91 site that confers a drug resistance.

Embodiment II-71

The method of any one of Embodiments II-42 to II-70, wherein the first probe is substantially complementary to a first probe binding site comprising the codon encoding gyrA Ser-91, and wherein the first probe comprises a nucleotide that matches an allele encoding ciprofloxacin-sensitive gyrA Ser-91 genotype.

Embodiment II-72

The method of any one of Embodiments II-42 to II-71, wherein the first probe discriminates between an allele encoding the ciprofloxacin-sensitive gyrA Ser-91 genotype and the antiallele encoding the gyrA Phe-91 site that confers resistance to ciprofloxacin.

Embodiment II-73

The method of any one of Embodiments II-42 to II-72, wherein the first probe is characterized by a thermodynamic fulcrum and/or melting temperature of about 52° C.

Embodiment II-74

The method of any one of Embodiments II-42 to II-73, wherein the first probe comprises between 12 and 25 nucleotides.

Embodiment II-75

The method of Embodiment II-74, wherein the first probe comprises between 18 and 22 nucleotides.

Embodiment II-76

The method of any one of Embodiments II-42 to II-75, wherein the first probe has a melting temperature of between 50° C. and 60° C.

Embodiment II-77

The method of any one of Embodiments II-42 to II-76, wherein the first probe comprises, consists essentially of, or consists of a sequence selected from any one of SEQ ID NO: 14-20.

Embodiment II-78

The method of any one of Embodiments II-42 to II-77, wherein the second probe comprises between 12 and 25 nucleotides.

Embodiment II-79

The method of Embodiment II-78, wherein the second probe comprises between 18 and 22 nucleotides.

Embodiment II-80

The method of any one of Embodiments II-42 to II-79, wherein the second probe has a melting temperature of between 50° C. and 60° C.

Embodiment II-81

The method of any one of Embodiments II-42 to II-80, wherein the second probe comprises, consists essentially of, or consist of a sequence selected from any one of SEQ ID NO: 6 or 22.

Embodiment II-82

The method of any one of Embodiments II-42 to II-79, wherein the molecular diagnostic device detects the allele in a biological sample comprising at least about 0.5 nM, at least about 1 nM, at least about 1.5 nM, at least about 2 nM, at least about 6 nM, at least about 8 nM, at least about 10 nM, or at least about 15 nM of the polynucleotide comprising the SNP locus if the SNP locus comprises the allele.

Embodiment II-83

The method of any one of Embodiments II-42 to II-82, wherein the molecular diagnostic device determines whether a subject suspected of having a drug-sensitive bacterial infection has a drug-sensitive bacterial infection.

Embodiment II-84

The method of any one of Embodiments II-42 to II-83, wherein the molecular diagnostic device determines whether a subject suspected of having a drug-resistant bacterial infection has a drug-resistant bacterial infection.

Although various embodiments have been described as having particular features and/or combinations of components, other embodiments are possible having a combination of any features and/or components from any of the embodiments as discussed above.

EXAMPLES

Example 1: Design and Evaluations of Primers to Amplify GyrA Region Encompassing Cipro-Resistance SNP Locus 108 bp Amplicon Several primer sets were design to target the SNP locus for serine 91 (Ser-91) in the gyrA gene (SEQ ID NO: 1). A first primer set design is shown underlined below. The target amplicon (uppercase letters) has a calculated melting temperature of 63° C. and a length of 108 bp. The codon TCC (in brackets) encoding a serine in wild-type strains has a SNP at the middle T resulting in a TTC codon encoding phenylalanine. The substitution results in Cipro-resistance.

(SEQ ID NO: 1)

```
   1 atgaccgacg caaccatccg ccacgaccac aaattcgccc tcgaaaccct gcccgtcagc
  61 cttgaagacg aaatgcgcaa aagctatctc gactacgcca tgagcgtcat tgtcgggcgc
 121 gcgctgccgg acgttcgcga cggcctaaag ccggtgcacc ggcgcgtact gtacgcgatg
 181 cacgagctga aaataactg gaatgccgcc tacaaaaaat cggCGCGCAT CGTCGGCGAC
 241 GTCATCGGTA AATACCACCC CCACGGCGAT [TCC]GCAGTTT ACGACACCAT CGTCCGTATG
 301 GCGCAAAATT TCGCTATGCG TTATGTGCTG Atagacggac agggcaactt cggatcggtg
 361 gacgggcttg ccgccgcagc catgcgctat accgaaatcc gcatggcgaa aatctcacat
 421 gaaatgctgg cagacattga ggaagaaacc gttaatttcg ccccgaacta cgacggtagc
 481 gaacacgagc cgcttgtact gccgacccgt ttccccacac tgctcgtcaa cggctcgtcc
 541 ggtatcgccg tcggtatggc gaccaacatc ccgccgcaca acctcaccga caccatcaac
 601 gcctgtctgc gtcttttgga cgaacccaaa accgaaatcg acgaactgat cgacattatc
 661 caagcccccg acttcccgac cggggcaacc atctacggct gggcggcgt gcgcgaaggc
 721 tataaaacag gccgcggccg cgttgttatg cgcggtaaga cccatatcga acccataggc
 781 aaaaacggcg aacgcgaacg catcgttatc gacgaaatcc cctatcaggt caacaaagcc
 841 aagttggtcg agaaaatcgg cgatttggtt cgggaaaaaa cactggaagg catttccgag
 901 ctccgcgacg aatccgacaa atccggtatg cgcgtcgtta tcgagctgaa acgcaacgaa
 961 aatgccgaag tcgtcttaaa ccaactctac aaactgactc cgctgcaaga cagtttcggc
1021 atcaatatgg tggttttggt cgacggacaa ccgcgcctgt taaacctgaa acagattctc
1081 tccgaattcc tgcgccaccg ccgcgaagtc gttacccgac gtacgctttt ccggctgaag
1141 aaggcacgcc atgaagggca tatcgccgaa cggaaagccg tcgcactgtc caatatcgat
1201 gaaatcatca agctcatcaa agaatcgccc aacgcggccg aggccaaaga aaaactgctt
1261 gcgcgccctt gggccagcag cctcgttgaa gaaatgctga cgcgttccgg tctggatttg
1321 gaaatgatgc gtccggaagg attggtcgca acattggtc tgaaaaaaca aggttattac
1381 ctgagcgaga ttcaggcaga tgctatttta cgcatgagcc tgcgaaacct gaccggcctc
1441 gatcagaaag aaattatcga aagctacaaa aacctgatgg gtaaaatcat cgactttgtg
1501 gatatcctct ccaaacccga acgcattacc caaatcatcc gtgacgaact ggaagaaatc
1561 aaaaccaact atggcgacga acgccgcagc gaaatcaacc cgttcggcgg cgacattgcc
1621 gatgaagacc tgattccgca acgcgaaatg gtcgtgaccc tgacccacgg cggctatata
1681 aaaacccagc cgaccaccga ctatcaggct cagcgtcgcg gcgggcgcgg caaacaggcg
1741 gctgccacca agacgaaga ctttatcgaa accctgtttg ttgccaacac gcatgactat
1801 ttgatgtgtt ttaccaacct cggcaagtgc cactggatta aggttacaa actgcccgaa
1861 ggcggacgca acagccgcgg ccgtccgatt aacaacgtca tccagctgga agaaggcgaa
1921 aaagtcagcg cgattctggc agtacgcgag tttcccgaag accaatacgt cttcttcgcc
1981 accgcgcagg gaatggtgaa aaaagtccaa ctttccgcct taaaaacgt ccgcgcccaa
2041 ggcattaaag ccatcgcact caaagaaggc gactacctcg tcggcgctgc gcaaacaggc
2101 ggtgcggacg acattatgtt gttctccaac ttgggcaaag ccatccgctt caacgaatac
2161 tgggaaaaat ccggcaacga cgaagcggaa gatgccgaca tgaaaccga gatttcagac
2221 gacctcgaag acgaaaccgc cgacaacgaa aacaccctgc caagcggcaa aaacggcgtg
2281 cgtccgtccg gtcgcggcag cggcggtttg cgcggtatgc gcctgcctgc cgacggcaaa
2341 atcgtcagcc tgattacctt cgcccctgaa accgaagaaa gcggtttgca agttttaacc
```

```
-continued
2401 gccaccgcca acggatacgg aaaacgcacc ccgattgccg attacagccg caaaaacaaa 2461 ggcgggcaag gcagtattgc cattaacacc ggcgagcgca acggcgattt ggtcgccgca 2521 accttggtcg gcgaaaccga cgatttgatg ctgattacca gcggcggcgt gcttatccgt 2581 accaaagtcg aacaaatccg cgaaaccggc cgcgccgcag caggcgtgaa actgattaac 2641 ttggacgaag gcgaaacctt ggtatcgctg gaacgtgttg ccgaagacga atccgaactc 2701 tccggcgctt ctgtaatttc caatgtaacc gaaccggaag ccgagaactg a
```

The 108 bp target amplicon therefore has the sequence:

```
                                                          (SEQ ID NO: 7)
  1 CGCGCATCGT CGGCGACGTC ATCGGTAAAT ACCACCCCCA CGGCGATTCC GCAGTTTACG

61 ACACCATCGT CCGTATGGCG CAAAATTTCG CTATGCGTTA TGTGCTGA
```

Polymerase chain reaction (PCR) amplification was performed with the following parameters and using the oligonucleotide primers listed below. The reverse primer was 5' labeled to permit detection of the target amplicon. "/5BiosG/" refers to a biotin conjugated to the reverse primer via a linker, having the formula depicted below:

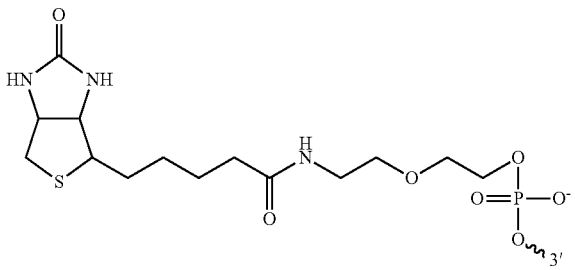

Final Reaction Concentrations:

500 nM Forward Primer: 5'-GCGCATCGTCG-3' (SEQ ID NO: 8)

500 nM Reverse Primer: 5'-/5BiosG/TCAGCACAT-AACGCATAGC-3' (SEQ ID NO: 9)

10,000 copies gDNA 75 mM KCl, 4 mM MgCl$_2$, 0.06 U/uL KAPA, 200 uM dNTP

| Thermocycling Parameters | | | |
|---|---|---|---|
| Step | Temperature | Time (mm:ss) | # of cycles |
| Pre-incubation | 95° C. | 03:00 | 1 |
| Denaturing | 95° C. | 00:05 | 50 |
| Annealing | 60° C. | 00:10 | 50 |

Figure 20A:
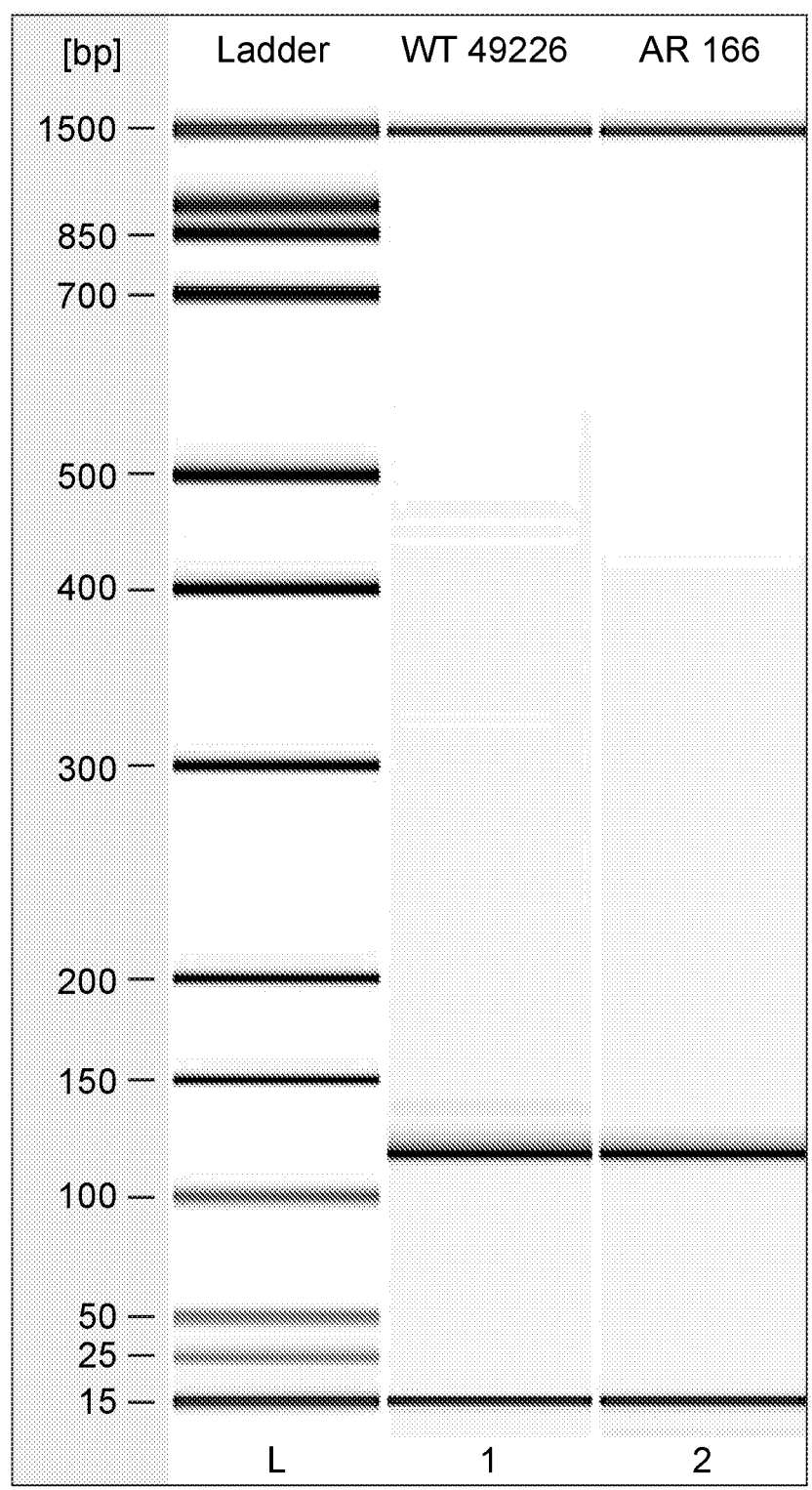
FIG. 20A and FIG. 20B show capillary electrophoresis analysis of target amplicon produced by PCR using polynucleotide samples from various *N. gonorrhoeae* strains as template.
Figure 20B:
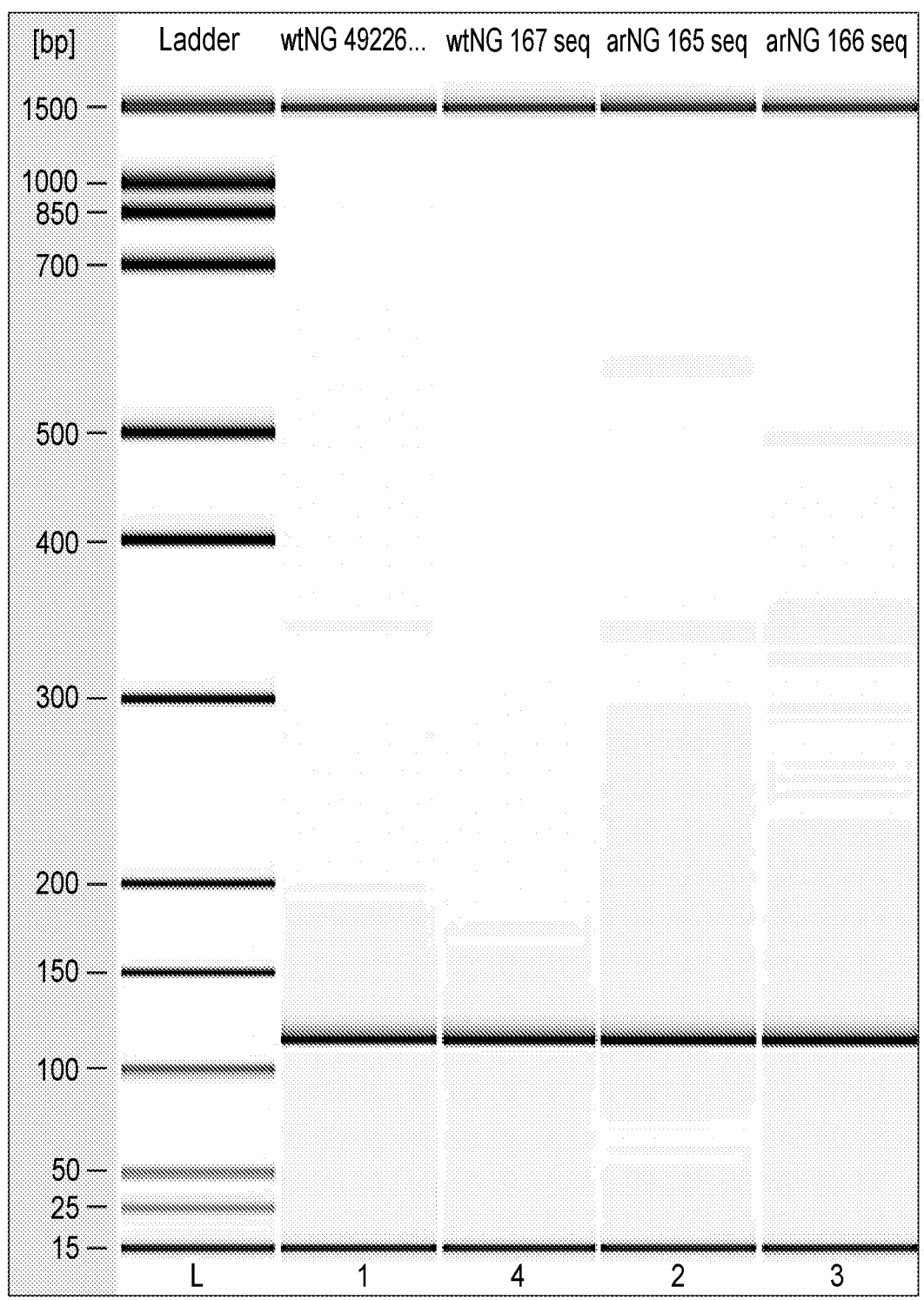

Amplification of the desired amplicon (SEQ ID NO: 7) was confirmed by capillary electrophoresis (FIG. 20A) Similar results were achieved with four experimental strains: (WT) Ser91 ATCC 49226; (WT) Ser91 CDC 167; (AR) Phe91 CDC 165; and (AR) Phe91 CDC 166 (FIG. 20B). Sequencing of the target amplicons confirmed the correct nucleotide was present (data not shown).

34 bp Amplicon

Similar PCR conditions were used to produce a shorter amplicon (SEQ ID NO: 10).

Final Reaction Concentrations:

300 nM Forward Primer: 5'-CCCCCACGGCGATTCC-3' (SEQ ID NO: 11)

300 nM Reverse Primer: 5'-/5BiosG/GATGGTGTCGTAAACTGCGGA-3' (SEQ ID NO: 12)

10,000 copies gDNA 75 mM KCl, 4 mM MgCl$_2$, 0.06 U/uL KAPA, 200 uM dNTP

Thermocycling Parameters:

| Thermocycling Parameters: | | | |
|---|---|---|---|
| Step | Temperature | Time (mm:ss) | # of cycles |
| Pre-incubation | 95° C. | 00:20 | 1 |
| Denaturing | 95° C. | 00:01 | 40 |
| Annealing | 60° C. | 00:06 | 40 |

The configuration of forward primer (SEQ ID NO: 11) and the reverse-complement (SEQ ID NO: 13) of the reverse primer (SEQ ID NO: 12) used to generate the target amplicon (SEQ ID NO: 10) are indicated below:

```
CCCCCACGGCGATTCC (SEQ ID NO: 11)

CCCCCACGGCGATTCCGCAGTTTACGACACCATC (SEQ ID NO: 10)

TCCGCAGTTTACGACACCATC (SEQ ID NO: 13)
```

Figure 21:
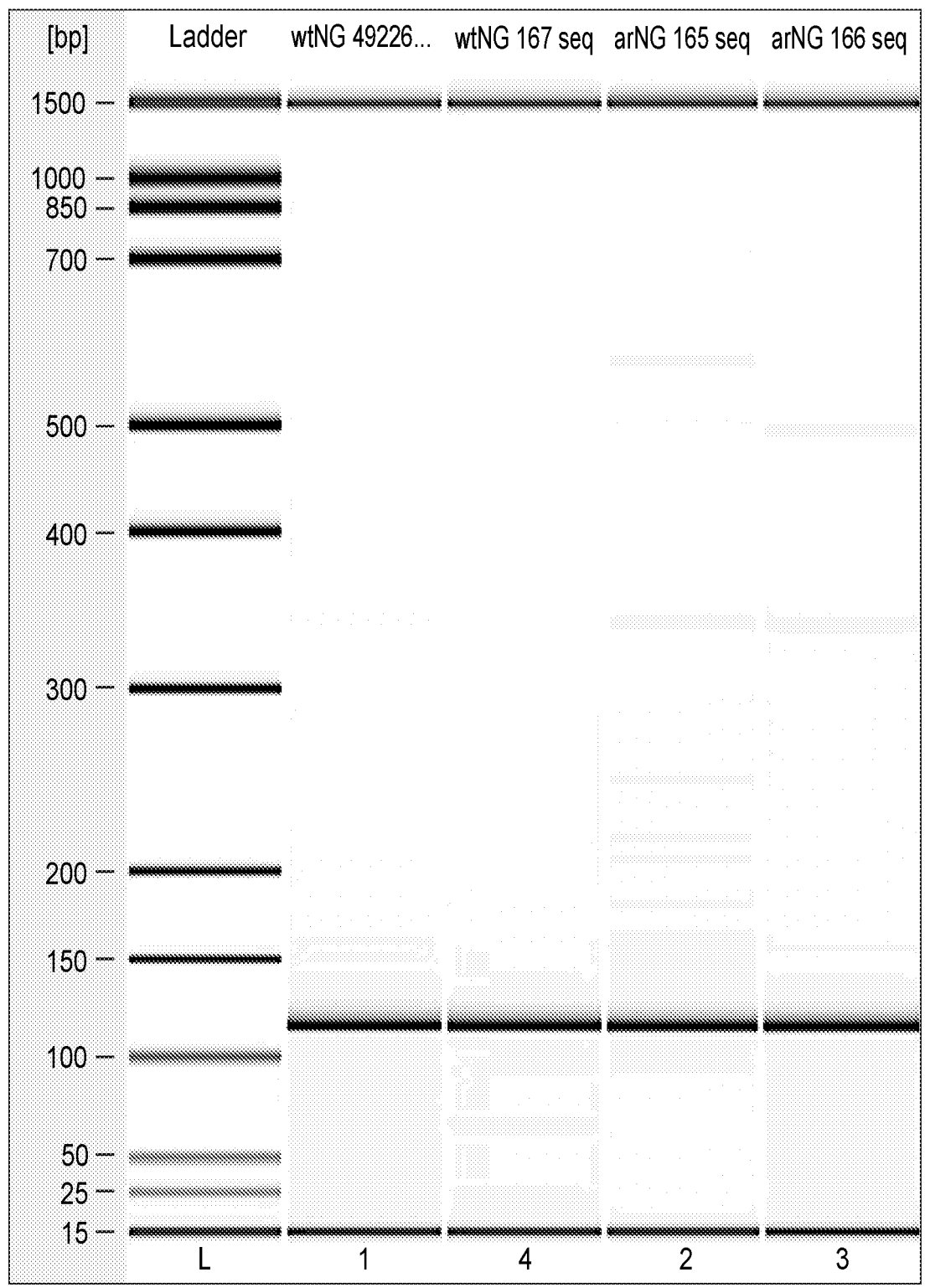
FIG. 21 show capillary electrophoresis analysis of target amplicon produced by PCR using polynucleotide samples from various *N. gonorrhoeae* strains as template.

Due to overlap with Ser-91 gyrA the primers are sequence-specific. Amplification of the 34 bp target amplicon was confirmed by capillary electrophoresis (FIG. 21).

Example 2: Design and Evaluation of Four Probes for SNP Detection at Ser-91 gyrA Melting temperature analysis was performed on the 108 bp and 34 bp amplicons (Table 3).

TABLE 3

| | Ser91 | Phe91 |
|---|---|---|
| 108 bp | 56.7° C. | 57.5° C. |
| 34 bp | 64.2° C. | 64.6° C. |

Four probes were designed to match the Cipro sensitive allele the Ser91 gryA SNP locus (Table 4). Probes 3 and 4 included intentional mismatches to lower the melting temperatures of the probes. The mismatch to the gyrA sequence is denoted by italics and by an arrow pointing to the mismatched base (mismatch↑). The melting temperatures were calculated using DNASoftware™ Visual OMP™.

TABLE 4

| Probe | SEQUENCE | SEQ ID NO: | Ser91 | Phe91 |
|---|---|---|---|---|
| 1 | /5AmMC6/CGGCGAT-TCCGCAGTT | 14 | 63.7° C. | 52.4° C. |
| 2 | /5AmMC6/CGGCGATTCCGCAGT | 15 | 64.4° C. | 54.0° C. |
| 3 | /5AmMC6/CGGTGATTCCGCAGT mismatch↑ | 16 | 55.7° C. | 41.3° C. |
| 4 | /5AmMC6/CGGCTATTCCGCAGT mismatch↑ | 17 | 52.0° C. | 35.9° C. |

"/5AmMC6/" refers to an amine-reactive moeity conjugated to the probe via a linker, to permit attachment of the probe to the surface of the detection module through reaction with activated carboxylate groups on the surface of the detection module. 5AmMC6 has the formula depicted below:

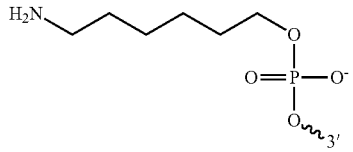

Each of the probes was covalently linked to the surface of microtiter plates by amine-reactive cross-linker chemistry:
1. Dilute probe (with amino linker) to 0.25 µM with sodium bicarbonate buffer.
2. Add 100 µL of the diluted probe to a well of the plate.
3. Seal the plate with sealing film and incubate for 30 minutes at room temperature.
4. Remove the probe solution.
5. Wash twice with 1×PBS.
6. Add 200 µL of Stabilcoat® immunoassay blocker/stabilizer, cover with sealing film and incubate for 2 hours at room temperature.
7. Remove the blocking solution.
8. Store the plate inside a foil bag with desiccant. Store at 2-6° C.

Binding to each of the amplicons from Example 1 was performed according to the following conditions.
Amplicon: 20 nM
Probe: 0.25 µM
Plate Temperature: 48.8-49.8° C.
NTC: no probe+NS amplicon
Pos: NS probe+NS amplicon (reaction positive control)
Steps:
9. Add amplicon and incubate 10 min
10. Wash (0.02% TWEEN®-20 in 1×PBS)
11. Add HRP (1 µg/mL)
12. Wash (0.02% TWEEN®-20 in 1×PBS)
13. Add substrate (TMB PLUS2)

Figure 22:
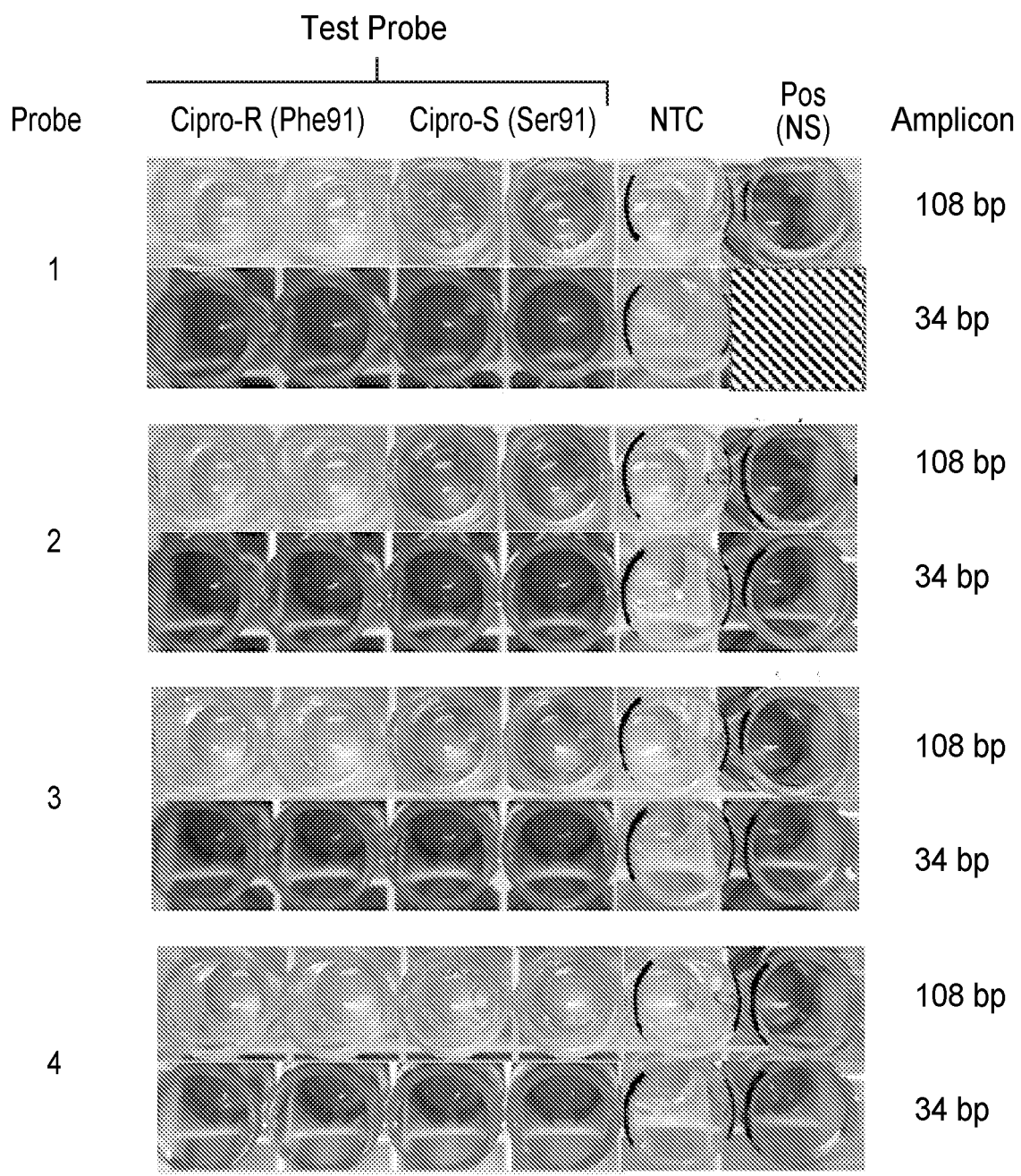
FIG. 22 shows allele-specific hybridization of 108 bp or 34 bp amplicons to surface-linked probes 1-4 in a microtiter plate format.

The binding of target amplicon to probe (detected by HRP-catalyzed conversion of TMB to 3,3',5,5'-tetramethylbenzidine diimine) is shown in FIG. 22. Binding of the 108 bp template to each of the probes discriminates between Cipro-R and Cipro-S alleles at the Ser91 gyrA SNP locus.

Example 3: Design and Evaluation of Four Probes for SNP Detection at Ser-91 gyrA Using Enhanced Wash Buffer Three additional probes were designed to match the Cipro sensitive allele at the Ser91 gryA SNP locus (Table 5). Probes 5, 6 and 8 (like probes 3 and 4) included intentional mismatches to lower the melting temperatures of the probes. The mismatch to the gyrA sequence is denoted by italics and by an arrow pointing to the mismatched base (mismatch↑).

TABLE 5

| Probe | SEQUENCE | SEQ ID NO: | Ser91 | Phe91 |
|---|---|---|---|---|
| 1 | /5AmMC6/CGGCGATTCCGCAGTT | 14 | 63.9° C. | 53.4° C. |
| 2 | /5AmMC6/CGGCGATTCCGCAGT | 15 | 63.2° C. | 51.8° C. |
| 3 | /5AmMC6/CGGTGATTCCGCAGT mismatch↑ | 16 | 55.2° C. | 40.7° C. |
| 4 | /5AmMC6/CGGCTATTCCGCAGT mismatch↑ | 17 | 51.5° C. | 35.2° C. |
| 5 | /5AmMC6/CGGCGATTCGGCAGT mismatch↑ | 18 | 53.4 | 43.8 |
| 6 | n/a | n/a | n/a | n/a |
| 7 | /5AmMC6/CACGGCTATTCCGCAGTTT mismatch↑ | 19 | 58.4 | 46.5 |
| 8 | /5AmMC6/TACGGCTATTCCGCAGTTT mismatch↑  ↑mismatch | 20 | 55.9 | 43.1 |

Figure 23:
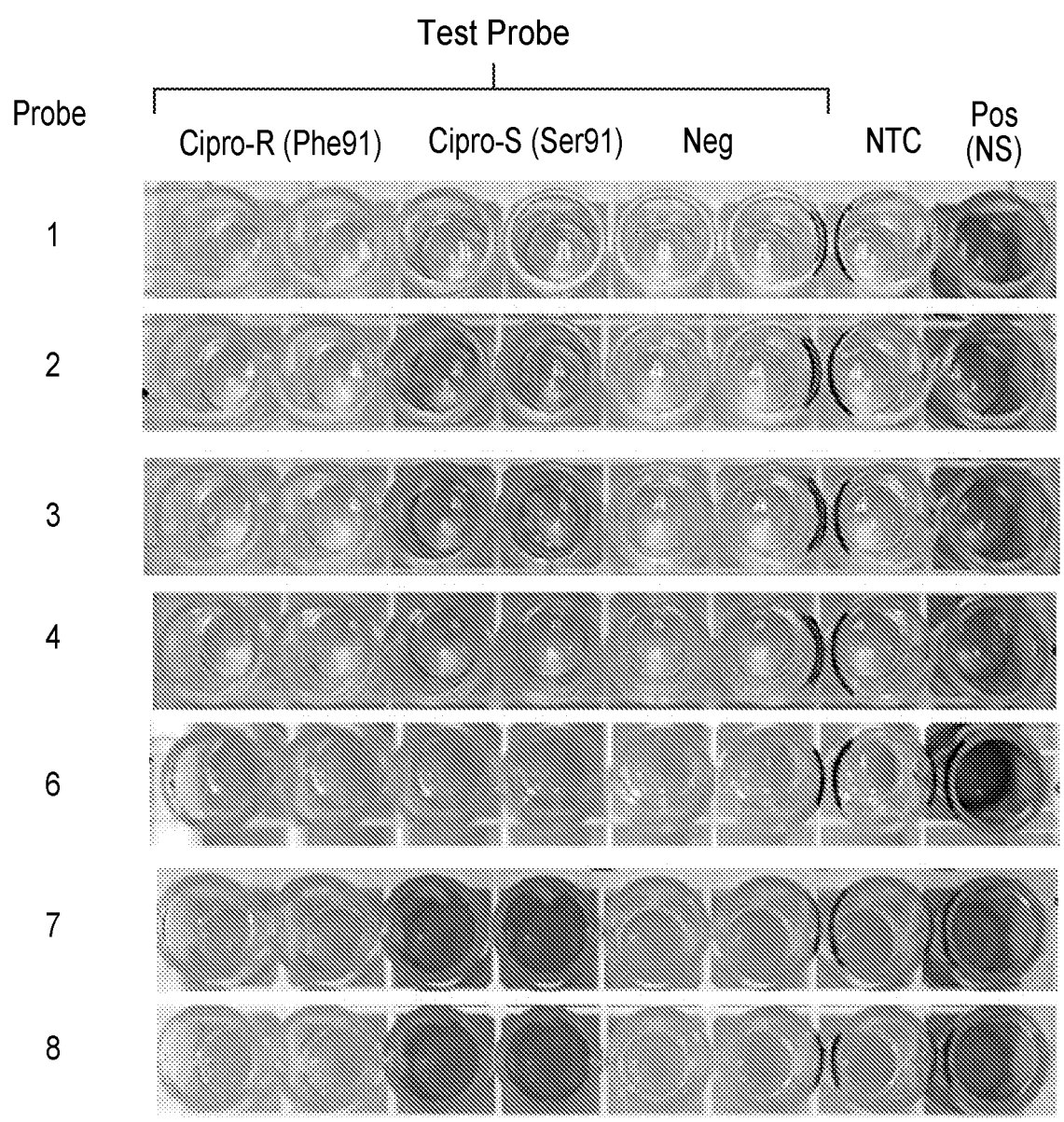
FIG. 23 shows allele-specific hybridization of 108 bp or 34 bp amplicons to surface-linked probes 1-5 and 7-8 in a microtiter plate format.

Results for testing of these probes according to the following protocol are shown in Table 6 and Table 7 and FIG. 23. Binding of the 108 bp template to each of the probes discriminates between Cipro-R and Cipro-S alleles at the Ser91 gyrA SNP locus.

Conditions
  Amplicon: 20 nM
  Probe: 0.25 µM
  Plate Temperature: 48.5-49.8° C.
  Neg: Test probe+NS amplicon
  NTC: no probe+NS amplicon
  Pos: NS probe+NS amplicon (reaction positive control)

Enhanced Wash Buffer
  1× phosphate buffered saline (PBS)
  76.92 mM KCl
  1.92 mM $MgCl_2$
  0.03% ProClin300 (v/v)
  0.02% Tween-20 (v/v), pH 7.4

Steps
1. Add amplicon and incubate 10 min
2. Wash (enhanced wash buffer)
3. Add HRP (1 µg/mL)
4. Wash (enhanced wash buffer)
5. Add substrate (TMB PLUS2)

TABLE 6

| | 640 nm Absorbance | | | | |
|---|---|---|---|---|---|
| Probe | Cipro-R (Phe91) | Cipro-S (Ser91) | Neg | NTC | Pos (NS) |
| 1 | 0.047 | 0.098 | 0.042 | 0.043 | 0.658 |
| 2 | 0.062 | 0.272 | 0.0397 | 0.058 | 0.528 |
| 3 | 0.043 | 0.304 | 0.040 | 0.046 | 0.625 |
| 4 | 0.0453 | 0.139 | 0.042 | 0.067 | 0.544 |
| 5 | 0.045 | 0.0780 | 0.046 | 0.045 | 0.884 |
| 6 | n/a | n/a | n/a | n/a | n/a |
| 7 | 0.919 | 0.610 | 0.038 | 0.045 | 0.617 |
| 8 | 0.058 | 0.535 | 0.039 | 0.038 | 0.670 |

TABLE 7

| | Signal:Background | | | | |
|---|---|---|---|---|---|
| Probe | Cipro-R (Phe91) | Cipro-S (Ser91) | Neg | NTC | Pos (NS) |
| 1 | 1.113 | 2.329 | 1 | N/A | N/A |
| 2 | 1.568 | 6.848 | 1 | N/A | N/A |
| 3 | 1.069 | 7.527 | 1 | N/A | N/A |
| 4 | 1.079 | 3.302 | 1 | N/A | N/A |
| 5 | n/d | n/d | n/d | n/d | n/d |
| 6 | n/a | n/a | n/a | n/a | n/a |
| 7 | n/d | n/d | n/d | n/d | n/d |
| 8 | n/d | n/d | n/d | n/d | n/d |

Example 4: Design and Evaluation of 68 bp Target Amplicon Using Second Probe as Internal Control An additional target amplicon was tested using primers designed to flank the gryA-Ser91 SNP locus and to produce a 68 bp product:

```
Forward Primer:
                                      (SEQ ID NO: 8)
5'-GCGCATCGTCG-3'

Reverse Primer:
                                      (SEQ ID NO: 21)
5'-/5BiosG/GATGGTGTCGTAAACTGCG-3'

Control Probe:
                                      (SEQ ID NO: 22)
5'-TCATCGGTAAATACCACCCCC-3'

Target Amplicon:
                                      (SEQ ID NO: 23)
CGCGCATCGTCGGCGACGTCATCGGTAAATACCACCCCCACGGCGATTC
CGCAGTTTACGACACCATC
```

The control probe (SEQ ID NO: 22) was to designed to bind within the same target amplicon as the allele-specific probes 1-5 and 7-8. The control probe and allele-specific probe binding sites do not overlap. Template from Cipro-sensitive strains CDC 167 and CDC 175 or from Cipro-resistant strains CDC 166 and CDC168 was PCR-amplified using standard parameters.

Figure 24:
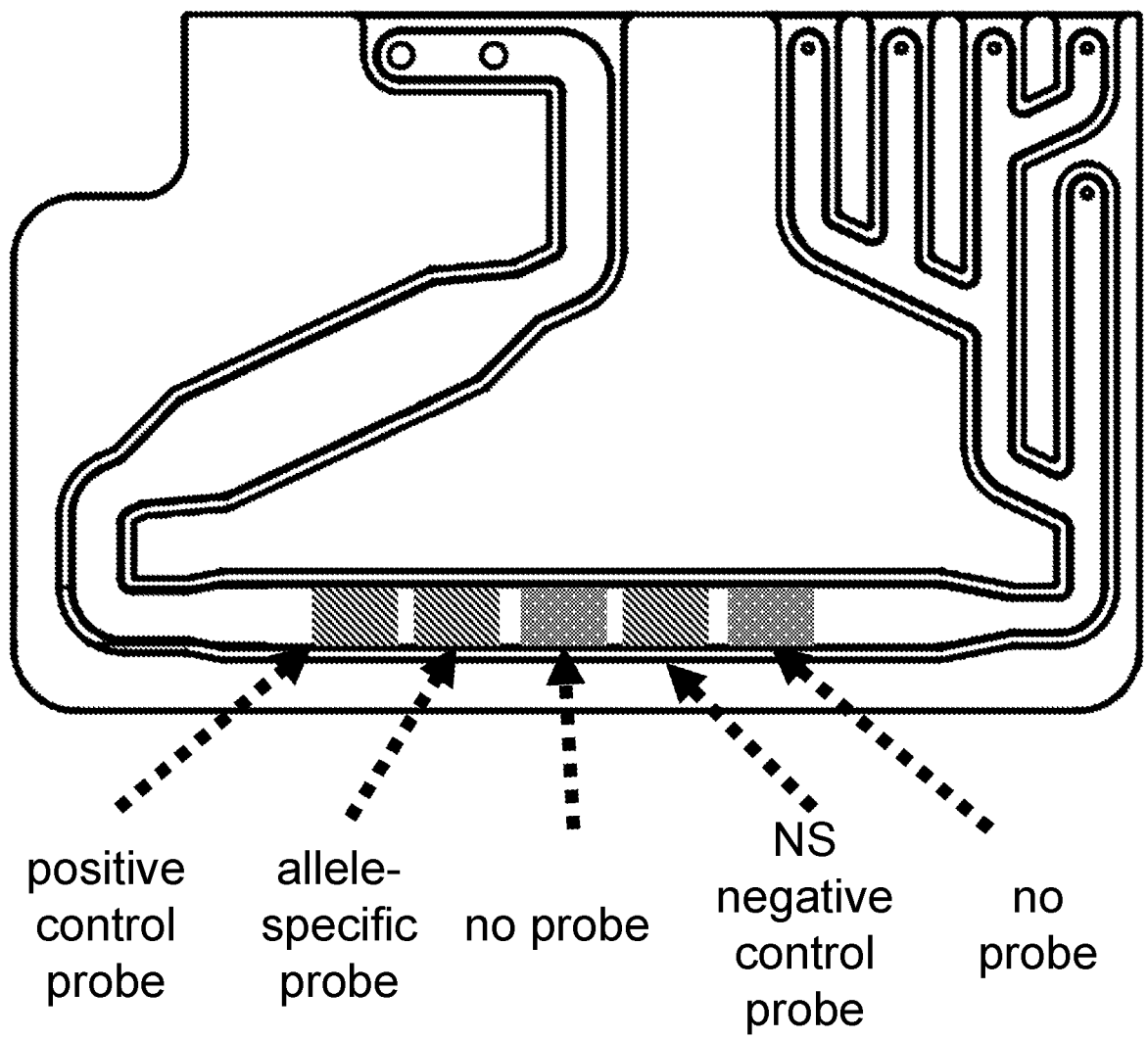
FIG. 24 is a schematic illustration of a detection module showing the position of five detection surfaces used in experimental evaluation of probe designs.

A detection module (also termed a flow cell) was configured as shown in FIG. 24. The 68 bp amplicons from each strain were passed through the flow cell; detection reagent 1 (HRP) was then added; followed by a wash with enhanced wash buffer; and substrate (TMB) addition using the following volumes and flow rates. All steps were performed at 52° C.

1. Amplicon hybridization. 60 µL. 0.35 µL/s.
2. Enzyme (HRP). 270 µL. 5 µL/s
3. Wash (Enhanced Wash Buffer) 270 µL. 5 µL/s
4. Substrate. 270 µL. 5 µL/s. 2×

Figure 25:
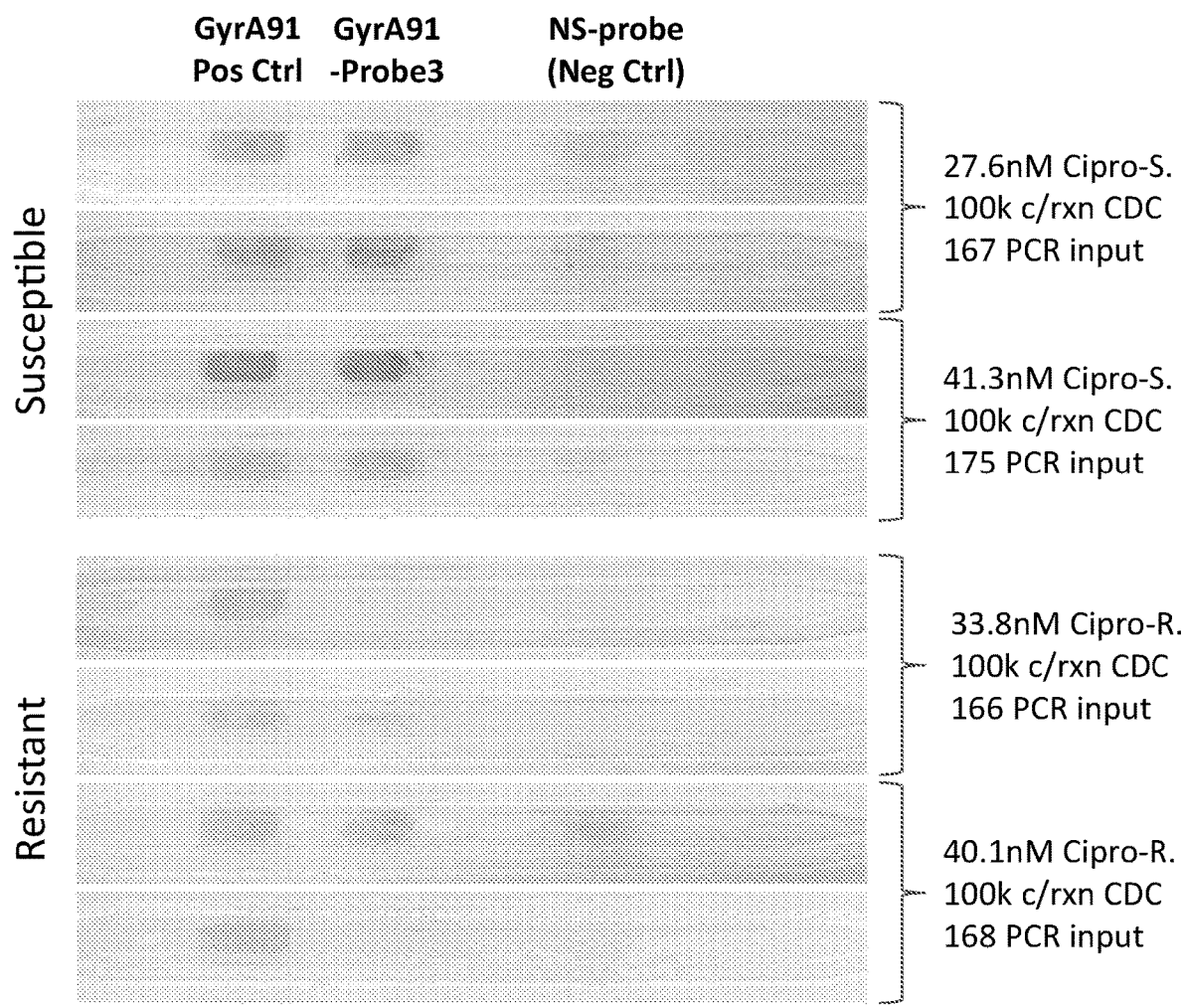
FIG. 25 shows colorimetric detection of target amplicon from susceptible (Cipro-S) and resistance (Cipro-R) strains of gonorrhea binding to allele-specific probe 3.

The experiments demonstrates that control probe (SEQ ID NO: 22) and allele-specific probe 3 (SEQ ID NO: 16) discriminate between Cipro-sensitive (Cipro-S) and Cipro-resistance (Cipro-R) strains (FIG. 25).

Figure 26:
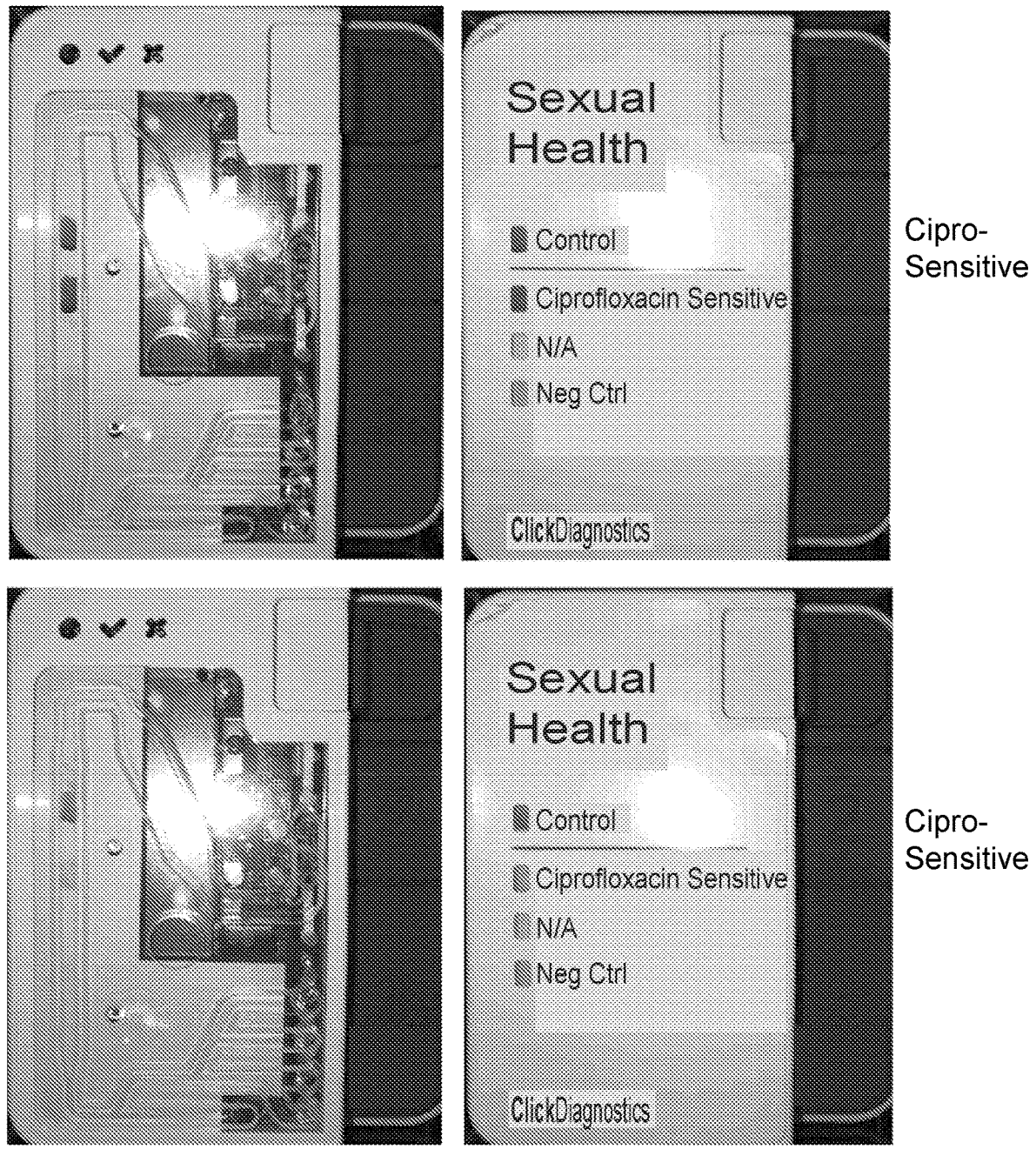
FIG. 26 and FIG. 27 show testing of illustrative devices demonstrating discrimination between Cipro-sensitive and Cipro-resistant strains.
Figure 27:
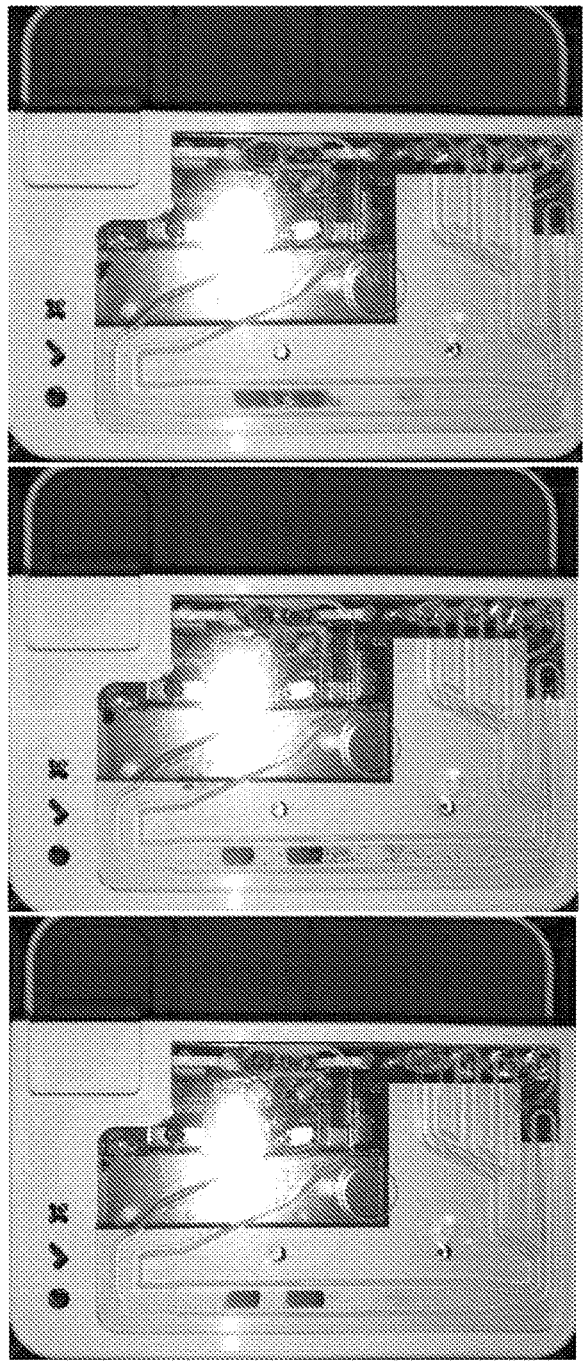
Figure 27:
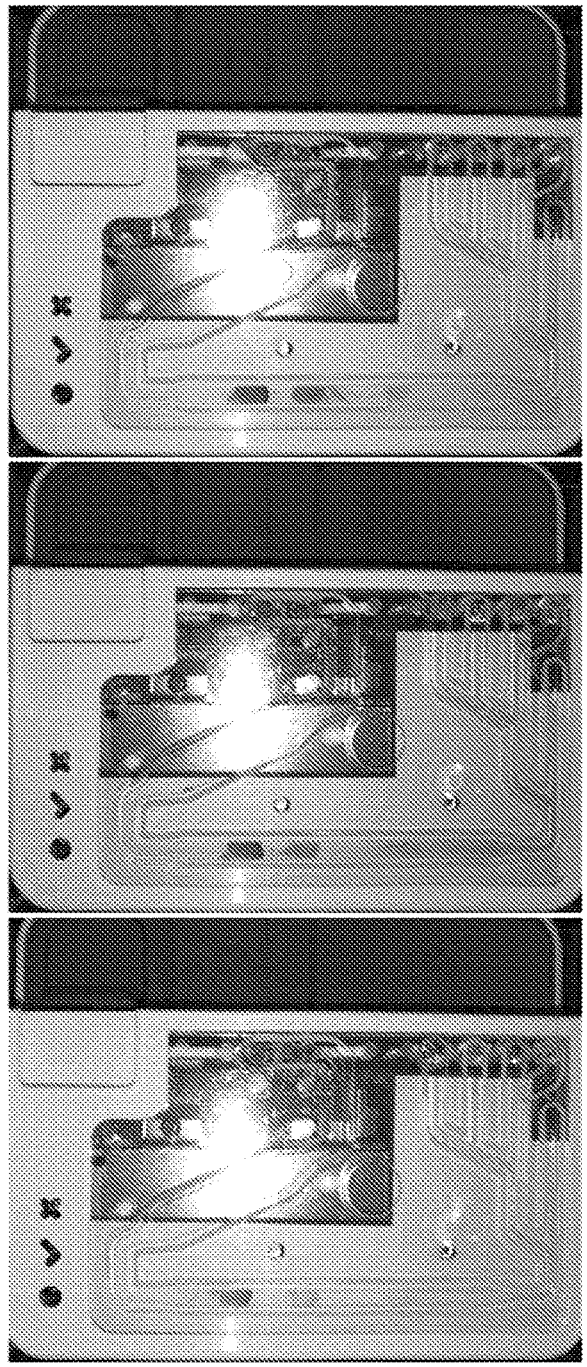

To determine a limit of detection, experiments were run under similar conditions using as few as 100,000 bacterial genomes per reaction as the input material. FIG. 26 and FIG. 27 demonstrates that the device discriminates between sensitive and resistance strains even at this low sample concentration. Signal from the allele-specific probe is reduced compared to signal from the control probe when template from Cipro-resistant strains is tested. Strong signal from both probes is observed when template from Cipro-sensitive strains is tested.

For foregoing examples are for illustration only and do not limit the scope of the invention, which is defined by the following claims.

What is claimed is:

1. A molecular diagnostic device, comprising:
   a sample preparation module configured to receive a biological sample, wherein the biological sample comprises a polynucleotide;
   a reagent module containing a primer set targeting a single nucleotide polymorphism (SNP) locus in the polynucleotide;
   an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and
   a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele,
   wherein the target allele is a drug-resistance allele, and the molecular diagnostic device specifically detects the drug-resistance allele in the biological sample.

2. The molecular diagnostic device of claim 1, wherein the primer set is designed to flank the SNP locus.

3. The molecular diagnostic device of claim 1, wherein the primer set targeting the SNP locus comprises:
   i) an upstream oligonucleotide primer substantially complementary to an upstream primer binding site at the 5' terminus of the target region on the antisense strand; and
   ii) a downstream oligonucleotide primer substantially complementary to a downstream primer binding site at the 3' terminus of the target region on the sense strand.

4. The molecular diagnostic device of claim 1, wherein the molecular diagnostic device comprises a temperature controller configured to maintain the temperature of the detection module at about 10° C. less than the melting temperature of the probe.

5. The molecular diagnostic device of claim 1, wherein the probe comprises at most two nucleotide mismatches to the probe binding site.

6. The molecular diagnostic device of claim 1, wherein the probe is perfectly complementary to the probe binding site.

7. The molecular diagnostic device of claim 1, wherein the detection module comprises a second probe substantially complementary to a second probe binding site, wherein the second probe binding site does not comprise the SNP locus.

8. The molecular diagnostic device of claim 7, wherein the second probe comprises between 12 and 25 nucleotides.

9. The molecular diagnostic device of claim 7, wherein the second probe has a melting temperature of between 50° C. and 60° C.

10. The molecular diagnostic device of claim 7, wherein the second probe comprises a sequence selected from any one of SEQ ID NO: 6 or 22.

11. The molecular diagnostic device of claim 1, wherein the alternative allele is a drug-sensitivity allele.

12. The molecular diagnostic device of claim 1, wherein the SNP locus is within a gyrA region.

13. The molecular diagnostic device of claim 1, wherein the primer set is designed to flank the gyrA 91 locus.

14. The molecular diagnostic device of claim 1, wherein the probe is designed to maximize binding to the wild type, ciprofloxacin-sensitive gyrA Ser-91 genotype while minimizing binding to other SNPs at a gyrA Ser-91 site that confers a drug resistance.

15. The molecular diagnostic device of claim 1, wherein the probe is substantially complementary to a probe binding site comprising the codon encoding gyrA Ser-91, and wherein the probe comprises a nucleotide that matches an allele encoding ciprofloxacin-sensitive gyrA Ser-91 genotype.

16. The molecular diagnostic device of claim 1, wherein the probe discriminates between an allele encoding the ciprofloxacin-sensitive gyrA Ser-91 genotype and the anti-allele encoding the gyrA Phe-91 site that confers resistance to ciprofloxacin.

17. The molecular diagnostic device of claim 1, wherein the probe is characterized by a thermodynamic fulcrum of about 52° C.

18. The molecular diagnostic device of claim 1, wherein the probe comprises a sequence selected from any one of SEQ ID NO: 14-20.

19. The molecular diagnostic device of claim 1, wherein the molecular diagnostic device determines whether a subject suspected of having a drug-sensitive bacterial infection has a drug-sensitive bacterial infection.

20. The molecular diagnostic device of claim 1, wherein the molecular diagnostic device determines whether a subject suspected of having a drug-resistant bacterial infection has a drug-resistant bacterial infection.

21. A method, comprising:
a) introducing into the molecular diagnostic device of claim 1 a biological sample from a subject having or suspected of having a disease or disorder characterized by one or more SNPs associated with susceptibility to a treatment, wherein the biological sample comprising a polynucleotide from the subject,
b) administering the treatment if the molecular diagnostic device indicates the polynucleotide comprises a SNP locus comprising an allele associated with susceptibility to the treatment.

22. The method of claim 21, wherein the disease or disorder is a bacterial infection.

* * * * *